(12) United States Patent
Chang et al.

(10) Patent No.: US 8,835,420 B2
(45) Date of Patent: Sep. 16, 2014

(54) AZAINDOLE DERIVATIVES

(71) Applicant: Takeda Pharmaceutical Company Limited, San Diego, CA (US)

(72) Inventors: Edcon Chang, San Diego, CA (US); Wolfgang Reinhard Ludwig Notz, San Diego, CA (US); Michael B. Wallace, San Diego, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 13/937,081

(22) Filed: Jul. 8, 2013

(65) Prior Publication Data

US 2014/0018344 A1    Jan. 16, 2014

Related U.S. Application Data

(60) Provisional application No. 61/670,116, filed on Jul. 10, 2012.

(51) Int. Cl.

| | | |
|---|---|---|
| A61K 31/395 | (2006.01) | |
| A61K 31/535 | (2006.01) | |
| A61K 31/519 | (2006.01) | |
| A61K 31/52 | (2006.01) | |
| A61K 31/522 | (2006.01) | |
| A61K 31/505 | (2006.01) | |
| C07D 413/14 | (2006.01) | |
| C07D 487/04 | (2006.01) | |
| C07D 473/02 | (2006.01) | |
| C07D 403/12 | (2006.01) | |
| C07D 519/00 | (2006.01) | |
| A61K 31/5377 | (2006.01) | |
| C07D 491/107 | (2006.01) | |
| A61K 45/06 | (2006.01) | |
| A61K 31/506 | (2006.01) | |
| C07D 471/04 | (2006.01) | |

(52) U.S. Cl.
CPC ............ C07D 471/04 (2013.01); C07D 519/00 (2013.01); A61K 31/5377 (2013.01); A61K 31/52 (2013.01); C07D 491/107 (2013.01); A61K 45/06 (2013.01); C07D 487/04 (2013.01); A61K 31/506 (2013.01); A61K 31/519 (2013.01)
USPC ................ 514/210.21; 514/234.5; 514/262.1; 514/263.22; 514/275; 544/118; 544/122; 544/262; 544/277; 544/324

(58) Field of Classification Search
CPC ..... A61K 31/70; A61K 31/67; A61K 31/165; A61K 31/415; A61K 31/44; A61K 31/535; C07D 239/02; C07D 239/42; C07D 413/02; C07D 213/56; C07D 277/30; C07D 261/06; C07D 233/54; C07D 307/02; C07D 235/02
USPC ............ 514/118, 122, 262, 277, 324, 210.21, 514/234.5, 262.1, 263.22, 275; 544/210.21, 544/234.5, 262.1, 263.22, 275, 118, 122, 544/262, 277, 324
See application file for complete search history.

(56) References Cited

U.S. PATENT DOCUMENTS

| | | | |
|---|---|---|---|
| 6,806,272 | B2 | 10/2004 | Bauer et al. |
| 6,861,422 | B2 | 3/2005 | Hoffmann et al. |
| 7,238,807 | B2 | 7/2007 | Duran et al. |
| 7,241,889 | B2 | 7/2007 | Hoffmann et al. |
| 7,371,753 | B2 | 5/2008 | Stadtmueller |
| 2004/0029885 | A1 | 2/2004 | Bauer et al. |
| 2004/0176338 | A1 | 9/2004 | Pairet et al. |
| 2004/0176380 | A1 | 9/2004 | Hoffmann et al. |
| 2004/0186292 | A1 | 9/2004 | Wang et al. |
| 2006/0014751 | A1 | 1/2006 | Hoffmann et al. |
| 2006/0035903 | A1 | 2/2006 | Mohr et al. |

(Continued)

FOREIGN PATENT DOCUMENTS

| | | |
|---|---|---|
| EP | 2099796 A1 | 9/2009 |
| WO | WO9940091 A1 | 8/1999 |

(Continued)

OTHER PUBLICATIONS

L.C. Cantley, Science 296:1655-57 (2002).
Jimenez, et al., J. Biol. Chem., 277(44):41556-62 (2002).
C. Brock, et al., J. Cell. Biol., 160(1):89-99 (2003).

(Continued)

*Primary Examiner* — James O Wilson
*Assistant Examiner* — Ebenezer O Sackey
(74) *Attorney, Agent, or Firm* — Matthew J. Russo

(57) ABSTRACT

Disclosed are compounds of Formula 1,

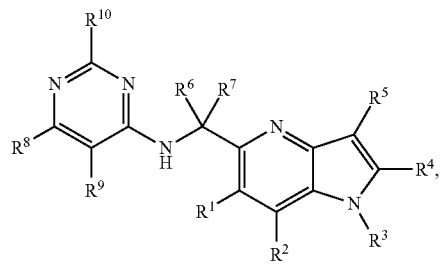

and pharmaceutically acceptable salts thereof, wherein $R^1$, $R^2$, $R^3$, $R^4$, $R^5$, $R^6$, $R^7$, $R^8$, $R^9$, and $R^{10}$ are defined in the specification. This disclosure also relates to materials and methods for preparing compounds of Formula 1, to pharmaceutical compositions which contain them, and to their use for treating immunological disorders, cardiovascular disease, cancer, and other diseases, disorders or conditions associated with PI3Kδ.

35 Claims, No Drawings

(56) References Cited

U.S. PATENT DOCUMENTS

| | | | |
|---|---|---|---|
| 2006/0046990 | A1 | 3/2006 | Stadtmueller et al. |
| 2006/0122393 | A1 | 6/2006 | Duran et al. |
| 2007/0259910 | A1 | 11/2007 | Halley et al. |
| 2008/0177066 | A1 | 7/2008 | Linz et al. |
| 2012/0220575 | A1 | 8/2012 | Chang |

FOREIGN PATENT DOCUMENTS

| | | |
|---|---|---|
| WO | WO/01/81346 | 11/2001 |
| WO | WO/03/035075 | 5/2003 |
| WO | WO/2004/000210 | 12/2003 |
| WO | WO/2005/026175 | 3/2005 |
| WO | WO/2005/063767 | 7/2005 |
| WO | WO/2006/001894 | 1/2006 |
| WO | WO/2006/005915 | 1/2006 |
| WO | WO/2008/023180 A1 | 2/2008 |
| WO | WO/2008/067481 | 6/2008 |
| WO | WO/2008/157179 | 12/2008 |
| WO | WO/2009/023718 | 2/2009 |
| WO | WO/2010/036380 | 4/2010 |
| WO | WO/2010/129467 | 11/2010 |
| WO | WO2010/151735 | 12/2010 |
| WO | WO/2010/151740 | 12/2010 |
| WO | WO/2011/008487 | 1/2011 |

OTHER PUBLICATIONS

B. Vanhaesebroeck, et al., Trends Biochem. Sci. 30:194-204 (2005).
C. Rommel et al., Nature Rev. Immunology, 7:191-201 (2007).
A. Ghigo et al., BioEssays 32:185-196 (2010).
M. Camps et al., Nature Med. 11:936-43 (2005).
G. S. Firestein, N. Engl. J. Med. 354:80-82 (2006).
S. Hayer et al., FASEB J 23:4288-98 (2009) (RA).
D. F. Barber et al., Nature Med. 11:933-35 (2005) (SLE).
A. Fougerat et al., Circulation 117:1310-17. 2008.
T. M. Randis et al., Eur. J. Immunol. 38:1215-24 (2008) (RA).
Lee et al., FASEB J. 20:455-65 (2006).
H. S. Farghaly et al., Mol. Pharmacol. 73:1530-37 (2008).
K. Ali et al., Nature 431:1007-11 (2004).
J. Doukas et al., J. Pharmacol. Exp. Ther. 328:758-65 (2009).
J. Doukas et al., Proc. Nat'l Acad. Sci. USA 103:19866-71 (2006).
Y. Samuels et al., Science 304:554 (2004).
Y. Samuels & K. Ericson, Curr. Opin. Oncol. 18(1):77-82 (2006).
S. Kang et al., Proc. Nat'l Acad. Sci. USA 102(3):802-7 (2005).
A. Bader et al., Proc. Nat'l Acad. Sci. USA 103(5):1475-79 (2006).
P. Sujobert et al., Blood 106(3):1063-66 (2005).
C. Billottet et al., Oncogene 25(50):6648-59 (2006).
F. Hickey & T. Cotter, J. Biol. Chem. 281(5):2441-50 (2006).
C. Benistant et al., Oncogene, 19(44):5083-90 (2000).
M. Mizoguchi et al., Brain Pathology 14(4):372-77 (2004).
C. Knobbe et al, Neuropathology Appl. Neurobiolgy 31(5):486-90 (2005).

AZAINDOLE DERIVATIVES

FIELD OF THE INVENTION

This invention relates to substituted 4-azaindole derivatives and related compounds, which are inhibitors of PI3Kδ, to pharmaceutical compositions which contain them, and to the use of the inhibitors to treat diseases, disorders or conditions associated with PI3Kδ, including immunological disorders, cancer, and cardiovascular disease.

BACKGROUND OF THE INVENTION

The phosphoinositide 3-kinases (PI3Ks) are lipid and protein kinases involved in intracellular signal transduction. They act primarily through phosphorylation of phosphoinositides at the D3 position of the inositol ring, and are typically grouped into three classes (I, II, and III) based on their structure, function, and substrate specificity. The class I PI3Ks, denoted PI3Kα, PI3Kβ, PI3Kγ, and PI3Kδ, catalyze the phosphorylation of phosphatidylinositol-4,5-bisphosphate to phosphatidylinositol-3,4,5-trisphosphate, which functions as a second messenger whose binding to proteins containing pleckstrin homology domains, such as AKT, PDK1, Btk, GTPase activating proteins, and guanine nucleotide exchange factors, triggers a cascade of cellular processes involved with cell growth, survival, proliferation, apoptosis, adhesion, and migration, among others. See L. C. Cantley, *Science* 296:1655-57 (2002). Class I PI3K isoforms exist as heterodimers composed of a catalytic subunit, p110, and an associated regulatory subunit that controls their expression, activation, and subcellular localization. PI3Kα, PI3Kβ, and PI3Kδ associate with a regulatory subunit, p85, and are activated by growth factors and cytokines through a tyrosine kinase-dependent mechanism; PI3Kγ associates with two regulatory subunits, p101 and p84, and is activated by G-protein-coupled receptors. See C. Jimenez, et al., *J. Biol. Chem.*, 277(44):41556-62 (2002) and C. Brock, et al., *J. Cell. Biol.*, 160(1):89-99 (2003).

Although PI3Kα and PI3Kβ are expressed in many tissue types, PI3Kγ and PI3Kδ are predominantly expressed in leukocytes and are therefore thought to be attractive targets for treating inflammatory disorders and other diseases related to the immune system. See B. Vanhaesebroeck, et al., *Trends Biochem. Sci.* 30:194-204 (2005), C. Rommel et al., *Nature Rev. Immunology*, 7:191-201 (2007), and A. Ghigo et al., *BioEssays* 32:185-196 (2010). Recent preclinical studies support this view. For example, treatments with selective PI3Kγ inhibitors suppress the progression of joint inflammation and damage in mouse models of rheumatoid arthritis (RA), and reduce glomerulonephritis and extend survival in the MRL-lpr mouse model of systemic lupus erythematosus (SLE). See M. Camps et al., *Nature Med.* 11:936-43 (2005), G. S. Firestein, *N Engl. J. Med.* 354:80-82 (2006), and S. Hayer et al., *FASEB J* 23:4288-98 (2009) (RA); see also D. F. Barber et al., *Nature Med.* 11:933-35 (2005) (SLE). A selective PI3Kγ inhibitor has also been shown to reduce formation and size of lesions in mouse models of early- and advanced-stage atherosclerosis, and to stabilize plaque formation thereby minimizing risks of plaque rupture and subsequent thrombosis and myocardial infarction. See A. Fougerat et al., *Circulation* 117:1310-17. 2008. Treatments with PI3Kδ-selective inhibitors significantly reduce inflammation and associated bone and cartilage erosion following injection of wild type mice with an arthritogenic serum, attenuate allergic airway inflammation and hyper-responsiveness in a mouse model of asthma, and protect mice against anaphylactic allergic responses. See T. M. Randis et al., *Eur. J. Immunol.* 38:1215-24 (2008) (RA); K. S. Lee et al., *FASEB J.* 20:455-65 (2006) and H. S. Farghaly et al., *Mol. Pharmacol.* 73:1530-37 (2008) (asthma); K. Ali et al., *Nature* 431:1007-11 (2004) (anaphylaxis). Administration of a PI3Kγ and PI3Kδ dual selective inhibitor has been shown to be efficacious in murine models of allergic asthma and chronic obstructive pulmonary disease (COPD) and is cardioprotective in murine and porcine models of myocardial infarction (MI). See J. Doukas et al., *J. Pharmacol. Exp. Ther.* 328:758-65 (2009) (asthma and COPD); J. Doukas et al., *Proc. Nat'l Acad. Sci. USA* 103:19866-71 (2006) (MI).

Studies also suggest targeting one or more of the four class I PI3K isoforms may yield useful treatments for cancer. The gene encoding p110α is mutated frequently in common cancers, including breast, brain, prostate, colon, gastric, lung, and endometrial cancers. See Y. Samuels et al., *Science* 304:554 (2004) and Y. Samuels & K. Ericson, *Curr. Opin. Oncol.* 18(1):77-82 (2006). One of three amino acid substitutions in the helical or kinase domains of the enzyme are responsible for 80 percent of these mutations, which lead to significant up-regulation of kinase activity and result in oncogenic transformation in cell culture and in animal models. See S. Kang et al., *Proc. Nat'l Acad. Sci. USA* 102(3):802-7 (2005) and A. Bader et al., *Proc. Nat'l Acad. Sci. USA* 103(5):1475-79 (2006). No such mutations have been identified in the other PI3K isoforms, though there is evidence they can contribute to the development and progression of malignancies. PI3Kδ is consistently over expressed in acute myeloblastic leukemia and inhibitors of PI3Kδ can prevent the growth of leukemic cells. See P. Sujobert et al., *Blood* 106(3):1063-66 (2005); C. Billottet et al., *Oncogene* 25(50):6648-59 (2006). PI3Kγ expression is elevated in chronic myeloid leukemia. See F. Hickey & T. Cotter, *J. Biol. Chem.* 281(5):2441-50 (2006). Alterations in expression of PI3Kβ, PI3Kγ, and PI3Kδ have also been observed in cancers of the brain, colon and bladder. See C. Benistant et al., *Oncogene,* 19(44):5083-90 (2000), M. Mizoguchi et al., *Brain Pathology* 14(4):372-77 (2004), and C. Knobbe et al, *Neuropathology Appl. Neurobiolgy* 31(5):486-90 (2005). Moreover, all of these isoforms have been shown to be oncogenic in cell culture. See S. Kang et al. (2006).

Certain inhibitors of PI3K are described in U.S. Pat. Nos. 6,518,277, 6,667,300, WO 01/81346, WO 03/035075, WO 2006/005915, WO2008/023180, WO2010/036380, WO2010/151735, WO2010/151740, and WO2011/008487.

SUMMARY OF THE INVENTION

This invention provides substituted 4-azaindole derivatives and related compounds, and pharmaceutically acceptable salts thereof. This invention also provides pharmaceutical compositions that contain the substituted 4-azaindoles and provides for their use to treat diseases, disorders or conditions associated with PI3Kδ inhibition, including immunological disorders, cancer, and cardiovascular disease.

One aspect of the invention provides a compound of Formula 1:

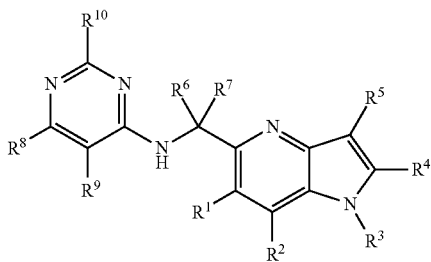

or a pharmaceutically acceptable salt thereof, wherein:

$R^1$ is selected from $C_{3-8}$ cycloalkyl, $C_{2-6}$ heterocyclyl, $C_{6-14}$ aryl, and $C_{1-9}$ heteroaryl, each optionally substituted with from one to five substituents independently selected from halo, oxo, —CN, $R^{11}$, and $R^{12}$;

$R^2$, $R^4$, and $R^5$ are each independently selected from hydrogen, halo, —OH, —CN, $C_{1-3}$ alkyl, and $C_{1-3}$ haloalkyl;

$R^3$ is selected from hydrogen, $C_{1-3}$ alkyl, and $C_{1-3}$ haloalkyl;

$R^6$ and $R^7$ are each independently selected from hydrogen, $C_{1-3}$ alkyl, and $C_{1-3}$ haloalkyl;

$R^8$ is selected from hydrogen, methyl, and —$NH_2$;

$R^9$ is selected from hydrogen, halo, —CN, $C_{1-3}$ haloalkyl, —$OR^{16}$, —$C(O)R^{16}$, —$C(O)OR^{16}$, —$C(O)N(R^{16})R^{17}$, —$C(O)N(R^{16})OR^{17}$, —$C(O)N(R^{16})S(O)_2R^{18}$, $SR^{16}$, —$S(O)R^{18}$, —$S(O)_2R^{18}$, and —$S(O)_2N(R^{16})R^{17}$; or $R^8$ is selected from —NH— and —$CH_2$—, and $R^8$ and $R^9$, together with the carbon atoms to which they are attached, form a $C_{2-4}$ heteroarylene having 5 ring atoms and 1 to 3 heteroatoms, each of the heteroatoms being nitrogen, and wherein the $C_{2-4}$ heteroarylene is optionally substituted with $R^{12}$;

$R^{10}$ is selected from halo, —OH, $C_{1-3}$ alkyl, —$NHR^{16}$, and —$NHC(O)R^{16}$;

each $R^{11}$ is independently selected from –$OR^{13}$, —$N(R^{13})R^{14}$, —$NR^{13}C(O)R^{14}$, —$NHC(O)NR^{13}R^{14}$, —$NR^{13}C(O)NHR^{14}$, —$C(O)R^{13}$, —$C(O)OR^{13}$, —$C(O)N(R^{13})R^{14}$, —$C(O)N(R^{13})OR^{14}$, —$C(O)N(R^{13})S(O)_2R^{12}$, —$N(R^{13})S(O)_2R^{12}$, —$SR^{13}$, —$S(O)R^{12}$, —$S(O)_2R^{12}$, and —$S(O)_2N(R^{13})R^{14}$;

each $R^{12}$ is independently selected from $C_{1-6}$ alkyl, $C_{2-6}$ alkenyl, $C_{2-6}$ alkynyl, $C_{3-8}$ cycloalkyl-$(CH_2)_m$—, $C_{6-14}$ aryl-$(CH_2)_m$—, $C_{2-6}$ heterocyclyl-$(CH_2)_m$—, and $C_{1-9}$ heteroaryl-$(CH_2)_m$—, each optionally substituted with from one to five substituents independently selected from halo, oxo, —CN, $C_{1-6}$ alkyl, $C_{1-6}$ haloalkyl, and $R^{15}$;

each $R^{13}$ and $R^{14}$ is independently selected from
(a) hydrogen; and
(b) $C_{1-6}$ alkyl, $C_{2-6}$ alkenyl, $C_{2-6}$ alkynyl, $C_{3-6}$ cycloalkyl-$(CH_2)_m$—, $C_{6-14}$ aryl-$(CH_2)_m$—, $C_{2-6}$ heterocyclyl-$(CH_2)_m$—, and $C_{1-9}$ heteroaryl-$(CH_2)_m$—, each optionally substituted with from one to five substituents independently selected from halo, oxo, —CN, $C_{1-6}$ alkyl, $C_{1-6}$ haloalkyl, and $R^{15}$;

each $R^{15}$ is independently selected from –$OR^{16}$, —$N(R^{16})R^{17}$, —$N(R^{16})C(O)R^{17}$, —$NHC(O)NR^{16}R^{12}$, —$NR^{16}C(O)NHR^{12}$, —$C(O)R^{16}$, —$C(O)OR^{16}$, —$C(O)N(R^{16})R^{17}$, —$C(O)N(R^{16})OR^{12}$, —$C(O)N(R^{16})S(O)_2R^{18}$, —$NR^{16}S(O)_2R^{18}$, —$SR^{16}$, —$S(O)R^{18}$, —$S(O)_2R^{18}$, and —$S(O)_2N(R^{16})R^{17}$;

each $R^{16}$ and $R^{17}$ is independently selected from hydrogen, $C_{1-6}$ alkyl, and $C_{3-6}$ cycloalkyl;

each $R^{18}$ is independently selected from $C_{1-6}$ alkyl and $C_{3-6}$ cycloalkyl;

each m is independently selected from 0, 1, 2, 3, and 4;

wherein each of the aforementioned heteroaryl moieties independently has 1 to 4 heteroatoms independently selected from N, O, and S, and each of the aforementioned heterocyclyl moieties independently has 1 to 4 heteroatoms independently selected from N, O, and S.

Another aspect of the invention provides a compound of Formula 1 as defined above, which is selected from the compounds described in the examples, their pharmaceutically acceptable salts, and stereoisomers of any of the compounds in the examples and their pharmaceutically acceptable salts.

A further aspect of the invention provides a pharmaceutical composition which includes a compound of Formula 1 or a pharmaceutically acceptable salt thereof as defined above, and a pharmaceutically acceptable excipient.

An additional aspect of the invention provides a compound of Formula 1 or a pharmaceutically acceptable salt thereof as defined above for use as a medicament.

Another aspect of the invention provides a compound of Formula 1 or a pharmaceutically acceptable salt thereof as defined above for use in the manufacture of a medicament for the treatment of a condition associated with PI3Kδ.

A further aspect of the invention provides a method of treating a disease, disorder or condition associated with PI3Kδ in a subject, the method comprising administering to the subject an effective amount of a compound of Formula 1 or a pharmaceutically acceptable salt thereof as defined above.

An additional aspect of the invention provides a method of treating a disease, disorder or condition in a subject, the method comprising administering to the subject an effective amount of a compound of Formula 1 or a pharmaceutically acceptable salt thereof as defined above, wherein the disease, disorder or condition is selected from immunological disorders, cancer, and cardiovascular disease.

Another aspect of the invention provides a method of treating a disease, disorder or condition in a subject, the method comprising administering to the subject an effective amount of a compound of Formula 1 or a pharmaceutically acceptable salt thereof as defined above, wherein the disease, disorder or condition is selected from allergic rhinitis, asthma, atopic dermatitis, rheumatoid arthritis, multiple sclerosis, systemic lupus erythematosus, psoriasis, immune thrombocytopenic purpura, inflammatory bowel disease, behcet's disease, graft-versus-host disease (GVHD), chronic obstructive pulmonary disease, atherosclerosis, myocardial infarction, and thrombosis.

Another aspect of the invention provides a method of treating a disease, disorder or condition in a subject, the method comprising administering to the subject an effective amount of a compound of Formula 1 or a pharmaceutically acceptable salt thereof as defined above, wherein the disease or condition is selected from brain cancer, lung cancer, squamous cell cancer, bladder cancer, gastric cancer, pancreatic cancer, breast cancer, cancer of the head, neck cancer, renal cancer, kidney cancer, ovarian cancer, prostate cancer, colorectal cancer, prostate cancer, colon cancer, epidermoid cancer, esophageal cancer, testicular cancer, gynecological cancer, and thyroid cancer.

A further aspect of the invention provides a combination of an effective amount of a compound of Formula 1 or a pharmaceutically acceptable salt thereof as defined above, and at least one additional pharmacologically active agent.

An additional aspect of the invention provides a method of making a compound of Formula 1 or a pharmaceutically acceptable salt thereof as defined in claim 1, the method comprising:

reacting a compound of Formula F 1,

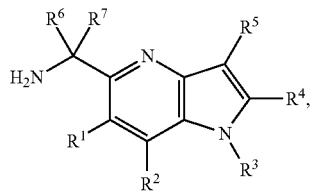

or a salt thereof, in the presence of a base, to give a compound of Formula 1 or a salt thereof in which $R^8$ is —$NH_2$, $R^9$ is —CN, and $R^{10}$ is selected from —OH, $C_{1-3}$ alkyl, and —$NHR^{16}$; and optionally converting the compound of Formula 1 to a pharmaceutically acceptable salt;

wherein $R^1$, $R^2$, $R^3$, $R^4$, $R^5$, $R^6$, $R^7$, and $R^{16}$ are defined as for Formula 1.

DETAILED DESCRIPTION OF THE INVENTION

Unless otherwise indicated, this disclosure uses definitions provided below.

"Substituted," when used in connection with a chemical substituent or moiety (e.g., a $C_{1-6}$ alkyl group), means that one or more hydrogen atoms of the substituent or moiety have been replaced with one or more non-hydrogen atoms or groups, provided that valence requirements are met and that a chemically stable compound results from the substitution.

"About" or "approximately," when used in connection with a measurable numerical variable, refers to the indicated value of the variable and to all values of the variable that are within the experimental error of the indicated value or within ±10 percent of the indicated value, whichever is greater.

"Alkyl" refers to straight chain and branched saturated hydrocarbon groups, generally having a specified number of carbon atoms (e.g., $C_{1-3}$ alkyl refers to an alkyl group having 1 to 3 (i.e., 1, 2 or 3) carbon atoms, $C_{1-6}$ alkyl refers to an alkyl group having 1 to 6 carbon atoms, and so on). Examples of alkyl groups include methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, and the like.

"Alkenyl" refers to straight chain and branched hydrocarbon groups having one or more carbon-carbon double bonds, and generally having a specified number of carbon atoms. Examples of alkenyl groups include ethenyl, 1-propen-1-yl, 1-propen-2-yl, 2-propen-1-yl, 1-buten-1-yl, 1-buten-2-yl, 3-buten-1-yl, 3-buten-2-yl, 2-buten-1-yl, 2-buten-2-yl, 2-methyl-1-propen-1-yl, 2-methyl-2-propen-1-yl, 1,3-butadien-1-yl, 1,3-butadien-2-yl, and the like.

"Alkynyl" refers to straight chain or branched hydrocarbon groups having one or more triple carbon-carbon bonds, and generally having a specified number of carbon atoms. Examples of alkynyl groups include ethynyl, 1-propyn-1-yl, 2-propyn-1-yl, 1-butyn-1-yl, 3-butyn-1-yl, 3-butyn-2-yl, 2-butyn-1-yl, and the like.

"Halo," "halogen" and "halogeno" may be used interchangeably and refer to fluoro, chloro, bromo, and iodo.

"Haloalkyl," "haloalkenyl," and "haloalkynyl," refer, respectively, to alkyl, alkenyl, and alkynyl groups substituted with one or more halogen atoms, where alkyl, alkenyl, and alkynyl are defined above, and generally having a specified number of carbon atoms. Examples of haloalkyl groups include fluoromethyl, difluoromethyl, trifluoromethyl, chloromethyl, dichloromethyl, trichloromethyl, and the like.

"Cycloalkyl" refers to saturated monocyclic and bicyclic hydrocarbon groups, generally having a specified number of carbon atoms that comprise the ring or rings (e.g., $C_{3-8}$ cycloalkyl refers to a cycloalkyl group having 3 to 8 carbon atoms as ring members). Bicyclic hydrocarbon groups may include isolated rings (two rings sharing no carbon atoms), spiro rings (two rings sharing one carbon atom), fused rings (two rings sharing two carbon atoms and the bond between the two common carbon atoms), and bridged rings (two rings sharing two carbon atoms, but not a common bond). The cycloalkyl group may be attached through any ring atom unless such attachment would violate valence requirements. In addition, the cycloalkyl group may include one or more non-hydrogen substituents unless such substitution would violate valence requirements.

Examples of monocyclic cycloalkyl groups include cyclopropyl, cyclobutyl, cyclopentyl, cyclohexyl, and the like. Examples of fused bicyclic cycloalkyl groups include bicyclo[2.1.0]pentanyl (i.e., bicyclo[2.1.0]pentan-1-yl, bicyclo[2.1.0]pentan-2-yl, and bicyclo[2.1.0]pentan-5-yl), bicyclo[3.1.0]hexanyl, bicyclo[3.2.0]heptanyl, bicyclo[4.1.0]heptanyl, bicyclo[3.3.0]octanyl, bicyclo[4.2.0]octanyl, bicyclo[4.3.0]nonanyl, bicyclo[4.4.0]decanyl, and the like. Examples of bridged cycloalkyl groups include bicyclo[2.1.1]hexanyl, bicyclo[2.2.1]heptanyl, bicyclo[3.1.1]heptanyl, bicyclo[2.2.2]octanyl, bicyclo[3.2.1]octanyl, bicyclo[4.1.1]octanyl, bicyclo[3.3.1]nonanyl, bicyclo[4.2.1]nonanyl, bicyclo[3.3.2]decanyl, bicyclo[4.2.2]decanyl, bicyclo[4.3.1]decanyl, bicyclo[3.3.3]undecanyl, bicyclo[4.3.2]undecanyl, bicyclo[4.3.3]dodecanyl, and the like. Examples of spiro cycloalkyl groups include spiro[3.3]heptanyl, spiro[2.4]heptanyl, spiro[3.4]octanyl, spiro[2.5]octanyl, spiro[3.5]nonanyl, and the like. Examples of isolated bicyclic cycloalkyl groups include those derived from bi(cyclobutane), cyclobutanecyclopentane, bi(cyclopentane), cyclobutanecyclohexane, cyclopentanecyclohexane, bi(cyclohexane), etc.

"Cycloalkylidene" refers to divalent monocyclic cycloalkyl groups, where cycloalkyl is defined above, which are attached through a single carbon atom of the group, and generally having a specified number of carbon atoms that comprise the ring (e.g., $C_{3-6}$ cycloalkylidene refers to a cycloalkylidene group having 3 to 6 carbon atoms as ring members). Examples include cyclopropylidene, cyclobutylidene, cyclopentylidene, and cyclohexylidene.

"Cycloalkenyl" refers to partially unsaturated monocyclic and bicyclic hydrocarbon groups, generally having a specified number of carbon atoms that comprise the ring or rings. As with cycloalkyl groups, the bicyclic cycloalkenyl groups may include isolated, spiro, fused, or bridged rings. Similarly, the cycloalkenyl group may be attached through any ring atom and may include one or more non-hydrogen substituents unless such attachment or substitution would violate valence requirements. Examples of cycloalkenyl groups include the partially unsaturated analogs of the cycloalkyl groups described above, such as cyclobutenyl (i.e., cyclobuten-1-yl and cyclobuten-3-yl), cyclopentenyl, cyclohexenyl, bicyclo[2.2.1]hept-2-enyl, and the like.

"Aryl" refers to fully unsaturated monocyclic aromatic hydrocarbons and to polycyclic hydrocarbons having at least one aromatic ring, both monocyclic and polycyclic aryl groups generally having a specified number of carbon atoms that comprise their ring members (e.g., $C_{6-14}$ aryl refers to an aryl group having 6 to 14 carbon atoms as ring members). The group may be attached through any ring atom and may include one or more non-hydrogen substituents unless such attachment or substitution would violate valence requirements. Examples of aryl groups include phenyl, biphenyl, cyclobutabenzenyl, indenyl, naphthalenyl, benzocycloheptanyl, biphenylenyl, fluorenyl, groups derived from cycloheptatriene cation, and the like.

"Arylene" refers to divalent aryl groups, where aryl is defined above. Examples of arylene groups include phenylene (i.e., benzene-1,2-diyl).

"Heterocycle" and "heterocyclyl" may be used interchangeably and refer to saturated or partially unsaturated monocyclic or bicyclic groups having ring atoms composed of carbon atoms and 1 to 4 heteroatoms independently selected from nitrogen, oxygen, and sulfur. Both the monocyclic and bicyclic groups generally have a specified number of carbon atoms in their ring or rings (e.g., $C_{2-6}$ heterocyclyl refers to a heterocyclyl group having 2 to 6 carbon atoms and 1 to 4 heteroatoms as ring members). As with bicyclic cycloalkyl groups, bicyclic heterocyclyl groups may include isolated rings, spiro rings, fused rings, and bridged rings. The heterocyclyl group may be attached through any ring atom and may include one or more non-hydrogen substituents unless such attachment or substitution would violate valence requirements or result in a chemically unstable compound. Examples of monocyclic heterocyclyl groups include oxiranyl, thiiranyl, aziridinyl (e.g., aziridin-1-yl and aziridin-2-yl), oxetanyl, thietanyl, azetidinyl, tetrahydrofuranyl, tetrahydrothiopheneyl, pyrrolidinyl, tetrahydropyranyl, tetrahydrothiopyranyl, piperidinyl, 1,4-dioxanyl, 1,4-oxathianyl, morpholinyl, 1,4-dithianyl, piperazinyl, 1,4-azathianyl, oxepanyl, thiepanyl, azepanyl, 1,4-dioxepanyl, 1,4-oxathiepanyl, 1,4-oxaazepanyl, 1,4-dithiepanyl, 1,4-thiazepanyl, 1,4-diazepanyl, 3,4-dihydro-2H-pyranyl, 3,6-dihydro-2H-pyranyl, 2H-pyranyl, 1,2-dihydropyridine, 1,2,3,4-tetrahydropyridinyl, and 1,2,5,6-tetrahydropyridinyl.

"Heterocycle-diyl" refers to heterocyclyl groups which are attached through two ring atoms of the group, where heterocyclyl is defined above. They generally have a specified number of carbon atoms in their ring or rings (e.g., $C_{2-6}$ heterocycle-diyl refers to a heterocycle-diyl group having 2 to 6 carbon atoms and 1 to 4 heteroatoms as ring members). Examples of heterocycle-diyl groups include the multivalent analogs of the heterocycle groups described above, such as morpholine-3,4-diyl, pyrrolidine-1,2-diyl, 1-pyrrolidinyl-2-ylidene, 1-pyridinyl-2-ylidene, 1-(4H)-pyrazolyl-5-ylidene, 1-(3H)-imidazolyl-2-ylidene, 3-oxazolyl-2-ylidene, 1-piperidinyl-2-ylidene, 1-piperazinyl-6-ylidene, and the like.

"Heteroaromatic" and "heteroaryl" may be used interchangeably and refer to unsaturated monocyclic aromatic groups and to polycyclic groups having at least one aromatic ring, each of the groups having ring atoms composed of carbon atoms and 1 to 4 heteroatoms independently selected from nitrogen, oxygen, and sulfur. Both the monocyclic and polycyclic groups generally have a specified number of carbon atoms as ring members (e.g., $C_{1-9}$ heteroaryl refers to a heteroaryl group having 1 to 9 carbon atoms and 1 to 4 heteroatoms as ring members) and may include any bicyclic group in which any of the above-listed monocyclic heterocycles are fused to a benzene ring. The heteroaryl group may be attached through any ring atom (or ring atoms for fused rings) and may include one or more non-hydrogen substituents unless such attachment or substitution would violate valence requirements or result in a chemically unstable compound. Examples of heteroaryl groups include monocyclic groups such as pyrrolyl (e.g., pyrrol-1-yl, pyrrol-2-yl, and pyrrol-3-yl), furanyl, thiopheneyl, pyrazolyl, imidazolyl, isoxazolyl, oxazolyl, isothiazolyl, thiazolyl, 1,2,3-triazolyl, 1,3,4-triazolyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, tetrazolyl, pyridinyl, pyridazinyl, pyrimidinyl, and pyrazinyl.

Examples of heteroaryl groups also include bicyclic groups such as benzofuranyl, isobenzofuranyl, benzothiopheneyl, benzo[c]thiopheneyl, indolyl, 3H-indolyl, isoindolyl, 1H-isoindolyl, indolinyl, isoindolinyl, benzimidazolyl, indazolyl, benzotriazolyl, 1H-pyrrolo[2,3-b]pyridinyl, 1H-pyrrolo[2,3-c]pyridinyl, 1H-pyrrolo[3,2-c]pyridinyl, 1H-pyrrolo[3,2-b]pyridinyl, 3H-imidazo[4,5-b]pyridinyl, 3H-imidazo[4,5-c]pyridinyl, 1H-pyrazolo[4,3-b]pyridinyl, 1H-pyrazolo[4,3-c]pyridinyl, 1H-pyrazolo[3,4-c]pyridinyl, 1H-pyrazolo[3,4-b]pyridinyl, 7H-purinyl, indolizinyl, imidazo[1,2-c]pyridinyl, imidazo[1,5-a]pyridinyl, pyrazolo[1,5-c]pyridinyl, pyrrolo[1,2-b]pyridazinyl, imidazo[1,2-c]pyrimidinyl, quinolinyl, isoquinolinyl, cinnolinyl, quinazolinyl, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl, and pyrimido[4,5-d]pyrimidinyl.

"Heteroarylene" refers to heteroaryl groups which are attached through two ring atoms of the group, where heteroaryl is defined above. They generally have a specified number of carbon atoms in their ring or rings (e.g., $C_{3-5}$ heteroarylene refers to a heteroarylene group having 3 to 5 carbon atoms and 1 to 4 heteroatoms as ring members). Examples of heteroarylene groups include the multivalent analogs of the heteroaryl groups described above, such as pyridin-2,3-diyl, pyridin-3,4-diyl, 1H-imidazol-4,5-diyl, 1H-pyrazol-4,5-diyl, 1H-pyrazol-3,4-diyl, 1H-triazol-4,5-diyl, and the like.

"Oxo" refers to a double bonded oxygen (=O).

"Leaving group" refers to any group that leaves a molecule during a fragmentation process, including substitution reactions, elimination reactions, and addition-elimination reactions. Leaving groups may be nucleofugal, in which the group leaves with a pair of electrons that formerly served as the bond between the leaving group and the molecule, or may be electrofugal, in which the group leaves without the pair of electrons. The ability of a nucleofugal leaving group to leave depends on its base strength, with the strongest bases being the poorest leaving groups. Common nucleofugal leaving groups include nitrogen (e.g., from diazonium salts); sulfonates, including alkylsulfonates (e.g., mesylate), fluoroalkylsulfonates (e.g., triflate, hexaflate, nonaflate, and tresylate), and arylsulfonates (e.g., tosylate, brosylate, closylate, and nosylate). Others include carbonates, halide ions, carboxylate anions, phenolate ions, and alkoxides. Some stronger bases, such as $NH_2$ and $OH^-$ can be made better leaving groups by treatment with an acid. Common electrofugal leaving groups include the proton, $CO_2$, and metals.

"Opposite enantiomer" refers to a molecule that is a non-superimposable mirror image of a reference molecule, which may be obtained by inverting all of the stereogenic centers of the reference molecule. For example, if the reference molecule has S absolute stereochemical configuration, then the opposite enantiomer has R absolute stereochemical configuration. Likewise, if the reference molecule has S,S absolute stereochemical configuration, then the opposite enantiomer has R,R stereochemical configuration, and so on.

"Stereoisomer" and "stereoisomers" of a compound with given stereochemical configuration refer to the opposite enantiomer of the compound and to any diastereoisomers, including geometrical isomers (Z/E) of the compound. For example, if a compound has S,R,Z stereochemical configuration, its stereoisomers would include its opposite enantiomer having R,S,Z configuration, and its diastereomers having S,S,Z configuration, R,R,Z configuration, S,R,E configuration, R,S,E configuration, S,S,E configuration, and R,R,E configuration. If the stereochemical configuration of a compound is not specified, then "stereoisomer" refers to any one of the possible stereochemical configurations of the compound.

"Substantially pure stereoisomer" and variants thereof refer to a sample containing a compound having a specific stereochemical configuration and which comprises at least about 95% of the sample.

"Pure stereoisomer" and variants thereof refer to a sample containing a compound having a specific stereochemical configuration and which comprises at least about 99.5% of the sample.

"Subject" refers to a mammal, including a human.

"Pharmaceutically acceptable" substances refer to those substances which are suitable for administration to subjects.

"Treating" refers to reversing, alleviating, inhibiting the progress of, or preventing a disease, disorder or condition to which such term applies, or to reversing, alleviating, inhibiting the progress of, or preventing one or more symptoms of such disease, disorder or condition.

"Treatment" refers to the act of "treating," as defined immediately above.

"Drug," "drug substance," "active pharmaceutical ingredient," and the like, refer to a compound (e.g., compounds of Formula 1, including subgeneric compounds and compounds specifically named in the specification) that may be used for treating a subject in need of treatment.

"Effective amount" of a drug, "therapeutically effective amount" of a drug, and the like, refer to the quantity of the drug that may be used for treating a subject and may depend on the weight and age of the subject and the route of administration, among other things.

"Excipient" refers to any diluent or vehicle for a drug.

"Pharmaceutical composition" refers to the combination of one or more drug substances and one or more excipients.

"Drug product," "pharmaceutical dosage form," "dosage form," "final dosage form" and the like, refer to a pharmaceutical composition suitable for treating a subject in need of treatment and generally may be in the form of tablets, capsules, sachets containing powder or granules, liquid solutions or suspensions, patches, films, and the like.

"Condition associated with PI3Kδ" and similar phrases relate to a disease, disorder or condition in a subject for which inhibition of PI3Kδ may provide a therapeutic or prophylactic benefit.

The following abbreviations are used throughout the specification: Ac (acetyl); ACN (acetonitrile); AIBN (azo-bis-isobutyronitrile); API (active pharmaceutical ingredient); aq (aqueous); Boc (tert-butoxycarbonyl); Cbz (carbobenzyloxy); dba (dibenzylideneacetone); DCC (1,3-dicyclohexyl-carbodiimide); DCE (1,1-dichloroethane); DCM (dichloromethane); DIPEA (N,N-diisopropylethylamine, Hünig's Base); DMA (N,N-dimethylacetamide); DMAP (4-dimethylaminopyridine); DMARD (disease modifying antirheumatic drug); DME (1,2-dimethoxyethane); DMF (N,N-dimethylformamide); DMPU (1,3-dimethyl-3,4,5,6-tetrahydro-2 (1H)-pyrimidinone; DMSO (dimethylsulfoxide); dppf (1,1'-bis(diphenylphosphino)ferrocene); DTT (dithiothreitol); EDA (ethoxylated dodecyl alcohol, Brij®35); EDC (N-(3-dimethylaminopropyl)-N'-ethylcarbodiimide); EDTA (ethylenediaminetetraacetic acid); ee (enantiomeric excess); eq (equivalents); Et (ethyl); Et$_3$N (triethyl-amine); EtOAc (ethyl acetate); EtOH (ethanol); HATU (2-(3H-[1,2,3]triazolo[4,5-b]pyridin-3-yl)-1,1,3,3-tetramethyluronium hexafluorophosphate(V)); HEPES (4-(2-hydroxyethyl)piperazine-1-ethanesulfonic acid); HOAc (acetic acid); HOBt (1H-benzo[d][1,2,3]triazol-1-ol); IC$_{50}$ (concentration at 50% inhibition); IPA (isopropanol); IPAc (isopropyl acetate); IPE (isopropylether); KOt-Bu (potassium tertiary butoxide); LDA (lithium diisopropylamide); LiHMDS (lithium bis(trimethylsilyl)amide); mCPBA (m-chloroperoxybenzoic acid); Me (methyl); MeOH (methanol); MTBE (methyl tert-butyl ether); mp (melting point); NaOt-Bu (sodium tertiary butoxide); NMM (N-methylmorpholine); NMP (N-methyl-2-pyrrolidone); PE (petroleum ether); Ph (phenyl); pIC$_{50}$ ($-\log_{10}$ (IC$_{50}$), where IC$_{50}$ is given in molar (M) units); Pr (propyl); i-Pr (isopropyl); PTFE (polytetrafluoroethylene); RT (room temperature, approximately 20° C. to 25° C.); TCEP (tris(2-carboxyethyl)phosphine); TFA (trifluoroacetic acid); TFAA (2,2,2-trifluoroacetic anhydride); THF (tetrahydrofuran); TMS (trimethylsilyl); and Tris buffer (2-amino-2-hydroxymethyl-propane-1,3-diol buffer).

As described, below, this disclosure concerns compounds of Formula 1 and their pharmaceutically acceptable salts. This disclosure also concerns materials and methods for preparing compounds of Formula 1, pharmaceutical compositions which contain them, and the use of compounds of Formula 1 and their pharmaceutically acceptable salts (optionally in combination with other pharmacologically active agents) for treating immunological disorders, cancer, cardiovascular disorders, and conditions associated with PI3Kδ and optionally other PI3K isoforms.

In addition to the specific compounds in the examples, compounds of Formula 1 include those in which: (a) $R^1$ is selected from cyclopropyl, azetidinyl, pyrrolidinyl, cyclohexyl, piperidinyl, morpholinyl, piperazinyl, tetrahydropyranyl, 3,6-dihydro-2H-pyranyl, 1,4-oxazepanyl, 2-oxa-6-aza-spiro[3.3]heptanyl, furanyl, pyrrolyl, pyrazolyl, imidazolyl, thiazolyl, isoxazolyl, phenyl, pyridinyl, 1,2-dihydropyridinyl, and pyrimidinyl, each optionally substituted with from one to five substituents independently selected from halo, oxo, —CN, $R^{11}$, and $R^{12}$; (b) $R^2$, $R^4$, and $R^5$ are each independently selected from hydrogen and halo; (c) at least one of $R^6$ and $R^7$ is hydrogen; (d) at least one of $R^6$ and $R^7$ is $C_{1-3}$ alkyl; or any combination of structural features (a) through (d).

In addition, or as an alternative, to one or more of embodiments (b) through (d) in the preceding paragraph, compounds of Formula 1 include those in which: (e) $R^1$ is selected from azetidin-1-yl, piperidin-1-yl, morpholin-4-yl, tetrahydro-2H-pyran-4-yl, 2-oxa-6-azaspiro[3.3]heptan-6-yl, 1H-pyrazol-4-yl, 1H-pyrazol-5-yl, thiazol-4-yl, isoxazol-4-yl, pyridin-2-yl, and pyridin-4-yl, each optionally substituted with from one to five substituents independently selected from halo, oxo, —CN, $R^{11}$, and $R^{12}$.

In addition, or as an alternative, to one or more of embodiments (b) through (d) in the preceding paragraph, compounds of Formula 1 include those in which: (f) $R^1$ is selected from pyridinyl, morpholinyl, and pyrazolyl, each optionally substituted with from one to five substituents independently selected from halo, oxo, —CN, $R^{11}$, and $R^{12}$.

In addition, or as an alternative, to one or more of embodiments (b) through (d) in the preceding paragraph, compounds of Formula 1 include those in which: (g) $R^1$ is pyridinyl optionally substituted with from one to four substituents independently selected from halo, —CN, $R^{11}$, and $R^{12}$ or from one to four substituents independently selected from halo, hydroxy, —CN, $C_{1-3}$ alkyl, and $C_{1-3}$ haloalkyl or from one to three substituents independently selected from fluoro, hydroxy, oxo, —CN, methyl, and difluoromethyl.

In addition, or as an alternative, to one or more of embodiments (b) through (d) in the preceding paragraph, compounds of Formula 1 include those in which: (h) $R^1$ is morpholinyl optionally substituted with from one to five substituents independently selected from halo, oxo, —CN, $R^{11}$, and $R^{12}$ or from halo, hydroxy, oxo, —CN, $C_{1-3}$ alkyl, and $C_{1-3}$ haloalkyl or from fluoro, hydroxy, oxo, —CN, methyl, and difluoromethyl.

In addition, or as an alternative, to one or more of embodiments (b) through (d) in the preceding paragraph, compounds of Formula 1 include those in which: (i) $R^1$ is pyrazolyl optionally substituted with from one to three substituents independently selected from halo (on carbon), —CN, $R^{11}$, and $R^{12}$ or from halo (on carbon), hydroxy, —CN, $C_{1-3}$ alkyl, and $C_{1-3}$ haloalkyl or from fluoro (on carbon), hydroxy, —CN, methyl, and difluoromethyl.

In addition, or as an alternative, to one or more of embodiments (a) through (f) in the preceding paragraphs, compounds of Formula 1 include those in which: (j) $R^1$ is optionally substituted with from one to three substituents independently selected from halo, hydroxy, oxo, —CN, $C_{1-3}$ alkyl, and $C_{1-3}$ haloalkyl.

In addition, or as an alternative, to one or more of embodiments (a) through (f) in the preceding paragraphs, compounds of Formula 1 include those in which: (k) $R^1$ is optionally substituted with from one to three substituents independently selected from fluoro, hydroxy, oxo, —CN, methyl, and difluoromethyl.

In addition, or as an alternative, to one or more of embodiments (a) through (i) in the preceding paragraphs, compounds of Formula 1 include those in which: (l) $R^1$ is unsubstituted (i.e., contains no optional substituents).

In addition, or as an alternative, to one or more of embodiments (a) through (l) in the preceding paragraphs, compounds of Formula 1 include those in which: (m) $R^2$, $R^4$, and $R^5$ are each independently selected from hydrogen and halo and at most one of $R^2$, $R^4$, and $R^5$ is halo.

In addition, or as an alternative, to one or more of embodiments (a) through (m) in the preceding paragraphs, compounds of Formula 1 include those in which: (n) $R^2$, $R^4$, and $R^5$ are each independently selected from hydrogen and fluoro.

In addition, or as an alternative, to one or more of embodiments (a) through (n) in the preceding paragraphs, compounds of Formula 1 include those in which: (o) $R^3$ is $C_{1-3}$ alkyl or $C_{1-3}$ haloalkyl.

In addition, or as an alternative, to one or more of embodiments (a) through (n) in the preceding paragraphs, compounds of Formula 1 include those in which: (p) $R^3$ is methyl.

In addition, or as an alternative, to one or more of embodiments (a) through (p) in the preceding paragraphs, compounds of Formula 1 include those in which: (q) one of $R^6$ and $R^7$ is hydrogen and one of $R^6$ and $R^7$ is $C_{1-3}$ alkyl.

In addition, or as an alternative, to one or more of embodiments (a) through (p) in the preceding paragraphs, compounds of Formula 1 include those in which: (r) one of $R^6$ and $R^7$ is hydrogen and one of $R^6$ and $R^7$ is methyl or ethyl.

In addition, or as an alternative, to one or more of embodiments (a) through (p) in the preceding paragraphs, compounds of Formula 1 include those in which: (s) one of $R^6$ and $R^7$ is hydrogen and one of $R^6$ and $R^7$ is methyl.

In addition, or as an alternative, to one or more of embodiments (a) through (s) in the preceding paragraphs, compounds of Formula 1 include those in which: (t) $R^8$ is —NH$_2$ or methyl, and $R^9$ is selected from halo, —CN, and $C_{1-3}$ haloalkyl.

In addition, or as an alternative, to one or more of embodiments (a) through (s) in the preceding paragraphs, compounds of Formula 1 include those in which: (u) $R^8$ is —NH$_2$ or methyl, and $R^9$ is —CN.

In addition, or as an alternative, to one or more of embodiments (a) through (s) in the preceding paragraphs, compounds of Formula 1 include those in which: (v) $R^8$ is —NH—, and $R^8$ and $R^9$, together with the carbon atoms to which they are attached, form a 1H-imidazol-4,5-diyl or 1H-pyrazol-4,5-diyl.

In addition, or as an alternative, to one or more of embodiments (a) through (v) in the preceding paragraphs, compounds of Formula 1 include those in which: (w) $R^{10}$ is —NH$_2$.

In addition, or as an alternative, to one or more of embodiments (a) through (w) in the preceding paragraphs, compounds of Formula 1 include those in which: (x) m is 0.

If (y) $R^6$ and $R^7$ are different, then compounds of Formula 1 include those having stereochemical configuration given by Formula 1A or Formula 1B:

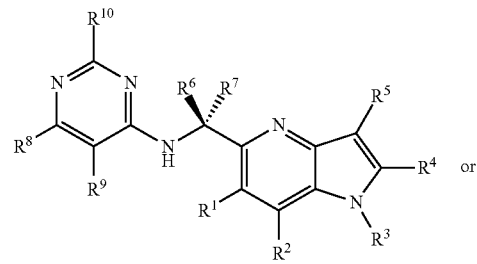

1A

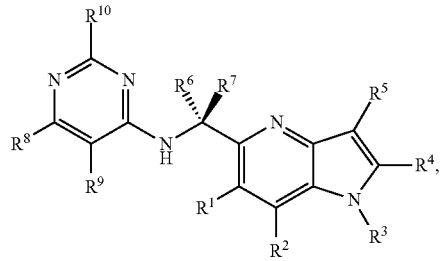

1B wherein $R^1$, $R^2$, $R^3$, $R^4$, $R^5$, $R^6$, $R^7$, $R^8$, $R^9$, and $R^{10}$ in Formula 1A and Formula 1B are as defined for Formula 1 or as defined in one or more of embodiments (a) through (x) in the preceding paragraphs.

Compounds of Formula 1 and pharmaceutically acceptable salts thereof include embodiments (a) through (y) described in the preceding paragraphs and all compounds specifically named in the examples.

Compounds of Formula 1 may form pharmaceutically acceptable complexes, salts, solvates and hydrates. These salts include acid addition salts (including di-acids) and base salts. Pharmaceutically acceptable acid addition salts include salts derived from inorganic acids such as hydrochloric acid, nitric acid, phosphoric acid, sulfuric acid, hydrobromic acid, hydroiodic acid, hydrofluoric acid, and phosphorous acids, as well nontoxic salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts include acetate, adipate, aspartate, benzoate, besylate, bicarbonate, carbonate, bisulfate, sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate, hydrogen phosphate, dihydrogen phosphate, pyroglutamate, saccharate, stearate, succinate, tannate, tartrate, tosylate, trifluoroacetate and xinofoate salts.

Pharmaceutically acceptable base salts include salts derived from bases, including metal cations, such as an alkali or alkaline earth metal cation, as well as amines Examples of suitable metal cations include sodium, potassium, magnesium, calcium, zinc, and aluminum. Examples of suitable amines include arginine, N,N'-dibenzylethylenediamine, chloroprocaine, choline, diethylamine, diethanolamine, dicyclohexylamine, ethylenediamine, glycine, lysine, N-methylglucamine, olamine, 2-amino-2-hydroxymethyl-propane-1, 3-diol, and procaine. For a discussion of useful acid addition and base salts, see S. M. Berge et al., *J. Pharm. Sci.* (1977) 66:1-19; see also Stahl and Wermuth, *Handbook of Pharmaceutical Salts: Properties, Selection, and Use* (2002).

Pharmaceutically acceptable salts may be prepared using various methods. For example, a compound of Formula 1 may be reacted with an appropriate acid or base to give the desired salt. Alternatively, a precursor of the compound of Formula 1 may be reacted with an acid or base to remove an acid- or base-labile protecting group or to open a lactone or lactam group of the precursor. Additionally, a salt of the compound of Formula 1 may be converted to another salt through treatment with an appropriate acid or base or through contact with an ion exchange resin. Following reaction, the salt may be isolated by filtration if it precipitates from solution, or by evaporation to recover the salt. The degree of ionization of the salt may vary from completely ionized to almost non-ionized.

Compounds of Formula 1 may exist in a continuum of solid states ranging from fully amorphous to fully crystalline. The term "amorphous" refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ("glass transition"). The term "crystalline" refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ("melting point").

Compounds of Formula 1 may also exist in unsolvated and solvated forms. The term "solvate" describes a molecular complex comprising the compound and one or more pharmaceutically acceptable solvent molecules (e.g., ethanol, isopropanol, etc.). The term "hydrate" is a solvate in which the solvent is water. Pharmaceutically acceptable solvates include those in which the solvent may be isotopically substituted (e.g., $D_2O$, acetone-$d_6$, DMSO-$d_6$).

A currently accepted classification system for solvates and hydrates of organic compounds is one that distinguishes between isolated site, channel, and metal-ion coordinated solvates and hydrates. See, e.g., K. R. Morris (H. G. Brittain ed.) *Polymorphism in Pharmaceutical Solids* (1995). Isolated site solvates and hydrates are ones in which the solvent (e.g., water) molecules are isolated from direct contact with each other by intervening molecules of the organic compound. In channel solvates, the solvent molecules lie in lattice channels where they are next to other solvent molecules. In metal-ion coordinated solvates, the solvent molecules are bonded to the metal ion.

When the solvent or water is tightly bound, the complex will have a well-defined stoichiometry independent of humidity. When, however, the solvent or water is weakly bound, as in channel solvates and in hygroscopic compounds, the water or solvent content will depend on humidity and drying conditions. In such cases, non-stoichiometry will typically be observed.

Compounds of Formula 1 may also exist as multi-component complexes (other than salts and solvates) in which the compound (drug) and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallization, by recrystallization from solvents, or by physically grinding the components together. See, e.g., O. Almarsson and M. J. Zaworotko, *Chem. Commun.* (2004) 17:1889-1896. For a general review of multi-component complexes, see J. K. Haleblian, *J. Pharm. Sci.* (1975) 64(8): 1269-88.

When subjected to suitable conditions, compounds of Formula 1 may exist in a mesomorphic state (mesophase or liquid crystal). The mesomorphic state lies between the true crystalline state and the true liquid state (either melt or solution). Mesomorphism arising as the result of a change in temperature is described as "thermotropic" and mesomorphism resulting from the addition of a second component, such as water or another solvent, is described as "lyotropic." Compounds that have the potential to form lyotropic mesophases are described as "amphiphilic" and include molecules which possess a polar ionic moiety (e.g., $—COO^-Na^+$, $—COO^-K^+$, $—SO_3^-Na^+$) or polar non-ionic moiety (such as $—N^-N^+(CH_3)_3$). See, e.g., N. H. Hartshorne and A. Stuart, *Crystals and the Polarizing Microscope* (4th ed, 1970).

Compounds of Formula 1 include all polymorphs and crystal habits, stereoisomers, and tautomers thereof, as well as all isotopically-labeled compounds thereof. The compounds of Formula 1 may be administered as prodrugs or form metabolites.

"Prodrugs" refer to compounds having little or no pharmacological activity that can, when metabolized in vivo, undergo conversion to compounds having desired pharmacological activity. Prodrugs may be prepared by replacing appropriate functionalities present in pharmacologically active compounds with "pro-moieties" as described, for example, in H. Bundgaar, *Design of Prodrugs* (1985). Examples of prodrugs include ester, ether or amide derivatives of compounds of Formula 1 having carboxylic acid, hydroxy, or amino functional groups, respectively. For further discussions of prodrugs, see e.g., T. Higuchi and V. Stella "Pro-drugs as Novel Delivery Systems," *ACS Symposium Series* 14 (1975) and E. B. Roche ed., *Bioreversible Carriers in Drug Design* (1987).

"Metabolites" refer to compounds formed in vivo upon administration of pharmacologically active compounds. Examples include hydroxymethyl, hydroxy, secondary amino, primary amino, phenol, and carboxylic acid derivatives of compounds of Formula 1 having methyl, alkoxy, tertiary amino, secondary amino, phenyl, and amide groups, respectively.

Compounds of Formula 1 include all stereoisomers, whether they are pure, substantially pure, or mixtures, and result from the presence of one or more stereogenic centers, one or more double bonds, or both. Such stereoisomers may also result from acid addition or base salts in which the counter-ion is optically active, for example, when the counter-ion is D-lactate or L-lysine.

Compounds of Formula 1 also include all tautomers, which are isomers resulting from tautomerization. Tautomeric isomerism includes, for example, imine-enamine, keto-enol, oxime-nitroso, and amide-imidic acid tautomerism.

Compounds of Formula 1 may exhibit more than one type of isomerism.

Geometrical (cis/trans) isomers may be separated by conventional techniques such as chromatography and fractional crystallization.

Conventional techniques for preparing or isolating a compound having a specific stereochemical configuration include chiral synthesis from a suitable optically pure precursor or resolution of the racemate (or the racemate of a salt or derivative) using, for example, chiral high pressure liquid chromatography (HPLC). Alternatively, the racemate (or a racemic precursor) may be reacted with a suitable optically active compound, for example, an alcohol, or, in the case where the compound of Formula 1 contains an acidic or basic moiety, an acid or base such as tartaric acid or 1-phenylethylamine. The resulting diastereomeric mixture may be separated by chromatography, fractional crystallization, etc., and the appropriate diastereoisomer converted to the compound having the requisite stereochemical configuration. For a further discussion of techniques for separating stereoisomers, see E. L. Eliel and S. H. Wilen, *Stereochemistry of Organic Compounds* (1994).

Compounds of Formula 1 also include all isotopic variations, in which at least one atom is replaced by an atom having the same atomic number, but an atomic mass different from the atomic mass usually found in nature. Isotopes suitable for inclusion in compounds of Formula 1 include, for example, isotopes of hydrogen, such as $^2$H and $^3$H; isotopes of carbon, such as $^{11}$C, $^{13}$C and $^{14}$C; isotopes of nitrogen, such as $^{13}$N and $^{15}$N; isotopes of oxygen, such as $^{15}$O, $^{17}$O and $^{18}$O; isotopes of sulfur, such as $^{35}$S; isotopes of fluorine, such as $^{18}$F; isotopes of chlorine, such as $^{36}$Cl, and isotopes of iodine, such as $^{123}$I and $^{125}$I. Use of isotopic variations (e.g., deuterium, $^2$H) may afford certain therapeutic advantages resulting from greater metabolic stability, for example, increased in vivo half-life or reduced dosage requirements. Additionally, certain isotopic variations of the disclosed compounds may incorporate a radioactive isotope (e.g., tritium, $^3$H, or $^{14}$C), which may be useful in drug and/or substrate tissue distribution studies. Substitution with positron emitting isotopes, such as $^{11}$C, $^{18}$F, $^{15}$O and $^{13}$N, may be useful in Positron Emission Topography (PET) studies for examining substrate receptor occupancy. Isotopically-labeled compounds may be prepared by processes analogous to those described elsewhere in the disclosure using an appropriate isotopically-labeled reagent in place of a non-labeled reagent.

The compounds of Formula 1 may be prepared using the techniques described below. Some of the schemes and examples may omit details of common reactions, including oxidations, reductions, and so on, separation techniques (extraction, evaporation, precipitation, chromatography, filtration, trituration, crystallization, and the like), and analytical procedures, which are known to persons of ordinary skill in the art of organic chemistry. The details of such reactions and techniques can be found in a number of treatises, including Richard Larock, *Comprehensive Organic Transformations* (1999), and the multi-volume series edited by Michael B. Smith and others, *Compendium of Organic Synthetic Methods* (1974 et seq.). Starting materials and reagents may be obtained from commercial sources or may be prepared using literature methods. Some of the reaction schemes may omit minor products resulting from chemical transformations (e.g., an alcohol from the hydrolysis of an ester, $CO_2$ from the decarboxylation of a di-acid, etc.). In addition, in some instances, reaction intermediates may be used in subsequent steps without isolation or purification (i.e., in situ).

In some of the reaction schemes and examples below, certain compounds can be prepared using protecting groups, which prevent undesirable chemical reaction at otherwise reactive sites. Protecting groups may also be used to enhance solubility or otherwise modify physical properties of a compound. For a discussion of protecting group strategies, a description of materials and methods for installing and removing protecting groups, and a compilation of useful protecting groups for common functional groups, including amines, carboxylic acids, alcohols, ketones, aldehydes, and so on, see T. W. Greene and P. G. Wuts, *Protecting Groups in Organic Chemistry* (1999) and P. Kocienski, *Protective Groups* (2000).

Generally, the chemical transformations described throughout the specification may be carried out using substantially stoichiometric amounts of reactants, though certain reactions may benefit from using an excess of one or more of the reactants. Additionally, many of the reactions disclosed throughout the specification may be carried out at about room temperature (RT) and ambient pressure, but depending on reaction kinetics, yields, and so on, some reactions may be run at elevated pressures or employ higher temperatures (e.g., reflux conditions) or lower temperatures (e.g., −78° C. to 0° C.). Any reference in the disclosure to a stoichiometric range, a temperature range, a pH range, etc., whether or not expressly using the word "range," also includes the indicated endpoints.

Many of the chemical transformations may also employ one or more compatible solvents, which may influence the reaction rate and yield. Depending on the nature of the reactants, the one or more solvents may be polar protic solvents (including water), polar aprotic solvents, non-polar solvents, or some combination. Representative solvents include saturated aliphatic hydrocarbons (e.g., n-pentane, n-hexane, n-heptane, n-octane); aromatic hydrocarbons (e.g., benzene, toluene, xylenes); halogenated hydrocarbons (e.g., methylene chloride, chloroform, carbon tetrachloride); aliphatic alcohols (e.g., methanol, ethanol, propan-1-ol, propan-2-ol, butan-1-ol, 2-methyl-propan-1-ol, butan-2-ol, 2-methyl-propan-2-ol, pentan-1-ol, 3-methyl-butan-1-ol, hexan-1-ol, 2-methoxy-ethanol, 2-ethoxy-ethanol, 2-butoxy-ethanol, 2-(2-methoxy-ethoxy)-ethanol, 2-(2-ethoxy-ethoxy)-ethanol, 2-(2-butoxy-ethoxy)-ethanol); ethers (e.g., diethyl ether, di-isopropyl ether, dibutyl ether, 1,2-dimethoxy-ethane, 1,2-diethoxy-ethane, 1-methoxy-2-(2-methoxy-ethoxy)-ethane, 1-ethoxy-2-(2-ethoxy-ethoxy)-ethane, tetrahydrofuran, 1,4-dioxane); ketones (e.g., acetone, methyl ethyl ketone); esters (methyl acetate, ethyl acetate); nitrogen-containing solvents (e.g., formamide, N,N-dimethylformamide, acetonitrile, N-methyl-pyrrolidone, pyridine, quinoline, nitrobenzene); sulfur-containing solvents (e.g., carbon disulfide, dimethyl sulfoxide, tetrahydro-thiophene-1,1,-dioxide); and phosphorus-containing solvents (e.g., hexamethylphosphoric triamide).

In the schemes, below, substituent identifiers (e.g., $R^1$, $R^2$, $R^3$, etc.) are as defined above for Formula 1. As mentioned earlier, however, some of the starting materials and intermediates may include protecting groups, which are removed prior to the final product. In such cases, the substituent identifier refers to moieties defined in Formula 1 and to those moieties with appropriate protecting groups. For example, a starting material or intermediate in the schemes may include $R^8$ having a potentially reactive amine. In such cases, $R^8$ would include the moiety with or without, say, a Boc or Cbz group attached to the amine.

Scheme A shows general methods for preparing compounds of Formula 1 from a pair of substituted 4-azaindoles (A1, A3). In one of the methods, a 5-aminomethyl-4-azaindole (A1) is reacted with a 6-halopyrimidine derivative (A2, $X^1$ is Cl, Br) in a solvent (e.g., acetonitrile) and in the presence of a base (e.g., tertiary amine such as DIPEA) at elevated temperature (e.g., 100-150° C.). Alternatively, the compound of Formula 1 may be prepared through Pd-catalyzed cross-coupling, i.e., reaction of a 6-bromo-4-azaindole (A3) with a boronic acid or borate, stannane, or amine (A4) under Suzuki, Stille, or Buchwald conditions, respectively. For example, compound A3 may be reacted with an boronic acid or borate (e.g., Y is $B(OR^{19})_2$, $R^{19}$ is H or $C_{1-4}$ alkyl) in the presence of a palladium catalyst (e.g., $Pd(PPh_3)_4$, $(PPh_3)_2PdCl_2$, $PdCl_2$(dppf), etc.), a base (e.g., KF, $Na_2CO_3$, $Cs_2CO_3$), and one or more solvents (e.g., dioxane, DMF, $H_2O$, etc.) at elevated temperature (e.g., 90-130° C.). Alternatively, compound A3 may be reacted with an aromatic tin reagent (e.g., Y is —Sn(n-Bu)$_3$) in the presence of a palladium catalyst (e.g., $Pd(PPh_3)_4$) and one or more organic solvents (e.g., toluene, dioxane, etc.) at elevated temperature (e.g., 100-150° C.). Compound A3 may also be reacted with an amine (e.g., Y is H) in the presence of a palladium catalyst (e.g., $Pd_2(dba)_3$, $Pd(OAc)_2$, $PdCl_2$(dppf), etc.) and an optional ligand (e.g., Xantphos), a stoichiometric amount of base (e.g., NaOt-Bu), and one or more organic solvents (e.g., dioxane, toluene, etc.), at elevated temperature (e.g., about 100° C.). As indicated in Scheme A, when compound 1 is racemic, it may be optionally purified by chiral column chromatography (e.g., supercritical fluid chromatography) or by derivatization with optically-pure reagents as described above, to give individual enantiomers 1A or 1B.

Scheme B shows a general method for preparing substituted 4-azaindoles (compounds A1 and A3) depicted in Scheme A. The method begins with the installation of an amine protecting group (G) on starting material B1, in which for example, 6-bromo-1H-pyrrolo[3,2-b]pyridine is reacted with TsCl in sodium hydride and DMF to give 6-bromo-1-tosyl-1H-pyrrolo[3,2-b]pyridine. Treatment of the resulting protected intermediate B2 with an oxidizing agent (e.g., mCPBA) gives an N-oxide intermediate B3, which undergoes cyanation via, for example, reaction with trimethylsilyl cyanide in the presence of base (e.g., tertiary amine such as $Et_3N$) and DMF. The resulting intermediate B4 is deprotected (e.g., Ts is removed via contact with aq NaOH) and is optionally N-alkylated through reaction with an alkyl halide B6 (e.g., $X^2$ is I) under basic conditions (e.g., NaH in DMF). As in Scheme A, reaction of the resulting bromide B7 with a boronic acid or boronate, stannane, or amine (A4) under Suzuki, Stille, or Buchwald conditions, respectively, gives an $R^1$-substituted 4-azaindole intermediate B8. Treatment of bromide B7 or intermediate B8 with a reducing agent (e.g., borane-THF) or reaction with an alkyl-Grignard or alkyl-lithium reagent followed by reduction with sodium borohydride gives, respectively, an amine intermediate B9 or desired compound A1. As in Scheme A, reaction of the amine intermediate B9 with a 6-halopyrimidine derivative A2 gives desired compound A3.

Scheme A

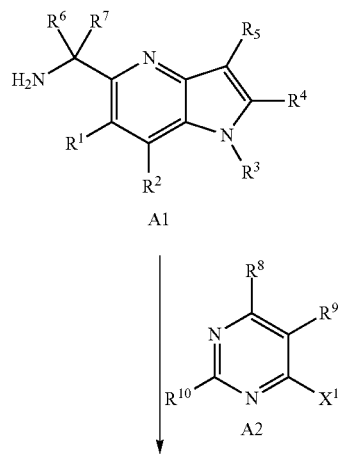

-continued
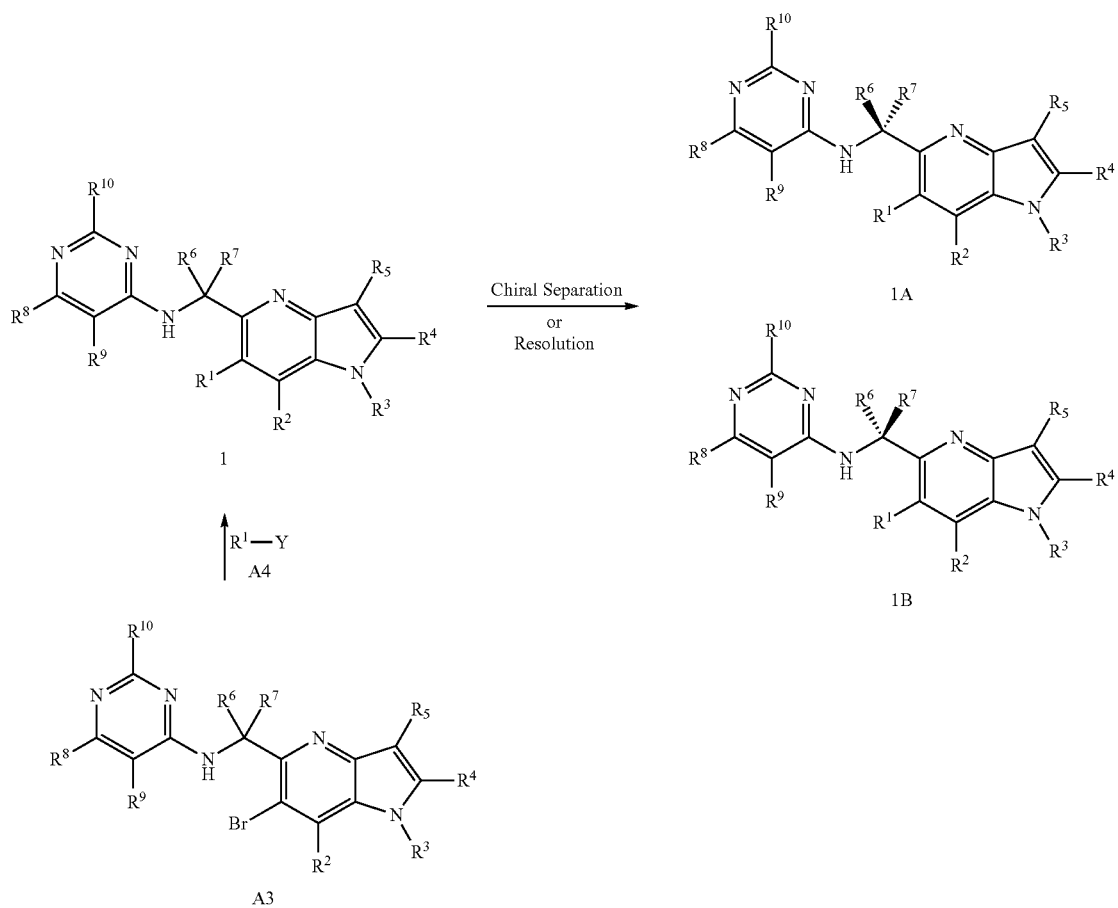
Scheme B
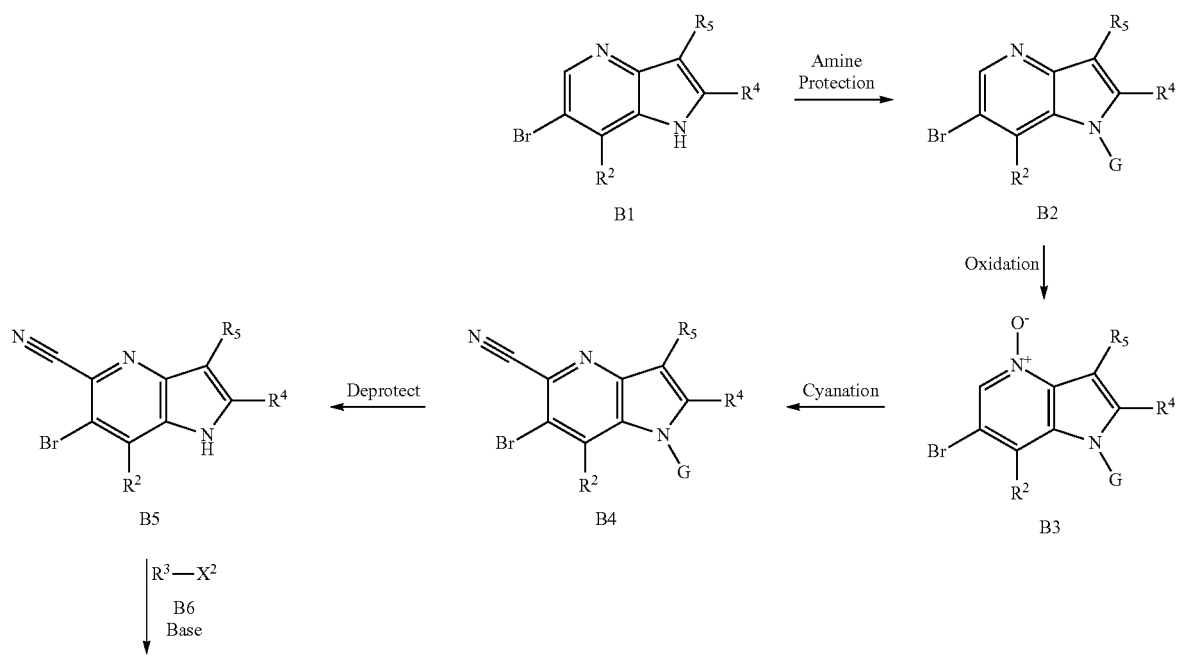

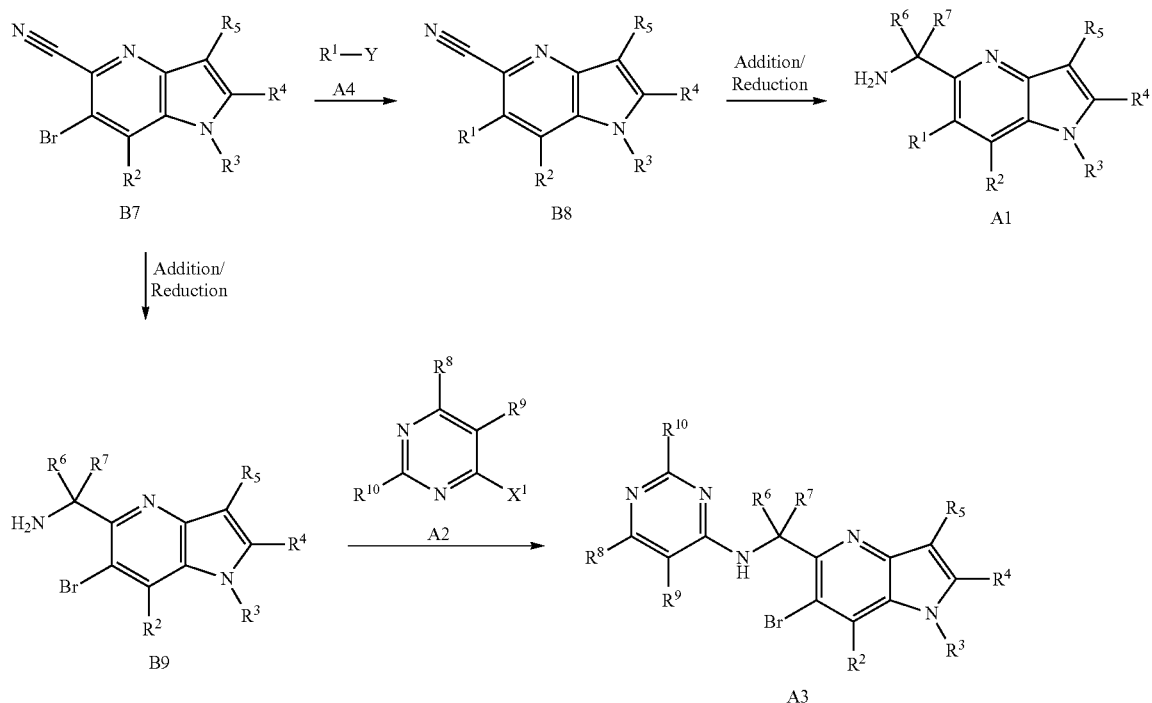

Scheme C shows an alternative method for preparing intermediate B8 depicted in Scheme B. Although Scheme C uses the same starting material as Scheme B, bromide B1 is instead first reacted with a boronic acid or boronate, stannane, or amine (A4) under Suzuki, Stille, or Buchwald conditions, respectively. The resulting $R^1$-substituted 4-azaindole intermediate C1 is optionally N-alkylated through reaction with an alkyl halide B6 under basic conditions (e.g., NaH in DMF). Treatment of the resulting intermediate C2 with an oxidizing agent (e.g., mCPBA) gives an N-oxide intermediate C3, which undergoes cyanation via, for example, reaction with trimethylsilyl cyanide in the presence of base (e.g., tertiary amine such as $Et_3N$) and DMF to give desired intermediate B8.

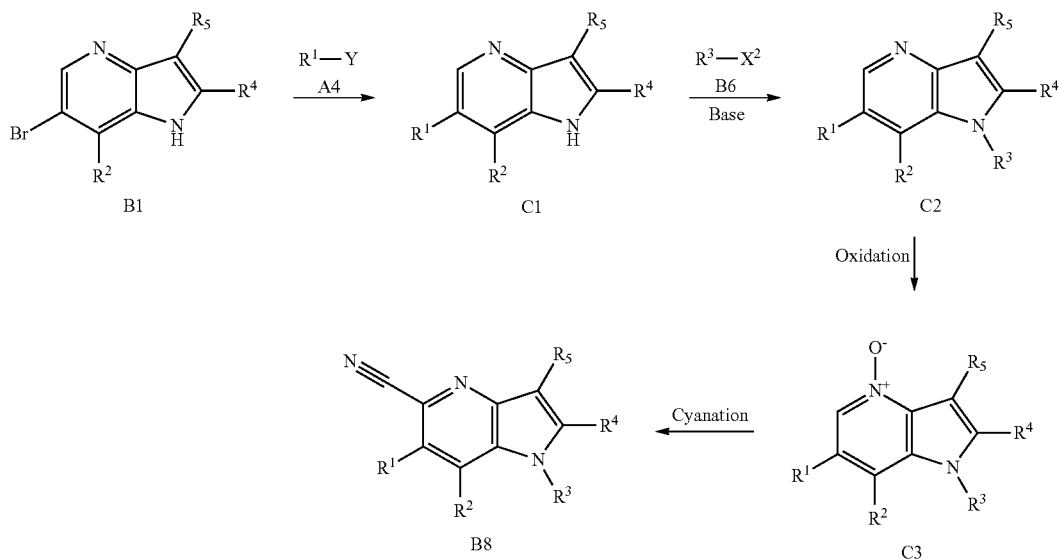

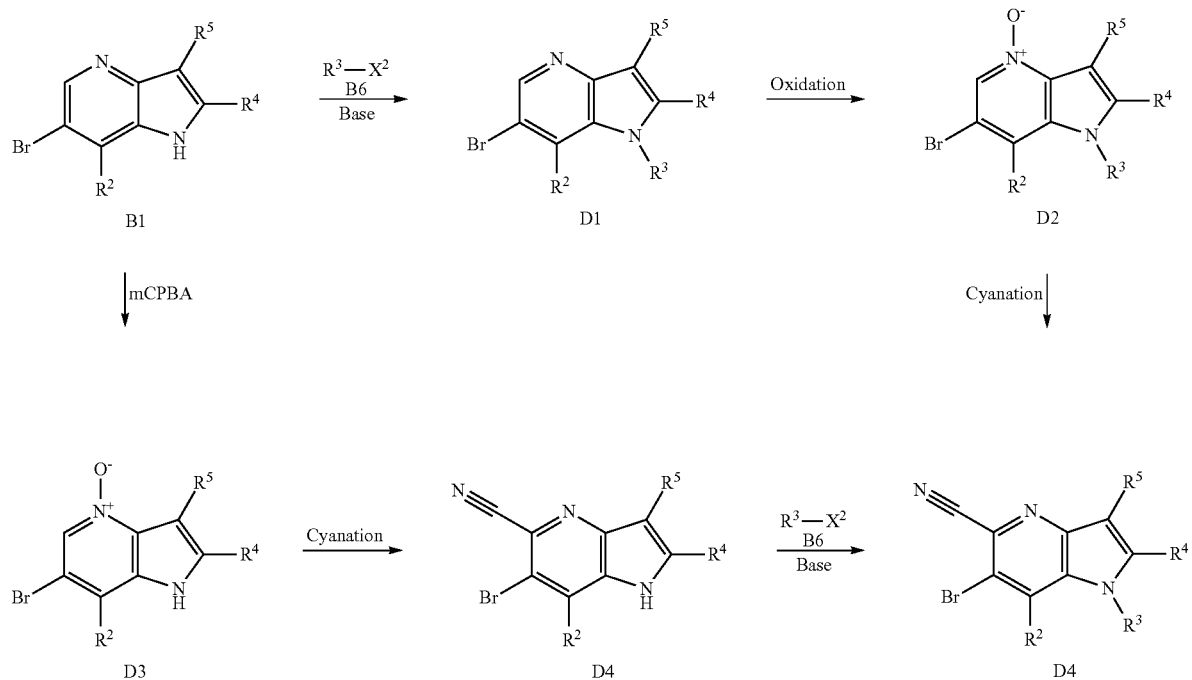

Scheme D shows two additional methods for preparing intermediate B7 depicted in Scheme B. In one of the methods, starting material B1 is optionally N-alkylated through reaction with an alkyl halide B6 under basic conditions (e.g., NaH in DMF). Treatment of the resulting intermediate D1 with an oxidizing agent (e.g., mCPBA) gives an N-oxide intermediate D2, which undergoes cyanation via, for example, reaction with trimethylsilyl cyanide in the presence of base (e.g., tertiary amine such as $Et_3N$) to give desired intermediate B7. Alternatively, starting material B1 may be first treated with an oxidizing agent to give an N-oxide intermediate D3, which subsequently undergoes cyanation. The resulting nitrile intermediate D4 is optionally N-alkylated through reaction with an alkyl halide B6 under basic conditions to give desired intermediate B7.

Scheme E shows alternative methods for preparing enantiomers 1A and 1B. Boc-protected intermediate E1 is resolved by chiral separation, diastereomeric salt formation or other methods of resolution, to give enantiomers E2 and E3. Each of these enantiomers may be first reacted with a boronic acid or boronate, stannane, or amine (A4) under Suzuki, Stille, or Buchwald conditions, respectively, or may undergo direct SNAr reaction to give corresponding enantiomer E4 or E6. Deprotection of the Boc-group by treatment with an acid (TFA, HCl, etc.) followed by reaction with pyrimidine derivative A2 in the presence of a base gives corresponding enantiomer 1A or 1B. Alternatively, Boc-protected E2 or E3 may be first reacted with an acid (TFA, HCl, etc.) to give corresponding free amine E5 or E7. Each may be reacted with a boronic acid or boronate, stannane, or amine (A4) under Suzuki, Stille, or Buchwald conditions, respectively, or may undergo direct SNAr reaction to give a corresponding $R^1$-substituted free amine (not shown) which is subsequently reacted with pyrimidine derivative A2 in the presence of a base to give enantiomer 1A or 1B.

Scheme F shows a method for preparing compounds of Formula 1 in which $R^8$ is $—NH_2$ and $R^9$ is —CN. As in Scheme A, bromide starting material B9 is reacted with a boronic acid or boronate, stannane, or amine (A4) under Suzuki, Stille, or Buchwald conditions, respectively, or may undergo direct SNAr reaction, to give an $R^1$-substituted 5-aminomethyl-4-azaindole intermediate F1. Subsequent reaction of amine F1 with amidine F2 (guanidine when $R^{10}=—NH_2$) and 2-(bis(methylthio)methylene)malononitrile in the presence of a non-nucleophilic base (e.g., $Et_3N$, pyridine, DIPEA, etc.) and one or more solvents (e.g., ACN, pyridine, DMA, DMF, DMPU, DMSO, NMP, etc.) gives desired compound F3. The conversion of compound F1 to compound F3 is typically carried out at elevated temperature (e.g., from about 60° C. to reflux). As indicated in Scheme F, when compound F3 is racemic, it may be optionally purified by chiral column chromatography (e.g., supercritical fluid chromatography) or by derivatization with optically-pure reagents as described above, to give individual enantiomers F3A or F3B.

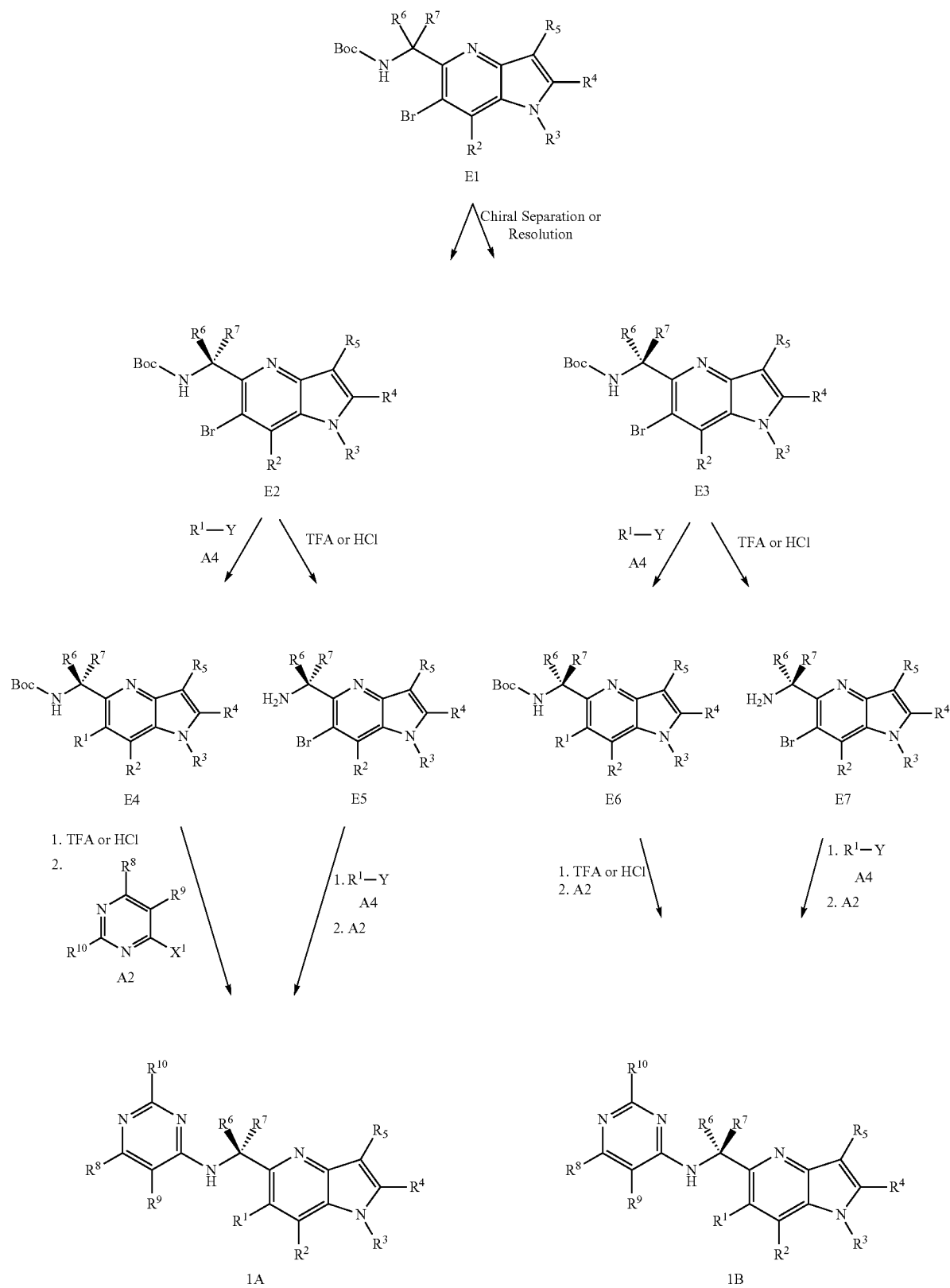

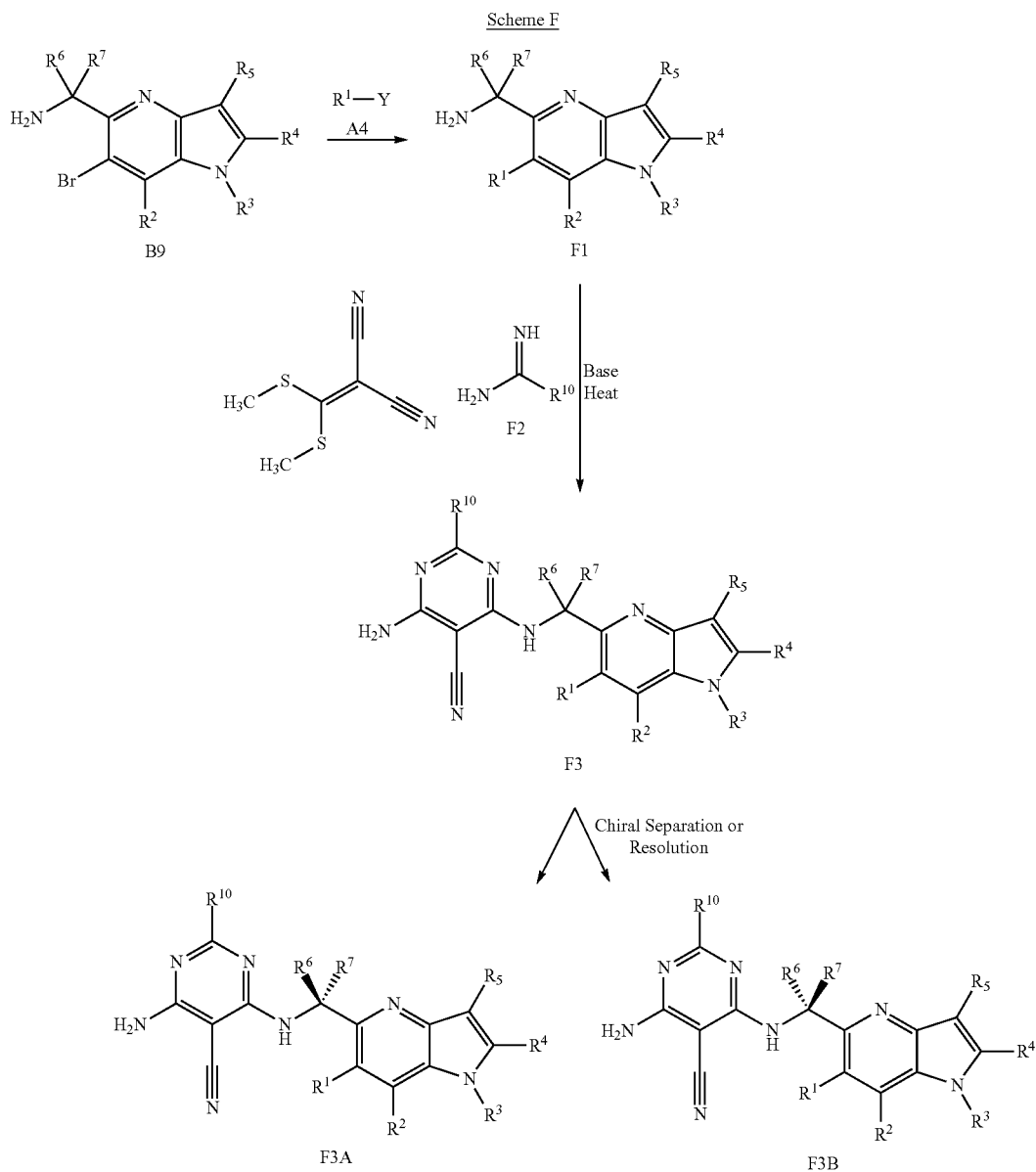

Scheme F

The methods depicted in Schemes A-F may be varied as desired. For example, protecting groups may be added or removed at various steps in the route. In addition, the intermediates may be further elaborated via, for example, alkylation, acylation, hydrolysis, oxidation, reduction, amidation, sulfonation, alkynation, and the like to give the desired final product. Furthermore, any racemic intermediate may be optionally purified by chiral column chromatography (e.g., supercritical fluid chromatography) or by derivatization with optically-pure reagents as described above, to give a desired stereoisomer. Thus, for example, amines A1 or B9 ($R^6$ and $R^7$ are different) in Scheme B or amines B9 or F1 (or both) in Scheme F, may be resolved to give corresponding pure or substantially pure enantiomers, which may reduce or eliminate the need for downstream chiral separation or resolution depicted in Scheme A and Scheme F, respectively.

Compounds of Formula 1, which include compounds named above, and their pharmaceutically acceptable complexes, salts, solvates and hydrates, should be assessed for their biopharmaceutical properties, such as solubility and solution stability across pH, permeability, and the like, to select an appropriate dosage form and route of administration. Compounds that are intended for pharmaceutical use may be administered as crystalline or amorphous products, and may be obtained, for example, as solid plugs, powders, or films by methods such as precipitation, crystallization, freeze drying, spray drying, evaporative drying, microwave drying, or radio frequency drying.

Compounds of Formula 1 may be administered alone or in combination with one another or with one or more pharmacologically active compounds which are different than the compounds of Formula 1. Generally, one or more these compounds are administered as a pharmaceutical composition (a formulation) in association with one or more pharmaceutically acceptable excipients. The choice of excipients depends on the particular mode of administration, the effect of the excipient on solubility and stability, and the nature of the dosage form, among other things. Useful pharmaceutical compositions and methods for their preparation may be found, for example, in A. R. Gennaro (ed.), *Remington: The Science and Practice of Pharmacy* (20th ed., 2000).

Compounds of Formula 1 may be administered orally. Oral administration may involve swallowing in which case the compound enters the bloodstream via the gastrointestinal tract. Alternatively or additionally, oral administration may involve mucosal administration (e.g., buccal, sublingual, supralingual administration) such that the compound enters the bloodstream through the oral mucosa.

Formulations suitable for oral administration include solid, semi-solid and liquid systems such as tablets; soft or hard capsules containing multi- or nano-particulates, liquids, or powders; lozenges which may be liquid-filled; chews; gels; fast dispersing dosage forms; films; ovules; sprays; and buccal or mucoadhesive patches. Liquid formulations include suspensions, solutions, syrups and elixirs. Such formulations may be employed as fillers in soft or hard capsules (made, e.g., from gelatin or hydroxypropylmethylcellulose) and typically comprise a carrier (e.g., water, ethanol, polyethylene glycol, propylene glycol, methylcellulose, or a suitable oil) and one or more emulsifying agents, suspending agents or both. Liquid formulations may also be prepared by the reconstitution of a solid (e.g., from a sachet).

Compounds of Formula 1 may also be used in fast-dissolving, fast-disintegrating dosage forms such as those described in Liang and Chen, *Expert Opinion in Therapeutic Patents* (2001) 11(6):981-986.

For tablet dosage forms, depending on dose, the active pharmaceutical ingredient (API) may comprise from about 1 wt % to about 80 wt % of the dosage form or more typically from about 5 wt % to about 60 wt % of the dosage form. In addition to the API, tablets may include one or more disintegrants, binders, diluents, surfactants, glidants, lubricants, anti-oxidants, colorants, flavoring agents, preservatives, and taste-masking agents. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, $C_{1-6}$ alkyl-substituted hydroxypropylcellulose, starch, pregelatinized starch, and sodium alginate. Generally, the disintegrant will comprise from about 1 wt % to about 25 wt % or from about 5 wt % to about 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropylcellulose and hydroxypropylmethylcellulose. Tablets may also contain diluents, such as lactose (monohydrate, spray-dried monohydrate, anhydrous), mannitol, xylitol, dextrose, sucrose, sorbitol, microcrystalline cellulose, starch and dibasic calcium phosphate dihydrate.

Tablets may also include surface active agents, such as sodium lauryl sulfate and polysorbate 80, and glidants such as silicon dioxide and talc. When present, surface active agents may comprise from about 0.2 wt % to about 5 wt % of the tablet, and glidants may comprise from about 0.2 wt % to about 1 wt % of the tablet.

Tablets may also contain lubricants such as magnesium stearate, calcium stearate, zinc stearate, sodium stearyl fumarate, and mixtures of magnesium stearate with sodium lauryl sulfate. Lubricants may comprise from about 0.25 wt % to about 10 wt % or from about 0.5 wt % to about 3 wt % of the tablet.

Tablet blends may be compressed directly or by roller compaction to form tablets. Tablet blends or portions of blends may alternatively be wet-, dry-, or melt-granulated, melt congealed, or extruded before tableting. If desired, prior to blending one or more of the components may be sized by screening or milling or both. The final dosage form may comprise one or more layers and may be coated, uncoated, or encapsulated. Exemplary tablets may contain up to about 80 wt % of API, from about 10 wt % to about 90 wt % of binder, from about 0 wt % to about 85 wt % of diluent, from about 2 wt % to about 10 wt % of disintegrant, and from about 0.25 wt % to about 10 wt % of lubricant. For a discussion of blending, granulation, milling, screening, tableting, coating, as well as a description of alternative techniques for preparing drug products, see A. R. Gennaro (ed.), *Remington: The Science and Practice of Pharmacy* (20th ed., 2000); H. A. Lieberman et al. (ed.), *Pharmaceutical Dosage Forms: Tablets, Vol.* 1-3 (2d ed., 1990); and D. K. Parikh & C. K. Parikh, *Handbook of Pharmaceutical Granulation Technology, Vol.* 81 (1997).

Consumable oral films for human or veterinary use are pliable water-soluble or water-swellable thin film dosage forms which may be rapidly dissolving or mucoadhesive. In addition to the API, a typical film includes one or more film-forming polymers, binders, solvents, humectants, plasticizers, stabilizers or emulsifiers, viscosity-modifying agents, and solvents. Other film ingredients may include antioxidants, colorants, flavorants and flavor enhancers, preservatives, salivary stimulating agents, cooling agents, co-solvents (including oils), emollients, bulking agents, anti-foaming agents, surfactants, and taste-masking agents. Some components of the formulation may perform more than one function.

In addition to dosing requirements, the amount of API in the film may depend on its solubility. If water soluble, the API would typically comprise from about 1 wt % to about 80 wt % of the non-solvent components (solutes) in the film or from about 20 wt % to about 50 wt % of the solutes in the film. A less soluble API may comprise a greater proportion of the composition, typically up to about 88 wt % of the non-solvent components in the film.

The film-forming polymer may be selected from natural polysaccharides, proteins, or synthetic hydrocolloids and typically comprises from about 0.01 wt % to about 99 wt % or from about 30 wt % to about 80 wt % of the film.

Film dosage forms are typically prepared by evaporative drying of thin aqueous films coated onto a peelable backing support or paper, which may carried out in a drying oven or tunnel (e.g., in a combined coating-drying apparatus), in lyophilization equipment, or in a vacuum oven.

Useful solid formulations for oral administration may include immediate release formulations and modified release formulations. Modified release formulations include delayed-, sustained-, pulsed-, controlled-, targeted-, and programmed-release. For a general description of suitable modified release formulations, see U.S. Pat. No. 6,106,864. For details of other useful release technologies, such as high energy dispersions and osmotic and coated particles, see Verma et al, *Pharmaceutical Technology On-line* (2001) 25(2):1-14.

Compounds of Formula 1 may also be administered directly into the blood stream, muscle, or an internal organ of the subject. Suitable techniques for parenteral administration include intravenous, intraarterial, intraperitoneal, intrathecal, intraventricular, intraurethral, intrasternal, intracranial, intramuscular, intrasynovial, and subcutaneous administration.

Suitable devices for parenteral administration include needle injectors, including microneedle injectors, needle-free injectors, and infusion devices.

Parenteral formulations are typically aqueous solutions which may contain excipients such as salts, carbohydrates and buffering agents (e.g., pH of from about 3 to about 9). For some applications, however, compounds of Formula 1 may be more suitably formulated as a sterile non-aqueous solution or as a dried form to be used in conjunction with a suitable vehicle such as sterile, pyrogen-free water. The preparation of parenteral formulations under sterile conditions (e.g., by lyophilization) may be readily accomplished using standard pharmaceutical techniques.

The solubility of compounds which are used in the preparation of parenteral solutions may be increased through appropriate formulation techniques, such as the incorporation of solubility-enhancing agents. Formulations for parenteral administration may be formulated to be immediate or modified release. Modified release formulations include delayed, sustained, pulsed, controlled, targeted, and programmed release. Thus, compounds of Formula 1 may be formulated as a suspension, a solid, a semi-solid, or a thixotropic liquid for administration as an implanted depot providing modified release of the active compound. Examples of such formulations include drug-coated stents and semi-solids and suspensions comprising drug-loaded poly(DL-lactic-coglycolic) acid (PGLA) microspheres.

Compounds of Formula 1 may also be administered topically, intradermally, or transdermally to the skin or mucosa. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers may include alcohol, water, mineral oil, liquid petrolatum, white petrolatum, glycerin, polyethylene glycol and propylene glycol. Topical formulations may also include penetration enhancers. See, e.g., Finnin and Morgan, *J. Pharm. Sci.* 88(10):955-958 (1999).

Other means of topical administration include delivery by electroporation, iontophoresis, phonophoresis, sonophoresis and microneedle or needle-free (e.g. Powderject™ and Bioject™) injection. Formulations for topical administration may be formulated to be immediate or modified release as described above.

Compounds of Formula 1 may also be administered intranasally or by inhalation, typically in the form of a dry powder, an aerosol spray, or nasal drops. An inhaler may be used to administer the dry powder, which comprises the API alone, a powder blend of the API and a diluent, such as lactose, or a mixed component particle that includes the API and a phospholipid, such as phosphatidylcholine. For intranasal use, the powder may include a bioadhesive agent, e.g., chitosan or cyclodextrin. A pressurized container, pump, sprayer, atomizer, or nebulizer, may be used to generate the aerosol spray from a solution or suspension comprising the API, one or more agents for dispersing, solubilizing, or extending the release of the API (e.g., EtOH with or without water), one or more solvents (e.g., 1,1,1,2-tetrafluoroethane or 1,1,1,2,3,3, 3-heptafluoropropane) which serve as a propellant, and an optional surfactant, such as sorbitan trioleate, oleic acid, or an oligolactic acid. An atomizer using electrohydrodynamics may be used to produce a fine mist.

Prior to use in a dry powder or suspension formulation, the drug product is usually comminuted to a particle size suitable for delivery by inhalation (typically 90% of the particles, based on volume, having a largest dimension less than 5 microns). This may be achieved by any appropriate size reduction method, such as spiral jet milling, fluid bed jet milling, supercritical fluid processing, high pressure homogenization, or spray drying.

Capsules, blisters and cartridges (made, for example, from gelatin or hydroxypropylmethyl cellulose) for use in an inhaler or insufflator may be formulated to contain a powder mixture of the active compound, a suitable powder base such as lactose or starch, and a performance modifier such as L-leucine, mannitol, or magnesium stearate. The lactose may be anhydrous or monohydrated. Other suitable excipients include dextran, glucose, maltose, sorbitol, xylitol, fructose, sucrose, and trehalose.

A suitable solution formulation for use in an atomizer using electrohydrodynamics to produce a fine mist may contain from about 1 µg to about 20 mg of the API per actuation and the actuation volume may vary from about 1 µL to about 100 µL. A typical formulation may comprise one or more compounds of Formula 1, propylene glycol, sterile water, EtOH, and NaCl. Alternative solvents, which may be used instead of propylene glycol, include glycerol and polyethylene glycol.

Formulations for inhaled administration, intranasal administration, or both, may be formulated to be immediate or modified release using, for example, PGLA. Suitable flavors, such as menthol and levomenthol, or sweeteners, such as saccharin or sodium saccharin, may be added to formulations intended for inhaled/intranasal administration.

In the case of dry powder inhalers and aerosols, the dosage unit is determined by means of a valve that delivers a metered amount. Units are typically arranged to administer a metered dose or "puff" containing from about 10 µg to about 1000 µg of the API. The overall daily dose will typically range from about 100 µg to about 10 µg which may be administered in a single dose or, more usually, as divided doses throughout the day.

The active compounds may be administered rectally or vaginally, e.g., in the form of a suppository, pessary, or enema. Cocoa butter is a traditional suppository base, but various alternatives may be used as appropriate. Formulations for rectal or vaginal administration may be formulated to be immediate or modified release as described above.

Compounds of Formula 1 may also be administered directly to the eye or ear, typically in the form of drops of a micronized suspension or solution in isotonic, pH-adjusted, sterile saline. Other formulations suitable for ocular and aural administration include ointments, gels, biodegradable implants (e.g. absorbable gel sponges, collagen), non-biodegradable implants (e.g. silicone), wafers, lenses, and particulate or vesicular systems, such as niosomes or liposomes. The formulation may include one or more polymers and a preservative, such as benzalkonium chloride. Typical polymers include crossed-linked polyacrylic acid, polyvinylalcohol, hyaluronic acid, cellulosic polymers (e.g., hydroxypropylmethylcellulose, hydroxyethylcellulose, methyl cellulose), and heteropolysaccharide polymers (e.g., gelan gum). Such formulations may also be delivered by iontophoresis. Formulations for ocular or aural administration may be formulated to be immediate or modified release as described above.

To improve their solubility, dissolution rate, taste-masking, bioavailability, or stability, compounds of Formula 1 may be combined with soluble macromolecular entities, including cyclodextrin and its derivatives and polyethylene glycol-containing polymers. For example, API-cyclodextrin complexes are generally useful for most dosage forms and routes of administration. Both inclusion and non-inclusion complexes may be used. As an alternative to direct complexation with the API, the cyclodextrin may be used as an auxiliary additive, i.e. as a carrier, diluent, or solubilizer. Alpha-, beta- and gamma-cyclodextrins are commonly used for these purposes. See, e.g., WO 91/11172, WO 94/02518, and WO 98/55148.

As noted above, one or more compounds of Formula 1, including compounds specifically named above, and their pharmaceutically active complexes, salts, solvates and hydrates, may be combined with each other or with one or more other active pharmaceutically active compounds to treat various diseases, disorders or conditions. In such cases, the active compounds may be combined in a single dosage form as described above or may be provided in the form of a kit which is suitable for coadministration of the compositions. The kit comprises (1) two or more different pharmaceutical compositions, at least one of which contains a compound of Formula 1; and (2) a device for separately retaining the two pharmaceutical compositions, such as a divided bottle or a divided foil packet. An example of such a kit is the familiar blister pack used for the packaging of tablets or capsules. The kit is suitable for administering different types of dosage forms (e.g., oral and parenteral) or for administering different pharmaceutical compositions at separate dosing intervals, or for titrating the different pharmaceutical compositions against one another. To assist with patient compliance, the kit typically comprises directions for administration and may be provided with a memory aid.

For administration to human patients, the total daily dose of the claimed and disclosed compounds is typically in the range of about 0.1 mg to about 3000 mg depending on the route of administration. For example, oral administration may require a total daily dose of from about 1 mg to about 3000 mg, while an intravenous dose may only require a total daily dose of from about 0.1 mg to about 300 mg. The total daily dose may be administered in single or divided doses and, at the physician's discretion, may fall outside of the typical ranges given above. Although these dosages are based on an average human subject having a mass of about 60 kg to about 70 kg, the physician will be able to determine the appropriate dose for a patient (e.g., an infant) whose mass falls outside of this weight range.

As noted above, the compounds of Formula 1 may be used to treat diseases, disorders or conditions for which inhibition of PI3Kδ is indicated. Such diseases, disorders or conditions generally relate to any unhealthy or abnormal state in a subject for which the inhibition of PI3Kδ provides a therapeutic or prophylactic benefit. More particularly, such diseases, disorders or conditions may involve the immune system and inflammation, including Type I hypersensitivity (allergic) reactions (allergic rhinitis, allergic asthma, and atopic dermatitis); autoimmune diseases (rheumatoid arthritis, multiple sclerosis, systemic lupus erythematosus, psoriasis, and immune thrombocytopenic purpura); inflammation of the lung (chronic obstructive pulmonary disease), graft-versus-host disease, and thrombosis. The compounds of Formula 1 may also be used to treat diseases, disorders or conditions related to abnormal cell growth, including hematological malignancies, such as acute myeloid leukemia, B-cell chronic lymphocytic leukemia, B-cell lymphoma (e.g., mantle cell lymphoma), and T-cell lymphoma (e.g., peripheral T-cell lymphoma), as well as epithelial cancers (i.e., carcinomas), such as lung cancer (small cell lung cancer and non-small cell lung cancer), pancreatic cancer, and colon cancer.

In addition to the hematological malignancies and epithelial cancers noted above, the compounds of Formula 1 may also be used to treat other types of cancer, including leukemia (chronic myelogenous leukemia and chronic lymphocytic leukemia); breast cancer, genitourinary cancer, skin cancer, bone cancer, prostate cancer, and liver cancer; brain cancer; cancer of the larynx, gall bladder, rectum, parathyroid, thyroid, adrenal, neural tissue, bladder, head, neck, stomach, bronchi, and kidneys; basal cell carcinoma, squamous cell carcinoma, metastatic skin carcinoma, osteosarcoma, Ewing's sarcoma, veticulum cell sarcoma, and Kaposi's sarcoma; myeloma, giant cell tumor, islet cell tumor, acute and chronic lymphocytic and granulocytic tumors, hairy-cell tumor, adenoma, medullary carcinoma, pheochromocytoma, mucosal neuromas, intestinal ganglioneuromas, hyperplastic corneal nerve tumor, marfanoid habitus tumor, Wilms' tumor, seminoma, ovarian tumor, leiomyomater tumor, cervical dysplasia, neuroblastoma, retinoblastoma, myelodysplastic syndrome, rhabdomyosarcoma, astrocytoma, non-Hodgkin's lymphoma, malignant hypercalcemia, polycythermia vera, adenocarcinoma, glioblastoma multiforma, glioma, lymphomas, and malignant melanomas, among others.

In addition to cancer, the compounds of Formula 1 may also be used to treat other diseases related to abnormal cell growth, including non-malignant proliferative diseases such as benign prostatic hypertrophy, restinosis, hyperplasia, synovial proliferation disorder, retinopathy or other neovascular disorders of the eye, among others.

The compounds of Formula 1 may also be used to treat autoimmune disorders in addition to those listed above. Such diseases, disorders or conditions include Crohns disease, dermatomyositis, diabetes mellitus type 1, Goodpasture's syndrome, Graves' disease, Guillain-Barré syndrome, Hashimoto's disease, mixed connective tissue damage, myasthenia gravis, narcolepsy, pemphigus vulgaris, pernicious anemia, polymyositis, primary biliary cirrhosis, Sjögren's syndrome, temporal arteritis, ulcerative colitis, vasculitis, and Wegener's granulomatosis, among others.

Furthermore, compounds of Formula 1 may be used to treat inflammatory disorders including asthma (child-onset asthma, adult-onset asthma, allergic asthma, exercised-induced asthma, cough-variant asthma, occupational asthma, nocturnal asthma, steroid-resistant asthma, etc.), chronic inflammation, chronic prostatitis, glomerulonephritis, hypersensitivities, inflammatory bowel diseases (ulcerative colitis in addition to Crohn's disease), pelvic inflammatory disease, reperfusion injury, transplant failure or rejection, graft-versus-host disease (including acute or chronic GVHD), vasculitis, and systemic inflammatory response syndrome.

The compounds of Formula 1 may also be used to treat specific diseases that may fall within one or more general disorders described above, including arthritis. In addition to rheumatoid arthritis, Sjögren's syndrome, systemic lupus erythematosus, SLE in children and adolescents, compounds of Formula 1 may also be used to treat other arthritis diseases, including ankylosing spondylitis, avascular necrosis, Behcet's disease, bursitis, calcium pyrophosphate dihyrate crystal deposition disease (pseudo gout), carpal tunnel syndrome, Ehlers-Danlos syndrome, fibromyalgia, Fifth disease, giant cell arteritis, gout, juvenile dermatomyositis, juvenile rheumatoid arthritis, juvenile spondyloarthopathy, Lyme disease, Marfan syndrome, myositis, osteoarthritis, osteogenesis imperfect, osteoporosis, Paget's disease, psoriatic arthritis, Raynaud's phenomenon, reactive arthritis, reflex sympathetic dystrophy syndrome, scleroderma, spinal stenosis, Still's disease, and tendinitis, among others.

The claimed and disclosed compounds may be combined with one or more other pharmacologically active compounds or therapies for the treatment of one or more diseases, disorders or conditions for which PI3Kδ is indicated, including diseases, disorders or conditions involving the immune system, inflammation, and abnormal cell growth. For example, compounds of Formula 1, which include compounds specifically named above, and their pharmaceutically acceptable complexes, salts, solvates and hydrates, may be administered simultaneously, sequentially or separately in combination with one or more compounds or therapies for treating arthritis, including rheumatoid arthritis and osteoarthritis, and for treating asthma, graft-versus-host disease, or cancer, including hematological malignancies, such as acute myeloid leukemia, B-cell chronic lymphocytic leukemia, B-cell lymphoma, and T-cell lymphoma, and carcinomas, such as lung cancer, pancreatic cancer, and colon cancer. Such combinations may offer significant therapeutic advantages, including fewer side effects, improved ability to treat underserved patient populations, or synergistic activity.

For example, when used to treat arthritis, the compounds of Formula 1 may be combined with one or more nonsteroidal anti-inflammatory drugs (NSAIDs), analgesics, corticosteroids, biological response modifiers, and protein-A immunoadsorption therapy. Alternatively or additionally, when treating rheumatoid arthritis, the compounds of Formula 1 may be combined with one or more disease modifying antirheumatic drugs (DMARDs), and when treating osteoarthritis, the compounds of Formula 1 may be combined with one or more osteoporosis agents.

Representative NSAIDs include apazone, aspirin, celecoxib, diclofenac (with and without misoprostol), diflunisal, etodolac, fenoprofen, flurbiprofen, ibuprofen, indomethacin, ketoprofen, meclofenamate sodium, mefenamic acid, meloxicam, nabumetone, naproxen, oxaprozin, phenylbutazone, piroxicam, choline and magnesium salicylates, salsalate, and sulindac. Representative analgesics include acetaminophen and morphine sulfate, as well as codeine, hydrocodone, oxycodone, propoxyphene, and tramadol, all with or without acetaminophen. Representative corticosteroids include betamethasone, cortisone acetate, dexamethasone, hydrocortisone, methylprednisolone, prednisolone, and prednisone. Representative biological response modifiers include TNF-α inhibitors, such as adalimumab, etanercept, and infliximab; selective B-cell inhibitors, such as rituximab; IL-1 inhibitors, such as anakinra, and selective costimulation modulators, such as abatacept.

Representative DMARDs include auranofin (oral gold), azathioprine, chlorambucil, cyclophosamide, cyclosporine, gold sodium thiomalate (injectable gold), hydroxychloroquine, leflunomide, methotrexate, minocycline, myophenolate mofetil, penicillamine, and sulfasalazine. Representative osteoporosis agents include bisphosphonates, such as alendronate, ibandronate, risedronate, and zoledronic acid; selective estrogen receptor modulators, such as droloxifene, lasofoxifene, and raloxifene; hormones, such as calcitonin, estrogens, and parathyroid hormone; and immunosuppressant agents such as azathioprine, cyclosporine, and rapamycin.

Particularly useful combinations for treating rheumatoid arthritis include a compound of Formula 1 and methotrexate; a compound of Formula 1 and one or more biological response modifiers, such as lefluonomide, etanercept, adalimumab, and infliximab; or a compound of Formula 1, methotrexate, and one or more biological response modifiers, such as lefluonomide, etanercept, adalimumab, and infliximab.

For the treatment of thrombis and restensosis, the compounds of Formula 1 may be combined with one or more cardiovascular agents such as calcium channel blockers, statins, fibrates, beta-blockers, ACE inhibitors, and platelet aggregation inhibitors.

For the treatment of asthma, the compounds of Formula 1 may be combined with one or more long-term asthma control medications, including inhaled corticosteroids, leukotriene modifiers, long-acting beta agonists, combination inhalers, and theophylline. Representative inhaled corticosteroids include beclomethasone, budesonide, ciclesonide, flunisolide, fluticasone, and mometasone; representative leukotriene modifiers include montelukast, zafirlukast, and zileuton; and representative long-acting beta agonists include salmeterol and formoterol, which are typically administered in combination with an inhaled corticosteroid. Combination inhalers contain a long-acting beta agonist and a corticosteroid, such as fluticasone-salmeterol, budesonide-formoterol, and mometasone-formoterol. The compounds of Formula 1 may also be combined with allergy medications, including allergy shots which reduce the immune system's response to particular allergens, with omalizumab, and with other allergy medications, such as oral and nasal spray antihistamines and decongestants, corticosteroid and cromolyn nasal sprays.

For the treatment (including prophylaxis) of acute or chronic graft-versus-host disease, the compounds of Formula 1 may be combined with one or more compounds including immunosuppressive drugs, immunomodulating agents, including thalidomide, photoactive agents, antineoplastic agents, monoclonal antibodies, polyvalent antibodies or immunoglobulins, and tumor necrosis factor inhibitors. Representative immunosuppressive drugs include corticosteroids, cyclosporine, methylprednisolone, mycophenolate mofetil, prednisone, rapamycin, tacrolimus, and antithymocyte globulin; representative photoactive agents include psoralen and its derivatives, including methoxsalen, and psoralen plus ultraviolet A treatment. Representative antineoplastic agents include methotrexate, which is typically administered with cyclosporine or tacrolimus, and azathioprine, which is typically administered with steroids and cyclosporine, as well as denileukin and pentostatin. Representative monoclonal antibodies include anti-TNF-α antibodies, such as infliximab, anti-CD3 antibodies, such as muromonab-CD3, otelixizumab, teplizumab, and visilizumab, and anti-CD5 antibodies. Other monoclonal antibodies include anti-CD20 antibodies, such as ibritumomab, ofatumumab, rituximab, tiuxetan, tositumomab, and veltuzumab, anti-CD52 antibodies, such as alemtuzumab, and anti-IL-2 antibodies, such as daclizumab. Representative polyvalent antibodies and immunoglobulins include antithymocyte globulin-equine and human intravenous immune globulin. Representative TNF inhibitors include etanercept.

The compounds of Formula 1 may also be combined with one or more compounds or therapies for treating cancer. These include chemotherapeutic agents (i.e., cytotoxic or antineoplastic agents) such as alkylating agents, antibiotics, antimetabolic agents, plant-derived agents, and topoisomerase inhibitors, as well as molecularly targeted drugs which block the growth and spread of cancer by interfering with specific molecules involved in tumor growth and progression. Molecularly targeted drugs include both small molecules and biologics.

Representative alkylating agents include bischloroethylamines (nitrogen mustards, e.g., chlorambucil, cyclophosphamide, ifosfamide, mechlorethamine, melphalan, and uracil mustard); aziridines (e.g., thiotepa); alkyl alkone sulfonates (e.g., busulfan); nitrosoureas (e.g., carmustine, lomustine, and streptozocin); nonclassical alkylating agents (e.g., altretamine, dacarbazine, and procarbazine); and platinum compounds (e.g., carboplatin, cisplatin, nedaplatin, oxaliplatin, satraplatin, and triplatin tetranitrate).

Representative antibiotic agents include anthracyclines (e.g., aclarubicin, amrubicin, daunorubicin, doxorubicin, epirubicin, idarubicin, pirarubicin, valrubicin, and zorubicin); anthracenediones (e.g., mitoxantrone and pixantrone); and

*streptomyces* (e.g., actinomycin, bleomycin, dactinomycin, mitomycin C, and plicamycin).

Representative antimetabolic agents include dihydrofolate reductase inhibitors (e.g., aminopterin, methotrexate, and pemetrexed); hymidylate synthase inhibitors (e.g., raltitrexed and pemetrexed); folinic acid (e.g., leucovorin); adenosine deaminase inhibitors (e.g., pentostatin); halogenated/ribonucleotide reductase inhibitors (e.g., cladribine, clofarabine, and fludarabine); thiopurines (e.g, thioguanine and mercaptopurine); thymidylate synthase inhibitors (e.g., fluorouracil, capecitabine, tegafur, carmofur, and floxuridine); DNA polymerase inhibitors (e.g., cytarabine); ribonucleotide reductase inhibitors (e.g., gemcitabine); hypomethylating agent (e.g., azacitidine and decitabine); and ribonucleotide reductase inhibitor (e.g., hydroxyurea); and an asparagine depleter (e.g., asparaginase)

Representative plant-derived agents include vinca alkaloids (e.g., vincristine, vinblastine, vindesine, vinzolidine, and vinorelbine), podophyllotoxins (e.g., etoposide and teniposide), and taxanes (e.g., docetaxel, larotaxel, ortataxel, paclitaxel, and tesetaxel).

Representative type I topoisomerase inhibitors include camptothecins, such as belotecan, irinotecan, rubitecan, and topotecan. Representative type II topoisomerase inhibitors include amsacrine, etoposide, etoposide phosphate, and teniposide, which are derivatives of epipodophyllotoxins.

Molecularly targeted therapies include biologic agents such as cytokines and other immune-regulating agents. Useful cytokines include interleukin-2 (IL-2, aldesleukin), interleukin 4 (IL-4), interleukin 12 (IL-12), and interferon, which includes more than 23 related subtypes. Other cytokines include granulocyte colony stimulating factor (CSF) (filgrastim) and granulocyte macrophage CSF (sargramostim). Other immuno-modulating agents include bacillus Calmette-Guerin, levamisole, and octreotide; monoclonal antibodies against tumor antigens, such as trastruzumab and rituximab; and cancer vaccines, which induce an immune response to tumors.

In addition, molecularly targeted drugs that interfere with specific molecules involved in tumor growth and progression include inhibitors of epidermal growth factor (EGF), transforming growth factor-alpha (TGF$_\alpha$), TGF$_\beta$, heregulin, insulin-like growth factor (IGF), fibroblast growth factor (FGF), keratinocyte growth factor (KGF), colony stimulating factor (CSF), erythropoietin (EPO), interleukin-2 (IL-2), nerve growth factor (NGF), platelet-derived growth factor (PDGF), hepatocyte growth factor (HGF), vascular endothelial growth factor (VEGF), angiopoietin, epidermal growth factor receptor (EGFR), human epidermal growth factor receptor 2 (HER2), HER4, insulin-like growth factor 1 receptor (IGF1R), IGF2R, fibroblast growth factor 1 receptor (FGF1R), FGF2R, FGF3R, FGF4R, vascular endothelial growth factor receptor (VEGFR), tyrosine kinase with immunoglobulin-like and epidermal growth factor-like domains 2 (Tie-2), platelet-derived growth factor receptor (PDGFR), Abl, Bcr-Abl, Raf, FMS-like tyrosine kinase 3 (FLT3), c-Kit, Src, protein kinase c (PKC), tropomyosin receptor kinase (Trk), Ret, mammalian target of rapamycin (mTOR), Aurora kinase, polo-like kinase (PLK), mitogen activated protein kinase (MAPK), mesenchymal-epithelial transition factor (c-MET), cyclin-dependant kinase (CDK), Akt, extracellular signal-regulated kinases (ERK), poly(ADP) ribose polymerase (PARP), and the like.

Specific molecularly targeted drugs include selective estrogen receptor modulators, such as tamoxifen, toremifene, fulvestrant, and raloxifene; antiandrogens, such as bicalutamide, nilutamide, megestrol, and flutamide; and aromatase inhibitors, such as exemestane, anastrozole, and letrozole. Other specific molecularly targeted drugs include agents which inhibit signal transduction, such as imatinib, dasatinib, nilotinib, trastuzumab, gefitinib, erlotinib, cetuximab, lapatinib, panitumumab, and temsirolimus; agents that induce apoptosis, such as bortezomib; agents that block angiogensis, such as bevacizumab, sorafenib, and sunitinib; agents that help the immune system destroy cancel cells, such as rituximab and alemtuzumab; and monoclonal antibodies which deliver toxic molecules to cancer cells, such as gemtuzumab ozogamicin, tositumomab, 131I-tositumoab, and ibritumomab tiuxetan.

Biological Activity

The activity of compounds as PI3Kδ inhibitors may be determined by a variety of methods, including in vitro and in vivo methods. The following in vitro assay measures a test compound's ability to inhibit PI3Kδ-mediated phosphorylation of PIP2 and ATP.

Recombinant GST-tagged PIK3CD is purchased from Invitrogen (Part Number: PV5274). The protein is full length and co-expressed with untagged PIK3R1, phosphoinositide-3-kinase regulatory subunit 1 (p85α). The protein is stored at −20° C. in 50 mM TRIS (pH 7.5), 150 mM NaCl, 0.5 mM EDTA, 0.02% Triton® X-100, 2 mM DTT, and 50% glycerol.

A modified PIK3CD Adapta® assay (Invitrogen, Carlsbad, Calif.) is used to measure PI3Kδ inhibition of the example compounds. The assay has two phases. In the first phase, kinase reaction components, which include the enzyme (PIK3CD), substrates (PIP2, ATP), test compound (inhibitor), and assay buffer are added to each well, and the reaction is allowed to incubate for a pre-determined period of time. After reaction, a detection solution composed of a Eu (europium)-labeled anti-ADP antibody, Alexa Fluor® 647-labeled ADP tracer, and EDTA (to stop the kinase reaction) is added to each assay well. In this second phase, ADP formed by the kinase reaction displaces the Alexa Fluor® 647-labeled ADP tracer from the antibody, resulting in a decrease in time-resolved fluorescence resonance energy transfer (TR-FRET) signal. In the presence of the inhibitor, the amount of ADP formed by the kinase reaction is reduced, and the resulting intact antibody-tracer interaction maintains a high TR-FRET signal.

The assay uses black Greiner® 384-well plates (784076). The reaction buffer contains 50 mM Hepes (pH 7.5), 3 mM MgCl$_2$, 1 mM EGTA, 100 mM NaCl, 0.03% CHAPS; 2 mM DTT is added fresh prior to each experiment. Enzyme (4 μL, estimated 1.5 nM in buffer) is first added to the wells of the plate. Next, test compounds (2 μL) from a source plate (5% dilution plate) are introduced into the wells. The final DMSO concentration in each assay well is 1%. The dilution plate contains 5% DMSO in the bottom half of columns 23 and 24, which serve as negative (non-inhibited) controls; the top half contains a known inhibitor concentration (positive control) that gives >98% inhibition of the kinase reaction. Other wells contain test compounds serially diluted across the plate 11 times for a total of 12 data points. The kinase reactions are carried out at room temperature and are initiated by the addition of 4 μL of solution containing 2 μM ATP and 50 μM PIP2. Each reaction is stopped after 1 hour±10 minutes via addition of 10 μL stop solution, which contains a final assay concentration of 3 nM Alexa Fluor® 647-labeled ADP tracer, 2 nM Eu-anti-ADP Antibody, and 10 mM EDTA. After allowing the solutions to equilibrate for 30±10 minutes, a PHERAstar plate reader is used to excite the Eu donor (at 337 nm) and to detect emission from the Alexa Fluor® 647 at 665 nm. This emission signal is referenced or "ratioed" to the emission from Eu at 620 nm. The emission ratio (665 nm/620 nm) from each well is collected and converted to percent conversion using a standard curve for the assay conditions: % conversion=B*(C+A−emission ratio)/(emission ratio−C), where "A" and "C" are the maximum and minimum values of the emission ratio obtained from the standard curve of emission ratio vs. % conversion (ATP-ADP); "B" is the emission ratio corresponding to the % conversion at the $EC_{50}$ value for the ADP Tracer—Eu anti-ADP antibody complex. The percent inhibition for a given inhibitor concentration is computed from % conversion for the reaction and for the positive and negative controls. Corresponding $IC_{50}$ values are calculated by non-linear curve fitting of the compound concentrations and values of percent inhibition to the standard $IC_{50}$ equation and are reported as $pIC_{50}$, i.e., $-\log(IC_{50})$, where $IC_{50}$ is molar concentration at 50% inhibition.

EXAMPLES

The following examples are intended to be illustrative and non-limiting, and represent specific embodiments of the present invention.

$^1$H Nuclear magnetic resonance (NMR) spectra were obtained for many of the compounds in the following examples. Characteristic chemical shifts (δ) are given in parts-per-million downfield from tetramethylsilane using conventional abbreviations for designation of major peaks, including s (singlet), d (doublet), t (triplet), q (quartet), m (multiplet), and br (broad). The following abbreviations are used for common solvents: $CDCl_3$ (deuterochloroform), $DMSO-d_6$ (deuterodimethylsulfoxide), $CD_3OD$ (deuteromethanol), $CD_3CN$ (deuteroacetonitrile), and $THF-d_8$ (deuterotetrahydrofuran). The mass spectra (M+H) were recorded using either electrospray ionization (ESI-MS) or atmospheric pressure chemical ionization (APCI-MS).

Where indicated, products of certain preparations and examples are purified by mass-triggered HPLC (Pump: Waters™ 2525; MS: ZQ™; Software: MassLynx™), flash chromatography or preparative thin layer chromatography (TLC). Reverse phase chromatography is typically carried out on a column (e.g., Gemini™ 5μ C18 110A, Axia™ 30×75 mm, 5μ) under acidic conditions ("acid mode") eluting with ACN and water mobile phases containing 0.035% and 0.05% trifluoroacetic acid (TFA), respectively, or under basic conditions ("basic mode") eluting with water and 20/80 (v/v) water/acetonitrile mobile phases, both containing 10 mM $NH_4HCO_3$. Preparative TLC is typically carried out on silica gel 60 $F_{254}$ plates. After isolation by chromatography, the solvent is removed and the product is obtained by drying in a centrifugal evaporator (e.g., GeneVac™), rotary evaporator, evacuated flask, etc. Reactions in an inert (e.g., nitrogen) or reactive (e.g., $H_2$) atmosphere are typically carried out at a pressure of about 1 atmosphere (14.7 psi).

Preparation x1: 6-Bromo-1-methyl-1H-pyrrolo[3,2-b]pyridine-5-carbonitrile

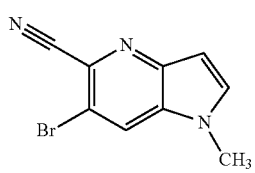

Step A: 6-Bromo-1-tosyl-1H-pyrrolo[3,2-b]pyridine

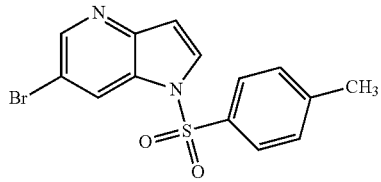 [SMILES: Cc1ccc(S(=O)(=O)n2ccc3ncc(Br)cc32)cc1]

To a solution of 6-bromo-1H-pyrrolo[3,2-b]pyridine (4.0 g, 20.3 mmol) in DMF (40 mL) at 0° C. was added sodium hydride (893 mg, 22.33 mmol). The reaction mixture was stirred at 0° C. for 30 minutes. Next, p-toluensulfonyl chloride (4.64 g, 24.26 mmol) was added, and the reaction mixture was stirred for 1 hour while warming to RT. The reaction mixture was subsequently diluted with DCM (300 mL) and washed with brine. The combined organic layers were dried over $MgSO_4$, concentrated in vacuo, and purified by silica gel chromatography (1% to 2% MeOH/DCM) to give the title compound as a white solid (6.87 g, 96%). $^1$H NMR (500 MHz, $CDCl_3$) δ ppm 8.58 (d, 1H, J=2.0 Hz), 8.43 (d, 1H, J=2.0 Hz), 7.74-7.78 (m, 3H), 7.29 (d, 2H, J=8.0 Hz), 6.83 (d, 1H, J=4.0 Hz), 2.38 (s, 3H); ESI-MS m/z [M+H]$^+$ calc'd for $C_{14}H_{11}BrN_2O_2S$, 351, 353; found 351, 353.

Step B: 6-Bromo-1-tosyl-1H-pyrrolo[3,2-b]pyridine 4-oxide

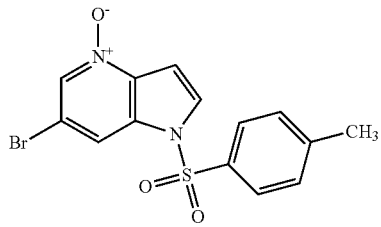 [SMILES: Cc1ccc(S(=O)(=O)n2ccc3c2cc(Br)c[n+]3[O-])cc1]

To a stirred solution of 6-bromo-1-tosyl-1H-pyrrolo[3,2-b]pyridine (6.87 g, 19.56 mmol) in DCM (100 mL) at 0° C. was added 3-chloroperbenzoic acid (77 wt %, 5.26 g, 23.47 mmol). The reaction mixture was stirred at RT until the starting material was completely consumed, as monitored by HPLC. After 8 h, the solution was washed with saturated aqueous $NaHCO_3$ (2×). The organic phase was dried over $MgSO_4$, concentrated in vacuo, and purified by silica gel chromatography (2% to 4% MeOH/DCM) to give the title compound as a white solid (5.66 g, 79%). $^1$H NMR (500 MHz, $CDCl_3$) δ ppm 8.30 (s, 1H), 8.06 (s, 1H), 7.78 (d, 2H, J=8.0 Hz), 7.65 (d, 1H, J=3.5 Hz), 7.33 (d, 2H, J=8.0 Hz), 7.06 (d, 1H, J=3.5 Hz), 2.41 (s, 3H); ESI-MS m/z [M+H]$^+$ calc'd for $C_{14}H_{11}BrN_2O_3S$, 367, 369; found 367, 369.

Step C: 6-Bromo-1-tosyl-1H-pyrrolo[3,2-b]pyridine 5-carbonitrile

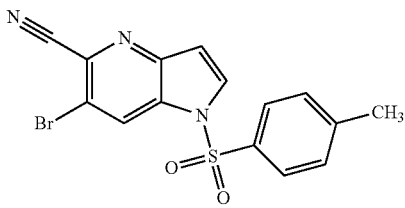 [SMILES: Cc1ccc(S(=O)(=O)n2ccc3nc(C#N)c(Br)cc32)cc1]

To a stirred mixture of 6-bromo-1-tosyl-1H-pyrrolo[3,2-b]pyridine 4-oxide (5.66 g, 15.41 mmol), Et$_3$N (21.5 mL, 154 mmol) and DCE (40 mL) was added trimethylsilyl cyanide (10.33 mL, 77 mmol), and the reaction mixture was stirred at 76° C. for 16 hours. The dark reaction mixture was concentrated in vacuo and purified by silica gel chromatography (1% to 2% MeOH/DCM) to give the title compound as a white solid (3.48 g, 60%). $^1$H NMR (500 MHz, CDCl$_3$) δ ppm 8.56 (d, 1H, J=1.0 Hz), 7.90 (d, 1H, J=4.0 Hz), 7.79 (d, 2H, J=8.0 Hz), 7.33 (d, 2H, J=8.0 Hz), 6.88 (d, 1H, J=4.0 Hz), 2.41 (s, 3H); ESI-MS m/z [M+H]$^+$ calc'd for C$_{15}$H$_{10}$BrN$_3$O$_2$S, 376, 378; found 376, 378. Further elution of the silica gel column with 4% MeOH/DCM gave a second major fraction, which was the tosyl-deprotected product, which was collected to give impure 6-bromo-1H-pyrrolo[3,2-b]pyridine 5-carbonitrile as a brown solid (1.25 g, 36%). ESI-MS m/z [M+H]$^+$ calc'd for C$_8$H$_4$BrN$_3$, 222, 224; found 222, 224.

Step D: 6-Bromo-1-methyl-1H-pyrrolo[3,2-b]pyridine-5-carbonitrile

To a stirred mixture of 6-bromo-1-tosyl-1H-pyrrolo[3,2-b]pyridine 5-carbonitrile (2.46 g, 6.54 mmol), THF (6 mL) and MeOH (6 mL) was added 1N NaOH (3 mL). The reaction mixture was stirred for 30 minutes and then neutralized with 1N HCl and extracted with EtOAc (2×). The organic phase was dried over MgSO$_4$ and concentrated in vacuo to give crude intermediate 6-bromo-1H-pyrrolo[3,2-b]pyridine 5-carbonitrile, which was subsequently dissolved in DMF (10 mL) and cooled to 0° C. Sodium hydride (60%, 314 mg, 7.85 mmol) was added, and the reaction mixture was stirred 30 minutes. Next, iodomethane (0.49 mL, 7.85 mmol) was added, and the reaction mixture was stirred for 30 minutes while warming to RT. The solution was subsequently diluted with EtOAc (100 mL), quenched and washed with brine. The aqueous layer was back-extracted with EtOAc (2×). The combined organic layers were dried over MgSO$_4$, concentrated in vacuo, and purified by silica gel chromatography (2% MeOH/DCM) to give the title compound as a white solid (1.05 g, 68%). $^1$H NMR (500 MHz, CDCl$_3$) δ ppm 7.90 (s, 1H), 7.43 (d, 1H, J=3.5 Hz), 6.76 (d, 1H, J=3.5 Hz), 3.85 (s, 3H); ESI-MS m/z [M+H]$^+$ calc'd for C$_9$H$_6$BrN$_3$, 236, 238; found 236, 238.

Preparation x2: 6-Bromo-1-methyl-1H-pyrrolo[3,2-b]pyridine-5-carbonitrile

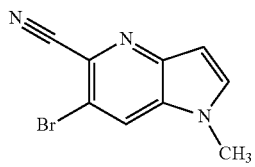

Method A

Step A:
6-Bromo-1-methyl-1H-pyrrolo[3,2-b]pyridine

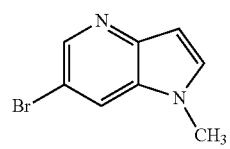

Sodium hydride (60%, 670 mg, 16.8 mmol) was added to a solution of 6-bromo-1H-pyrrolo[3,2-b]pyridine (3.00 g, 15.2 mmol) in DMF (20 mL) at 0° C., and the reaction mixture was stirred for 30 minutes. Iodomethane (1.05 mL, 16.8 mmol) was added. The reaction mixture was subsequently stirred for 30 minutes while warming to RT, diluted with EtOAc, quenched and washed with brine. The aqueous layer was extracted with EtOAc (2×) and the combined organic layers were dried over MgSO$_4$, concentrated, and purified by silica gel chromatography (50% EtOAc/DCM) to give the title compound as a white solid (2.98 g, 93%). $^1$H NMR (500 MHz, DMSO-d$_6$) δ ppm 8.38 (d, 1H, J=2.0 Hz), 8.21 (d, 1H, J=2.0 Hz), 7.65 (d, 1H, J=3.5 Hz), 6.57 (d, 1H, J=3.5 Hz), 3.81 (s, 3H); ESI-MS m/z [M+H]$^+$ calc'd for C$_8$H$_7$BrN$_2$, 211, 213; found 211, 213.

Step B:
6-Bromo-1-methyl-1H-pyrrolo[3,2-b]pyridine 4-oxide

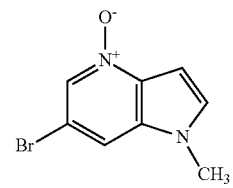

3-Chloroperbenzoic acid (77 wt %, 3.46 g, 15.4 mmol) was added to a stirred solution of 6-bromo-1-methyl-1H-pyrrolo[3,2-b]pyridine (2.96 g, 14.0 mmol) in DCM (60 mL) at 0° C. The reaction mixture was stirred at RT for 4 hours and then concentrated and purified by silica gel chromatography (7% MeOH/DCM) to give the title compound as a brown semi-solid, which was used without further purification (3.8 g). ESI-MS m/z [M+H]$^+$ calc'd for C$_8$H$_7$BrN$_2$O, 227, 229; found 227, 229.

Step C: 6-Bromo-1-methyl-1H-pyrrolo[3,2-b]pyridine-5-carbonitrile

To a stirred mixture of 6-bromo-1-methyl-1H-pyrrolo[3,2-b]pyridine 4-oxide (3.8 g 14 mmol), Et$_3$N (19.51 mL, 140 mmol) and DCE (20 mL) was added trimethylsilyl cyanide (9.38 mL, 70.0 mmol). The reaction mixture was stirred at 80° C. for 5 h, subsequently concentrated in vacuo, and purified by silica gel chromatography eluting with EtOAc/DCM (1:1) to give the title compound as an off-white solid (2.50 g, 76%, 2 steps). ESI-MS m/z [M+H]$^+$ calc'd for C$_9$H$_6$BrN$_3$, 236, 238; found 236, 238.

Method B

Step A: (E)-2-(5-Bromo-3-nitropyridin-2-yl)-N,N-dimethylethen-1-amine

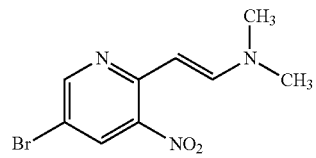

N,N-Dimethylformamide (270 kg), 5-bromo-2-methyl-3-nitropyridine (90.0 kg, 415 mol), and N,N-dimethylformamide dimethyl acetal (108.0 kg, 906.3 mol) were added to a 2000 L vessel at RT. The reaction mixture was stirred at RT for 30 minutes, then heated to 90±5° C. over a 3-hour period and maintained at this temperature for 4 hours. The mixture was subsequently cooled to 25±5° C. Water (945 kg) was added while keeping the temperature of the mixture at 25±5° C. After the addition of water, the reaction mixture was stirred for 2 hours. The solids were centrifuged to obtain wet product, which was slurried in isopropanol (207 kg) for 1 hour at 25±5° C. The solids were centrifuged again to obtain the title compound as a wet solid (105 kg, 92.5 wt % assay). The product was used in the next step without additional drying.

Step B: 6-Bromo-1H-pyrrolo[3,2-b]pyridine

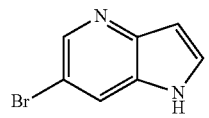

A 1000 L vessel was charged with isopropanol (280 kg). Wet (E)-2-(5-bromo-3-nitropyridin-2-yl)-N,N-dimethylethen-1-amine (40.0 kg based on assay, 147 mol) from the previous step was added at 30±5° C., followed by FeCl₃ (1.6 kg) and activated carbon (2.4 kg) in one portion. A solution of 80% hydrazine hydrate (55.2 kg, 905.7 mol) was diluted with water (24.8 kg) to afford 55% hydrazine hydrate (80 kg), which was added to the mixture in one portion. The reaction mixture was stirred at 30-70° C. for 2 hours and then heated at 80±5° C. for 20 hours. The reaction mixture was cooled to 40±5° C. and Celite (6.0 kg) was added. The resulting mixture was filtered and the filtrate was concentrated to about 80 L. Ethyl acetate (216 kg) was added, followed by activated charcoal (2.4 kg) and the resulting mixture was stirred for 30 minutes and then filtered. The filter cake was washed with EtOAc (72 kg). The combined filtrate was washed with 16.7% brine (280 kg) and the layers were separated. The aqueous layer was extracted with EtOAc (144 kg). The organic layers were combined to give the title compound in EtOAc solution (440 kg, 4.75 wt % by assay).

Step C:
6-Bromo-1-methyl-1H-pyrrolo[3,2-b]pyridine

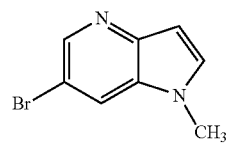

A solution of 6-bromo-1H-pyrrolo[3,2-b]pyridine (54 kg from multiple batches based on wt % assay, 274 mol) in ethyl acetate from the previous step was distilled under vacuum at 45±5° C. to a volume of about 110 L (2 L/kg) and then cooled to 25±5° C. Dimethylcarbonate (33.0 kg, 367 mol) and Et₃N (22.0 kg, 217 mol) were added and the mixture was distilled under vacuum at 50±5° C. to a volume of about 85 L. N,N-dimethylformamide (82.5 kg, 1.6 L/kg) was added and the mixture was distilled under vacuum at 50±5° C. until no distillate was observed. The mixture was cooled to 25±5° C., and dimethylcarbonate (165 kg, 1833 mol), Et₃N (60.5 kg, 598 mol), and tetrabutylammonium bromide (11.0 kg) were added. The reaction mixture was heated to 88±5° C. After 12 hours at 105-110° C. (jacket temperature), which corresponded to 83-85° C. reaction mixture temperature, HPLC analysis indicated 59.6% of the starting material remained. The jacket temperature was increased to 115-120° C. (corresponding to 84-87° C. reaction mixture temperature). After 18 hours at 115-120° C. (jacket temperature) HPLC analysis indicated 0.2% of the starting material remained. The mixture was cooled to 25° C. and then concentrated under vacuum at 55±5° C. to remove most of the dimethylcarbonate and Et₃N. Next, the mixture was cooled to 25° C. and MTBE (340 kg) was added, followed by water (440 kg). The mixture was stirred for 30 minutes. Stirring was stopped and the mixture was left for 30 minutes for phase separation to occur. The aqueous phase was extracted with MTBE (2×209 kg). The MTBE phases were combined and washed with brine solution (286 kg). Activated charcoal (2.7 kg) was added to the organic phase, which was stirred for 1 hour and then filtered through a pad of Celite. The filter cake was washed with MTBE (55 kg). The organic layers were combined (750 kg, 6.45% by HPLC-assay) and distilled to dryness to obtain the title compound as yellow oil (48.4 kg). The product was used directly in the next step without further purification.

Step D:
6-Bromo-1-methyl-1H-pyrrolo[3,2-b]pyridine 4-oxide

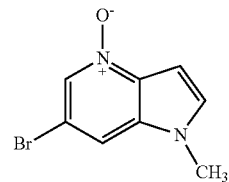

To a 1000 L vessel equipped with mechanical stirring was added DCM (510.0 kg) and 6-bromo-1-methyl-1H-pyrrolo[3,2-b]pyridine (48.0 kg, 227 mol) at room temperature. The mixture was cooled to 5±5° C. An oxidizing agent, m-CPBA (85%) (74.8 kg) was slowly added while maintaining the temperature below 10° C. (10 portions over 6 hours). The mixture was stirred for 1 hour, warmed slowly to 25±5° C., and then stirred at this temperature for 4 hours. A solution of Na₂S₂O₃ (38.5 kg) in water (154 kg) was added to the reaction mixture and the contents of the vessel were stirred for 1 hour. The organic layer was separated and the aqueous layer was extracted with DCM (256 kg). The organic layers were combined and additional DCM (200 kg) and K₂CO₃ (94.5 kg) were added. The resulting mixture was stirred for 5 hours and filtered to obtain a first filtrate (760 kg). The filter cake was slurried in DCM (526 kg) for 6.5 hours and filtered. The filter cake was washed with DCM (64 kg) to obtain a second filtrate (482 kg). Potassium carbonate (50.0 kg) was added to the first filtrate (760 kg). The mixture was stirred at RT for 20 hours and then filtered. The filter cake was washed with DCM (62 kg) to obtain a third filtrate (704 kg). The filter cake was then slurried for 3 hours in the second filtrate (482 kg) and filtered. The filter cake was washed with DCM (64 kg) to obtain a fourth filtrate (494 kg). The third filtrate and the fourth filtrate give the title compound as a solution in DCM (42.8 kg based on assay).

Step E: 6-Bromo-1-methyl-1H-pyrrolo[3,2-b]pyridine-5-carbonitrile

A solution of 6-bromo-1-methyl-1H-pyrrolo[3,2-b]pyridine 4-oxide (42.8 kg, 188 mol) in DCM from the previous step was distilled at 45° C. to a volume of about 85 L. Acetonitrile (100 kg) was added and the mixture was distilled at 45° C. to a volume of about 110 L (2.5 L/kg). More ACN (80 kg) was added and the mixture was again distilled at 45° C. to a volume of about 110 L. Triethylamine (80 kg, 791 mol) was added. The mixture was cooled to 10±5° C. and trimethylsilyl cyanide (81.6 kg, 822 mol) was added over the course of 15 minutes while maintaining the temperature of the mixture below 25° C. The reaction mixture was gradually heated to 70±5° C. After stirring for 10 hours at this temperature, the starting material was consumed. The reaction mixture was cooled to 10±5° C. A 20% aqueous $K_2CO_3$ solution (260 kg) was added and the mixture was stirred at 10±5° C. for 1 hour. The resulting precipitate was filtered. The reactor was rinsed with a 2.3% aqueous $K_2CO_3$ solution (133 kg). The rinse was used to wash the filter cake, which was slurried in water (180 kg) for 30 minutes and filtered. The filter cake was again slurried in water (180 kg) for 30 minutes and filtered. The filtered solids were dispersed in a solution of DCM (1166 kg) and THF (156 kg). The mixture was stirred for 2 hours at 30±5° C. Activated carbon (7.0 kg, 0.16 kg/kg) was added and the mixture was stirred at 30±5° C. for 2 hours and filtered through a pad of Celite under pressure. The reactor was rinsed with DCM (200 kg) and the rinse was used to wash the filter cake. The combined filtrate was distilled at 40±5° C. to a volume of about 170 L. Next, n-heptane (120 kg) was added to the mixture, which was concentrated by distillation at 40±5° C. to a volume of about 170 L. More n-heptane (238 kg) was added to the mixture. The slurry was cooled to 5±5° C. and stirred for 1 hour. The resulting precipitate was filtered under pressure and the filter cake was washed with n-heptane (68 kg) from the reactor rinse. The wet cake was dried under vacuum at 40° C. for 20 hours to give the title compound as an off-white solid (34.2 kg).

Preparation x3: 1-Methyl-6-morpholino-1H-pyrrolo[3,2-b]pyridine-5-carbonitrile

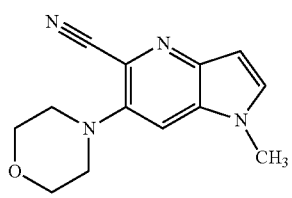 [SMILES: Cn1ccc2nc(C#N)c(N3CCOCC3)cc21]

Tris(dibenzylideneacetone)dipalladium (0) (1.940 g, 2.118 mmol), racemic-2,2'-bis(diphenylphosphino)-1,1'-binaphthyl (2.64 g, 4.24 mmol), 6-bromo-1-methyl-1H-pyrrolo[3,2-b]pyridine-5-carbonitrile (10 g, 42.4 mmol), and sodium tert-butoxide (6.30 g, 63.5 mmol) were added to a 500 mL round-bottomed flask. The vessel was evacuated and flushed with nitrogen (3×) and the solids were dispersed in THF (200 mL). The red mixture was heated to 72° C. for 13 hours. After cooling to room temperature, EtOAc (300 mL) was added and the mixture was passed through a short pad of Celite. The filtrate was concentrated in vacuo, and the residue was re-suspended in EtOAc (75 mL). The mixture was heated gently with stirring to dislodge most of the solids adhered to the glass, and the pink solid phase was collected by vacuum filtration on a fritted glass funnel. The solids were washed with 50% EtOAc/ether (2×) and water to give a first crop of product (6.7 g). The filtrate was concentrated and reconstituted in EtOAc. The insoluble solids were removed by filtration. The filtrate was reduced in volume to about 25 mL, which crystallized additional product that was collected on a fritted glass funnel and washed with EtOAc/ether and ether (1.6 g). The two crops were combined to give the title compound (8.3 g, 81%). $^1$H NMR (500 MHz, $CDCl_3$) δ ppm 7.34 (d, 1H, J=3.5 Hz), 7.27 (s, 1H), 6.67 (d, 1H, J=3.5 Hz), 3.96 (t, 4H, J=4.5 Hz), 3.82 (s, 3H), 3.18 (t, 4H, J=4.5 Hz); ESI-MS m/z $[M+H]^+$ calc'd for $C_{13}H_{14}N_4O$, 243. found 243.

Preparation x4: 1-(1-Methyl-6-morpholino-1H-pyrrolo[3,2-b]pyridin-5-yl)ethanamine

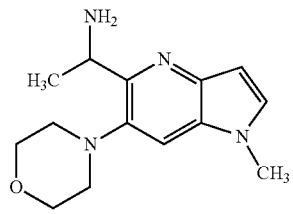 [SMILES: CC(N)c1nc2ccn(C)c2cc1N1CCOCC1]

Methylmagnesium bromide (3.0 M in THF, 0.60 mL, 1.8 mmol) was added to a stirred solution of 1-methyl-6-morpholino-1H-pyrrolo[3,2-b]pyridine-5-carbonitrile (145 mg, 0.60 mmol) in dry THF (6 mL) at RT. The reaction mixture was stirred for 1 h, then cooled to 0° C. and quenched with MeOH (5 mL). Sodium borohydride (45 mg, 1.2 mmol) was added. The reaction mixture was stirred for 20 minutes, quenched with 1N HCl (1.5 mL), and stirred for an additional 20 minutes. Next, the solution was diluted with saturated aqueous $NaHCO_3$ and extracted with EtOAc (6×). The organic layers were combined, dried over $MgSO_4$, and concentrated to give the title compound as a yellow oil (83%). $^1$H NMR (500 MHz, $CD_3OD$) δ ppm 7.83 (s, 1H), 7.46 (d, 1H, J=3.5 Hz), 6.56 (d, 1H, J=3.5 Hz), 4.97 (q, 1H, J=7.0 Hz), 3.83-3.90 (m, 4H), 3.84 (s, 3H), 3.01-3.07 (m, 2H), 2.88-2.94 (m, 2H), 1.54 (d, 3H, J=7.0 Hz); ESI-MS m/z $[M+H]^+$ calc'd for $C_{14}H_{20}N_4O$, 261; found 261.

Preparation x5: tert-Butyl (1-(6-bromo-1-methyl-1H-pyrrolo[3,2-b]pyridin-5-yl)ethyl)carbamate

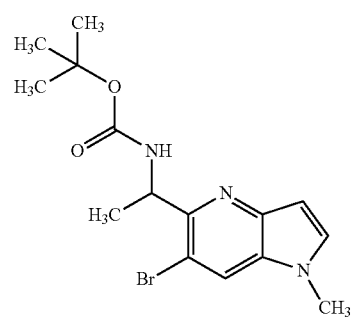 [SMILES: CC(NC(=O)OC(C)(C)C)c1nc2ccn(C)c2cc1Br]

Methylmagnesium bromide (187 mL, 262 mmol) was added slowly, with stirring over a period of about 30 minutes, to a chilled solution of 6-bromo-1-methyl-1H-pyrrolo[3,2-b]pyridine-5-carbonitrile (7.74 g, 32.8 mmol) and THF (500 mL) in an ice bath. The reaction mixture was subsequently removed from the ice bath and stirred at room temperature for 2 hours. The mixture was then cooled in an ice bath and anhydrous MeOH (200 mL) was slowly added to quench excess CH₃MgBr. After stirring at room temperature for 30 minutes, sodium borohydride (4.96 g, 131 mmol) was added in one addition and the reaction mixture was stirred for another 30 minutes. Ice/water (200 mL) was added slowly to the mixture, which was stirred at room temperature for 20 minutes. Next, di-tert-butyl dicarbonate (21.47 g, 98 mmol) and N-ethyl-N-isopropylpropan-2-amine (5.89 mL, 32.8 mmol) were added to the solution and the mixture was stirred at room temperature for 2-3 hours. The mixture was diluted with EtOAc (500 mL) and saturated NaHCO₃ (1000 mL). The organic layer was separated and the aqueous layer was washed with additional EtOAc (2×500 mL). The combined organic layers were dried over MgSO₄ and concentrated. The residue was purified by flash column chromatography (10% EtOAc in hexanes for 40 minutes, followed by 20-40% EtOAc gradient in hexanes over 60 minutes) to give the title compound as a white solid (7.9 g, 68%). ¹H NMR (500 MHz, DMSO-d₆) δ ppm 1.09-1.42 (m, 12 H), 3.80 (s, 3 H), 5.15 (quin, J=7.08 Hz, 1 H), 6.55 (d, J=2.93 Hz, 1 H), 6.96 (d, J=7.81 Hz, 1 H), 7.65 (d, J=2.93 Hz, 1 H), 8.21 (s, 1 H).

Preparation x6: (S)-tert-Butyl (1-(6-bromo-1-methyl-1H-pyrrolo[3,2-b]pyridin-5-yl)ethyl)carbamate and (R)-tert-butyl (1-(6-bromo-1-methyl-1H-pyrrolo[3,2-b]pyridin-5-yl)ethyl)carbamate

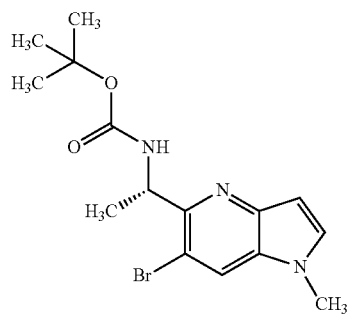

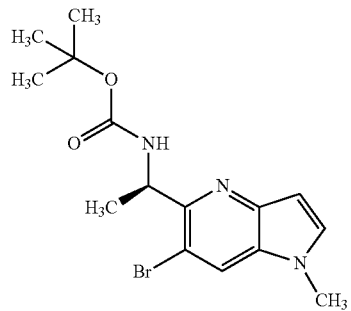

Racemic tert-butyl (1-(6-bromo-1-methyl-1H-pyrrolo[3,2-b]pyridin-5-yl)ethyl)carbamate was resolved by supercritical fluid chromatography (ChiralPak™ AD-H, 20×200 mm) eluting with 10% MeOH in liquid CO₂ flowing at 60 mL/min over a 5-minute period. The stereoisomer contained in fractions collected at the later retention time was assigned S stereochemical configuration, and the stereoisomer contained in fractions collected at the earlier retention time was assigned R stereochemical configuration. ¹H NMR and LC/MS for each enantiomer are consistent with PREPARATION x5.

Preparation x7: (S)-1-(1-Methyl-6-(1-methyl-1H-pyrazol-5-yl)-1H-pyrrolo[3,2-b]pyridin-5-yl)ethanamine

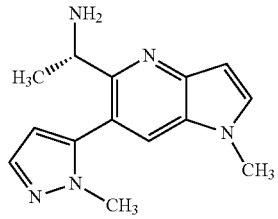 [SMILES: C[C@H](N)c1nc2ccn(C)c2cc1-c1ccnn1C]

A solution of (S)-tert-butyl (1-(6-bromo-1-methyl-1H-pyrrolo[3,2-b]pyridin-5-yl)ethyl)carbamate (1 g, 2.82 mmol), tetrakis(triphenylphosphine)palladium (0) (0.163 g, 0.141 mmol) and 1-methyl-5-(4,4,5,5-tetramethyl-1,3,2-dioxaborolan-2-yl)-1H-pyrazole (1.175 g, 5.65 mmol) in dioxane/saturated NaHCO₃ (1:1, 10 mL) was heated to 120° C. in a microwave reactor. After cooling to room temperature, solvent was removed, and the reaction mixture was purified by silica gel column chromatography with a 20-80% EtOAc gradient in hexane over 2 hours. The desired fractions were collected and solvent was removed in vacuo. The resulting residue was dissolved in dioxane (50 mL) and a 1M solution of HCl in dioxane (50 mL) was added. The mixture was stirred at room temperature overnight. Solvent was removed and the residue was suspended in ether and filtered. The solids were washed with ether and dried to give an HCl salt of the title compound as an off-white solid. ¹H NMR (500 MHz, DMSO-d₆) δ ppm 1.33 (d, J=6.35 Hz, 3 H), 3.68 (s, 3 H), 3.85 (s, 3 H), 4.28 (br s, 1 H), 6.45 (d, J=1.95 Hz, 1 H), 6.65-6.70 (m, 1 H), 7.59 (s, 1 H), 7.85 (d, J=2.93 Hz, 1 H), 8.05 (s, 1 H), 8.35 (br s, 3 H); ESI-MS m/z [M+H]⁺ calc'd for C₁₄H₁₇N₅, 256; found 256.

Preparation x8: (S)-2,5-Dichloro-N-(1-(1-methyl-6-(1-methyl-1H-pyrazol-5-yl)-1H-pyrrolo[3,2-b]pyridin-5-yl)ethyl)pyrimidin-4-amine

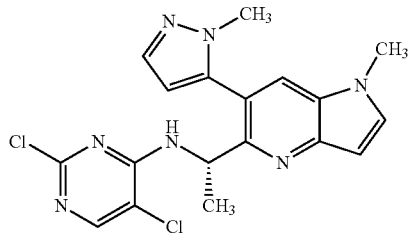 [SMILES: C[C@H](Nc1nc(Cl)ncc1Cl)c1nc2ccn(C)c2cc1-c1ccnn1C]

(S)-1-(1-Methyl-6-(1-methyl-1H-pyrazol-5-yl)-1H-pyrrolo[3,2-b]pyridin-5-yl)ethanamine (20 mg, 0.078 mmol), 2,4,5-trichloropyrimidine (13.47 μL, 0.118 mmol), and N-ethyl-N-isopropylpropan-2-amine (42.2 μL, 0.235 mmol) were combined in acetonitrile (499 μL). The resulting mixture was heated to 120° C. in a microwave reactor for 1 hour, then concentrated and purified by preparative HPLC (20% to 45% ACN/water with 0.03% TFA) to give a TFA salt of the title compound as a white solid (1 mg, 3.17%). ¹H NMR (500 MHz, CD₃OD) δ ppm 1.61 (d, J=7.32 Hz, 3 H), 3.83 (s, 3 H), 4.01 (s, 3 H), 5.36-5.44 (m, 1 H), 6.66 (s, 1 H), 6.79-6.82 (m, 1 H), 7.67 (d, J=2.44 Hz, 1 H), 7.95 (d, J=2.93 Hz, 1 H), 8.15

(s, 1 H), 8.36 (s, 1 H); ESI-MS m/z [M+H]+ calc'd for $C_{18}H_{17}Cl_2N_7$, 402.09; found 402.3.

Preparation x9: (S)-4-Amino-6-((1-(1-methyl-6-(1-methyl-1H-pyrazol-5-yl)-1H-pyrrolo[3,2-b]pyridin-5-yl)ethyl)amino)-2-(methylthio)pyrimidine-5-carbonitrile

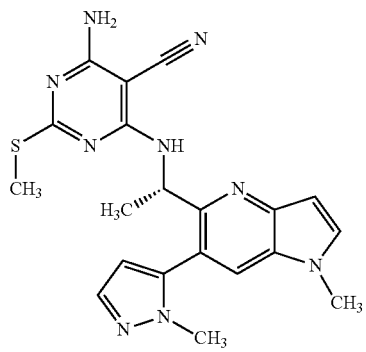 [SMILES: CSc1nc(N)c(C#N)c(N[C@@H](C)c2nc3ccn(C)c3cc2-c2ccnn2C)n1]

Step A: (S)-4-Chloro-6-((1-(1-methyl-6-(1-methyl-1H-pyrazol-5-yl)-1H-pyrrolo[3,2-b]pyridin-5-yl)ethyl)amino)-2-(methylthio)pyrimidine-5-carbonitrile

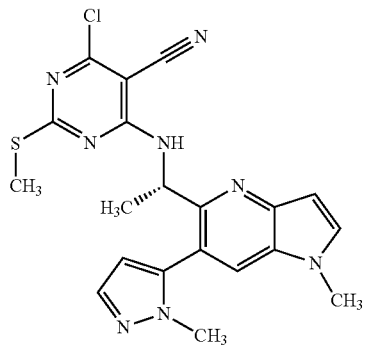 [SMILES: CSc1nc(Cl)c(C#N)c(N[C@@H](C)c2nc3ccn(C)c3cc2-c2ccnn2C)n1]

(S)-1-(1-Methyl-6-(1-methyl-1H-pyrazol-5-yl)-1H-pyrrolo[3,2-b]pyridin-5-yl)ethanamine 2,2,2-trifluoroacetate (1562 mg, 4.23 mmol) in THF (27.5 mL) along with 4,6-dichloro-2-(methylthio)pyrimidine-5-carbonitrile (931 mg, 4.23 mmol) and $Et_3N$ (1297 μL, 9.31 mmol) were added to a pear-shaped flask. The resulting mixture was stirred at room temperature for 2 hours and then concentrated to give the title compound, which was used in next step without further purification. ESI-MS m/z [M+H]+ calc'd for $C_{20}H_{19}ClN_8S$, 439.11. found 439.4.

Step B: (S)-4-Amino-6-((1-(1-methyl-6-(1-methyl-1H-pyrazol-5-yl)-1H-pyrrolo[3,2-b]pyridin-5-yl)ethyl)amino)-2-(methylthio)pyrimidine-5-carbonitrile A mixture of (S)-4-chloro-6-((1-(1-methyl-6-(1-methyl-1H-pyrazol-5-yl)-1H-pyrrolo[3,2-b]pyridin-5-yl)ethyl)amino)-2-(methylthio)pyrimidine-5-carbonitrile (1.857 g, 4.23 mmol) and ammonium hydroxide (0.494 mL, 12.69 mmol) was heated at 85° C. in a microwave reactor for 12 hours. Additional ammonium hydroxide (0.494 mL, 12.69 mmol) was added. The reaction mixture was heated at 85° C. in a microwave reactor for 6 hours and then concentrated to give the title compound, which was used without further purification. ESI-MS m/z [M+H]+ calc'd for $C_{20}H_{21}N_9S$, 420.16; found 420.4.

Preparation x10: (S)-4-Amino-6-((1-(1-methyl-6-(1-methyl-1H-pyrazol-5-yl)-1H-pyrrolo[3,2-b]pyridin-5-yl)ethyl)amino)-2-(methylsulfonyl)pyrimidine-5-carbonitrile

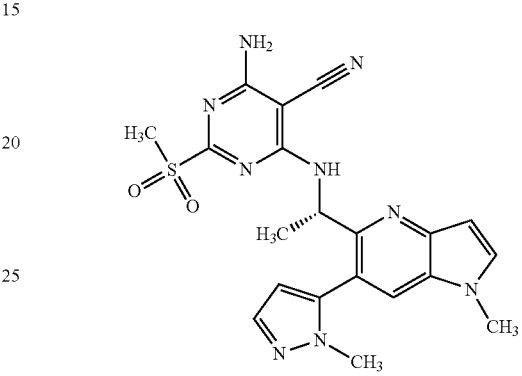

To a round-bottomed flask was added (S)-4-amino-6-((1-(1-methyl-6-(1-methyl-1H-pyrazol-5-yl)-1H-pyrrolo[3,2-b]pyridin-5-yl)ethyl)amino)-2-(methylthio)pyrimidine-5-carbonitrile (200 mg, 0.477 mmol) in acetonitrile (5418 μL) and water (5418 μL). The mixture was cooled to 0° C. Oxone® (733 mg, 1.192 mmol) was added to give an orange solution. The reaction mixture was stirred at 0° C. for 30 min and then allowed to warm to room temperature. After 2 h, LCMS showed the reaction to be complete. The reaction mixture was subsequently diluted with EtOAc and washed with brine (3×). The combined organic layers were dried over $Na_2SO_4$, filtered, and concentrated to give the title compound as a yellow solid. ESI-MS m/z [M+H]+ calc'd for $C_{20}H_{21}N_9O_2S$, 452.15; found 452.4.

Preparation x11: (S)-4-Methyl-6-((1-(1-methyl-6-(1-methyl-1H-pyrazol-5-yl)-1H-pyrrolo[3,2-b]pyridin-5-yl)ethyl)amino)-2-(methylsulfonyl)pyrimidine-5-carbonitrile

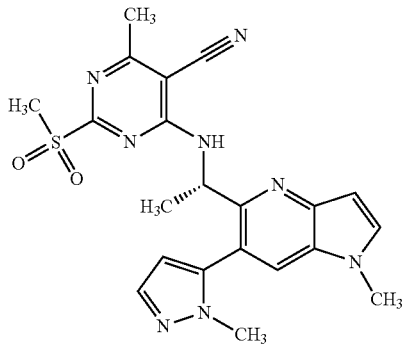 [SMILES: Cc1nc(S(C)(=O)=O)nc(N[C@@H](C)c2nc3ccn(C)c3cc2-c2ccnn2C)c1C#N]

Step A: (S)-4-Methyl-6-((1-(1-methyl-6-(1-methyl-1H-pyrazol-5-yl)-1H-pyrrolo[3,2-b]pyridin-5-yl)ethyl)amino)-2-(methylthio)pyrimidine-5-carbonitrile

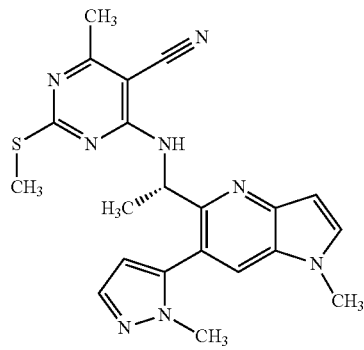 [SMILES: CSc1nc(C)c(C#N)c(N[C@@H](C)c2nc3ccn(C)c3cc2-c2ccnn2C)n1]

To a round bottomed flask was added (S)-1-(1-methyl-6-(1-methyl-1H-pyrazol-5-yl)-1H-pyrrolo[3,2-b]pyridin-5-yl)ethanamine 2,2,2-trifluoroacetate (364 mg, 0.986 mmol) in THF (6400 µL) along with 4-chloro-6-methyl-2-(methylthio)pyrimidine-5-carbonitrile (197 mg, 0.986 mmol) and Et$_3$N (302 µL, 2.168 mmol). The reaction mixture was stirred at room temperature overnight and was subsequently purified on silica, eluting with a gradient of EtOAc/hexanes (2:8 to 9:1) to give the title compound as a clear film (270 mg, 65.5%). ESI-MS m/z [M+H]$^+$ calc'd for C$_{21}$H$_{22}$N$_8$S 419.17; found 419.4.

Step B: (S)-4-methyl-6-((1-(1-methyl-6-(1-methyl-1H-pyrazol-5-yl)-1H-pyrrolo[3,2-b]pyridin-5-yl)ethyl)amino)-2-(methylsulfonyl)pyrimidine-5-carbonitrile To a round-bottomed flask was added (S)-4-methyl-6-((1-(1-methyl-6-(1-methyl-1H-pyrazol-5-yl)-1H-pyrrolo[3,2-b]pyridin-5-yl)ethyl)amino)-2-(methylthio)pyrimidine-5-carbonitrile (170 mg, 0.406 mmol) in acetonitrile (4616 µL) and water (4616 µL). The mixture was cooled to 0° C. and Oxone® (624 mg, 1.015 mmol) was added. The reaction mixture was stirred at 0° C. for 30 min and then allowed to warm to room temperature. After 4 hours the reaction mixture was diluted with EtOAc and washed with brine (3×). The combined organic layers were dried over Na$_2$SO$_4$, filtered, and concentrated to give the title compound as a yellow solid. ESI-MS m/z [M+H]$^+$ calc'd for C$_{21}$H$_{22}$N$_8$O$_2$S, 451.16; found 451.4.

Preparation x12: (S)-2-Chloro-4-((1-(1-methyl-6-(1-methyl-1H-pyrazol-5-yl)-1H-pyrrolo[3,2-b]pyridin-5-yl)ethyl)amino)pyrimidine-5-carbonitrile

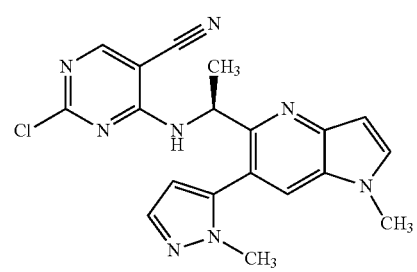 [SMILES: C[C@H](Nc1nc(Cl)ncc1C#N)c1nc2ccn(C)c2cc1-c1ccnn1C]

(S)-1-(1-Methyl-6-(1-methyl-1H-pyrazol-5-yl)-1H-pyrrolo[3,2-b]pyridin-5-yl)ethanamine 2,2,2-trifluoroacetate (100 mg, 0.271 mmol), 2,4-dichloropyrimidine-5-carbonitrile (70.7 mg, 0.406 mmol) and N-ethyl-N-isopropylpropan-2-amine (146 µL, 0.812 mmol) were combined in acetonitrile (1725 µL), and the resulting mixture was heated to 120° C. in a microwave reactor for 1 hour. The mixture was concentrated and purified on a silica gel column, eluting with EtOAc. The fractions were collected and concentrated in vacuo to give the title compound as a yellow solid (30 mg, 28%). ESI-MS m/z [M+H]$^+$ calc'd for C$_{19}$H$_{17}$ClN$_8$, 393.13; found 393.3.

Preparation x13: (S)-2-Chloro-5-fluoro-N-(1-(1-methyl-6-(1-methyl-1H-pyrazol-5-yl)-1H-pyrrolo[3,2-b]pyridin-5-yl)ethyl)pyrimidin-4-amine

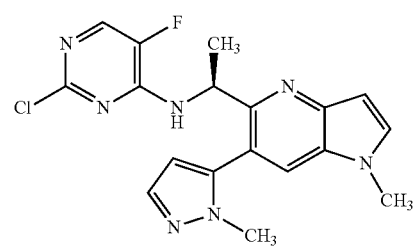 [SMILES: C[C@H](Nc1nc(Cl)ncc1F)c1nc2ccn(C)c2cc1-c1ccnn1C]

(S)-1-(1-Methyl-6-(1-methyl-1H-pyrazol-5-yl)-1H-pyrrolo[3,2-b]pyridin-5-yl)ethanamine (90 mg, 0.353 mmol), 2,4-dichloro-5-fluoropyrimidine (88 mg, 0.529 mmol), and N-ethyl-N-isopropylpropan-2-amine (190 µL, 1.058 mmol) were combined in acetonitrile (500 µL). The reaction mixture was heated to 120° C. in a microwave reactor for 1 hour. After removal of solvent, the residue was diluted with MeOH and dichloromethane, and was purified by preparative HPLC, eluting with a gradient of 15-25% ACN in H$_2$O with 0.35% TFA. The fractions were collected and solvent was removed in vacuo to give the title compound (136 mg, 100%). ESI-MS m/z [M+H]$^+$ calc'd for C$_{18}$H$_{17}$ClFN$_7$, 386; found 386.

Preparation x14: (S)-1-(1-Methyl-6-morpholino-1H-pyrrolo[3,2-b]pyridin-5-yl)ethanamine

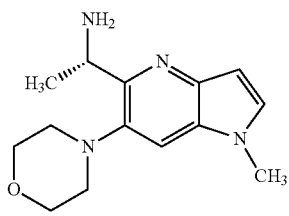 [SMILES: C[C@H](N)c1nc2ccn(C)c2cc1N1CCOCC1]

(S)-1-(6-Bromo-1-methyl-1H-pyrrolo[3,2-b]pyridin-5-yl)ethanamine (1.6 g, 6.30 mmol) was stirred with potassium tert-butoxide (2.83 g, 25.2 mmol) and morpholine (6.58 g, 76 mmol) in DME (50 mL) at 88° C. for 4 hours. The mixture was then concentrated in vacuo. The residue was taken up in acetonitrile and water, and was lyophilized to give the title compound, which was used without further purification. ESI-MS m/z [M+H]$^+$ calc'd for $C_{14}H_{20}N_4O$, 261; found 261.

Preparation x15: (S)-4-Chloro-6-((1-(1-methyl-6-morpholino-1H-pyrrolo[3,2-b]pyridin-5-yl)ethyl)amino)-2-(methylthio)pyrimidine-5-carbonitrile

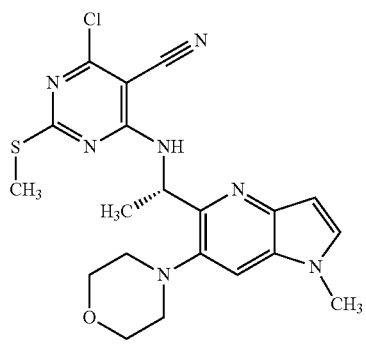 [SMILES: CSc1nc(Cl)c(C#N)c(N[C@@H](C)c2nc3ccn(C)c3cc2N2CCOCC2)n1]

(S)-1-(1-Methyl-6-morpholino-1H-pyrrolo[3,2-b]pyridin-5-yl)ethanamine (200 mg, 0.768 mmol) was dissolved in THF (5 mL) along with 4,6-dichloro-2-(methylthio)pyrimidine-5-carbonitrile (169 mg, 0.768 mmol) and Et$_3$N (0.118 mL, 0.845 mmol) to give an orange suspension. The reaction mixture was stirred at room temperature for 2 h, then diluted with ethyl acetate and washed saturated aq NH$_4$Cl (3×15 mL). The combined organic layers were dried over MgSO$_4$, filtered, and concentrated in vacuo. The crude product was then loaded onto an ISCO® silica gel cartridge (12 g) and eluted using an EtOAc/Hexane gradient. The product was collected and concentrated in vacuo to afford the title compound as a white solid (200 mg, 59%). ESI-MS m/z [M+H]$^+$ calc'd for $C_{20}H_{22}ClN_7OS$, 443.95; found 444.3.

Preparation x16: (S)-4-Amino-6-((1-(1-methyl-6-morpholino-1H-pyrrolo[3,2-b]pyridin-5-yl)ethyl)amino)-2-(methylthio)pyrimidine-5-carbonitrile

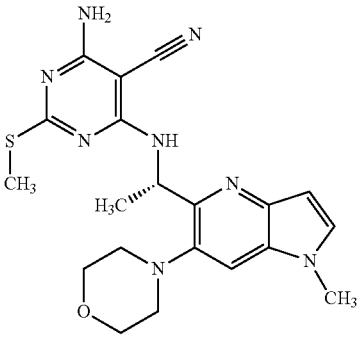 [SMILES: CSc1nc(N)c(C#N)c(N[C@@H](C)c2nc3ccn(C)c3cc2N2CCOCC2)n1]

(S)-1-(1-Methyl-6-morpholino-1H-pyrrolo[3,2-b]pyridin-5-yl)ethanamine (200 mg, 0.768 mmol) was dissolved in THF (5 mL) along with 4,6-dichloro-2-(methylthio)pyrimidine-5-carbonitrile (169 mg, 0.768 mmol) and Et$_3$N (0.118 mL, 0.845 mmol) to give an orange suspension. The reaction mixture was stirred at room temperature for 2 h, then diluted with EtOAc and washed aq 1M HCl (3×15 mL). The combined organic layers were dried over MgSO$_4$, filtered, and concentrated in vacuo. The crude product was then loaded onto an ISCO® silica gel cartridge (12 g) and eluted using an EtOAc/Hexane gradient. The product was collected and concentrated in vacuo to afford the title compound as a white solid (117 mg, 61%). $^1$H NMR (400 MHz, DMSO-d$_6$) δ ppm 1.36-1.50 (m, 3 H), 2.43-2.47 (m, 3 H), 2.72-2.88 (m, 2 H), 2.99-3.15 (m, 2 H), 3.68-3.89 (m, 7 H), 5.89-6.02 (m, 1 H), 6.46-6.58 (m, 1 H), 7.04-7.18 (m, 1 H), 7.21-7.42 (m, 2 H), 7.53-7.65 (m, 1 H), 7.82-7.95 (m, 1 H); ESI-MS m/z [M+H]$^+$ calc'd for $C_{20}H_{24}N_8OS$, 425.5; found 425.5.

Preparation x17: (S)-4-Amino-6-((1-(1-methyl-6-morpholino-1H-pyrrolo[3,2-b]pyridin-5-yl)ethyl)amino)-2-(methylsulfonyl)pyrimidine-5-carbonitrile

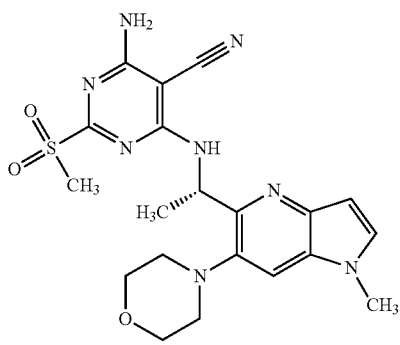 [SMILES: C[C@H](Nc1nc(S(C)(=O)=O)nc(N)c1C#N)c1nc2ccn(C)c2cc1N1CCOCC1]

(S)-4-Amino-6-((1-(1-methyl-6-morpholino-1H-pyrrolo[3,2-b]pyridin-5-yl)ethyl)amino)-2-(methylthio)pyrimidine-5-carbonitrile (287 mg, 0.676 mmol) in acetonitrile (3 mL) and H$_2$O (3 mL) was cooled to 0° C. Oxone® (1.04 g, 1.690 mmol) was added to give a yellow solution. The reaction mixture was stirred at 0° C. for 30 minutes, warmed to room temperature, and stirred for an additional 3 hours. The reaction mixture was subsequently diluted with EtOAc and washed with H₂O (3×5 mL). The combined organic layers were dried over MgSO₄, filtered, and concentrated in vacuo to give the title compound, which was used without further purification.

Preparation x18: (S)-4-Methyl-6-((1-(1-methyl-6-morpholino-1H-pyrrolo[3,2-b]pyridin-5-yl)ethyl)amino)-2-(methylthio)pyrimidine-5-carbonitrile

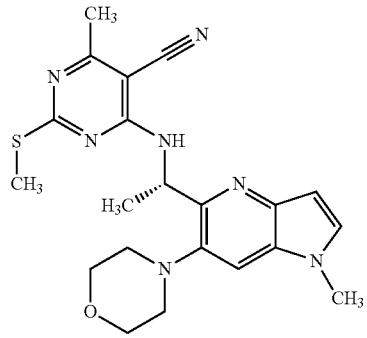 [SMILES: CSc1nc(C)c(C#N)c(N[C@@H](C)c2nc3ccn(C)c3cc2N2CCOCC2)n1]

(S)-1-(1-Methyl-6-morpholino-1H-pyrrolo[3,2-b]pyridin-5-yl)ethanamine (100 mg, 0.384 mmol), 4-chloro-6-methyl-2-(methylthio)pyrimidine-5-carbonitrile (77 mg, 0.384 mmol) and Et₃N (0.059 mL, 0.423 mmol) in DMF (2 mL) were combined to give a yellow solution. The reaction mixture was stirred overnight at room temperature. The product was purified by LC/MS using a 15-40% CH₃CN gradient in H₂O with 0.035% formic acid. The pure fractions were combined and lyophilized to afford the title compound as a white solid (109 mg, 67%). ¹H NMR (400 MHz, DMSO-d₆) δ ppm 1.22-1.26 (s, 3 H), 1.50-1.65 (m, 3H), 2.40 (s, 3 H), 2.81-2.91 (m, 2 H), 3.07-3.20 (m, 2 H), 3.74-3.79 (m, 4 H), 3.82 (s, 3H), 5.88-6.00 (m, 1 H), 6.58-6.69 (m, 1 H), 7.76-8.07 (m, 1 H), 7.74-7.78 (m, 1 H), 7.85 (s, 1 H); ESI-MS m/z [M+H]⁺ calc'd for C₂₁H₂₅N₇OS, 424.5; found 424.5.

Preparation x19: (S)-4-Methyl-6-((1-(1-methyl-6-morpholino-1H-pyrrolo[3,2-b]pyridin-5-yl)ethyl)amino)-2-(methylsulfonyl)pyrimidine-5-carbonitrile

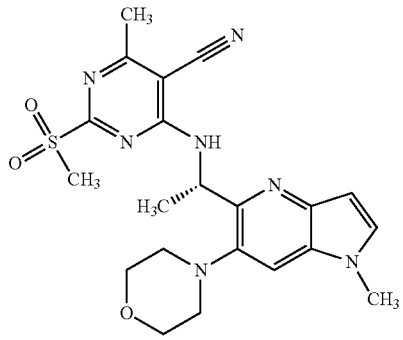 [SMILES: Cc1nc(S(C)(=O)=O)nc(N[C@@H](C)c2nc3ccn(C)c3cc2N2CCOCC2)c1C#N]

A mixture of (S)-4-methyl-6-((1-(1-methyl-6-morpholino-1H-pyrrolo[3,2-b]pyridin-5-yl)ethyl)amino)-2-(methylthio)pyrimidine-5-carbonitrile (197 mg, 0.465 mmol) in acetonitrile (2 mL) and H₂O (2 mL) was cooled to 0° C. Oxone® (715 mg, 1.163 mmol) was added to give an orange suspension. The reaction mixture was stirred at 0° C. for 30 minutes, warmed to room temperature, and stirred for an additional 3 hours. The reaction mixture was subsequently diluted with EtOAc and washed with H₂O (3×5 mL). The combined organic layers were dried over MgSO₄, filtered, and concentrated in vacuo to give the title compound, which was used without further purification.

Preparation x20: (S)-1-(1-Methyl-6-(pyridin-2-yl)-1H-pyrrolo[3,2-b]pyridin-5-yl)ethanamine

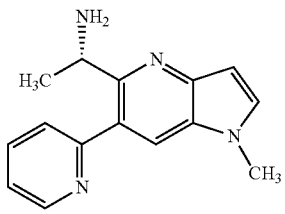 [SMILES: C[C@H](N)c1nc2ccn(C)c2cc1-c1ccccn1]

A solution of (S)-tert-butyl (1-(6-bromo-1-methyl-1H-pyrrolo[3,2-b]pyridin-5-yl)ethyl)carbamate (4 g, 11.29 mmol), 2-(trimethylstannyl) pyridine (2.73 g, 11.29 mmol) and tetrakis(triphenylphosphine) palladium(0) (0.130 g, 0.113 mmol) in dioxane (100 mL) was heated to 130° C. for 24 hours. After removal of solvent, the residue was dissolved in MeOH/DCM, treated with silica gel, and purified by column chromatography using a gradient of 20-80% EtOAc in hexane over a 60 minute period. The desired fractions were collected and solvent was evaporated in vacuo. The residue was dissolved in THF and 4M HCl in dioxane was added. The mixture was stirred at room temperature for 2 hours. Most of the solvent was removed in vacuo, and the residue was diluted in ether. The precipitate was filtered and washed with ether to give an HCl salt of the title compound (857.8 mg, 26.3%). ESI-MS m/z [M+H]⁺ calc'd for C₁₅H₁₆N₄, 236; found 236.

Preparation x21: (S)-1-(1-Methyl-6-morpholino-1H-pyrrolo[3,2-b]pyridin-5-yl)ethanamine

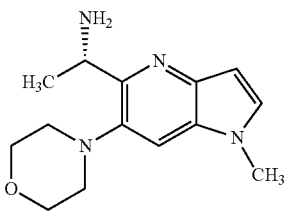 [SMILES: C[C@H](N)c1nc2ccn(C)c2cc1N1CCOCC1]

Step A: 1-(6-Bromo-1-methyl-1H-pyrrolo[3,2-b]pyridin-5-yl)ethan-1-amine

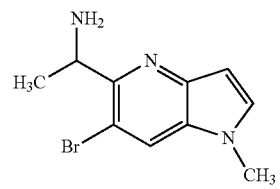

To a first vessel charged with toluene (5.1 L) was added 6-bromo-1-methyl-1H-pyrrolo[3,2-b]pyridine-5-carbonitrile (300 g, 1.27 mol) under nitrogen. The solution was cooled to 5-10° C. A 3M solution of CH₃MgCl in THF (637 mL, 1.91 mol) was added slowly over a 35 minute period while maintaining the temperature of the reaction mixture below 30° C. The reaction mixture was stirred for 2 hours at 15-20° C. To a second vessel charged with methanol at 0-5° C. was added sodium methylate (24.4 mL) under nitrogen. Sodium borohydride (72.2 g, 1.91 mol) was added to the methanol solution portion-wise over a 20 minute period at 0-5° C. The borohydride solution was stirred for 1 hour. The contents of the first vessel were then transferred into the second vessel slowly over a 2 hour period while maintaining the temperature of the reaction mixture in the second vessel below 30° C. Following the transfer of the Grignard solution, the first vessel was rinsed with toluene (0.60 L) which was added to the second vessel. The first vessel was next charged with methanol (0.60 L) over a 10 minute period at a temperature less than 30° C. The methanol solution was subsequently transferred to the second vessel, and the reaction mixture was stirred at 0-5° C. for an additional 2 hours. The reaction mixture was then transferred into a third vessel charged with a 2M HCl solution (2.40 L) at 5-15° C. over a period of 1.25 hours. Following the transfer, the second vessel was rinsed with toluene (0.60 L), which was added to the third vessel, and the reaction mixture was stirred for 16 hours. The mixture was warmed to 40-45° C. and 2M NaOH (1.0 L) was added slowly over a 20 minute period until the pH of the aqueous phase was 8.5. The reaction mixture was stirred for an additional 40 minutes, and the pH of the aqueous phase was confirmed to be 8.5. The organic and aqueous phases were separated. The aqueous phase was extracted with toluene (2×3.0 L). The organic layers were combined and screened to remove particulates. The filtrate was concentrated under vacuum at 50° C. until distillation ceased. Isopropanol (3.0 L) was added, and the reaction mixture concentrated under vacuum at 50° C. Additional isopropanol (300 mL) was added to give the title compound as a solution in IPA (230.7 g by gravimetric assay).

Step B: (S)-1-(6-Bromo-1-methyl-1H-pyrrolo[3,2-b]pyridin-5-yl)ethan-1-amine

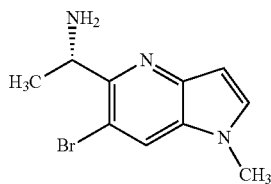

Ortho-chloro-D-tartranilic acid (i.e., (2S,3S)-4-((2-chlorophenyl)amino)-2,3-dihydroxy-4-oxobutanoic acid) (177.5 g, 683.6 mmol) was suspended in water (367 mL) and isopropanol (1.43 L). The mixture was warmed to 40-45° C. over a period of 10 minutes. A solution of 1-(6-bromo-1-methyl-1H-pyrrolo[3,2-b]pyridin-5-yl)ethan-1-amine (170 g, 669 mmol) in IPA was added slowly over a period of 10 minutes while maintaining the temperature of the reaction mixture at 35-45° C. The transfer vessel was rinsed with IPA (100 mL). The IPA rinse was added to the reaction mixture, which was then warmed to 80-85° C. and stirred at this temperature for 15 minutes. The mixture was cooled to 70-75° C. over a period of 30 minutes and a seed of ortho-chloro-D-tartranilic acid salt of (S)-1-(6-bromo-1-methyl-1H-pyrrolo[3,2-b]pyridin-5-yl)ethan-1-amine (350 mg) was added. The reaction mixture was maintained at 70-75° C. for an additional 20 minutes before cooling the mixture to 60-65° C. over a period of 45 minutes. The reaction mixture was maintained at 60-65° C. with stirring for 2 hours before slowly cooling the mixture to 20° C. over a period of 9 hours. The mixture was stirred for 8 hours at 20° C. and then filtered. The solid product was washed with IPA/water (9:1 v/v, 2×510 mL) and then re-suspended in IPA/water (9:1 v/v, 1.19 L). The mixture was warmed to 40-45° C. and maintained at this temperature for 2 hours. The suspension was slowly cooled to 20° C. over a 1 hour period and maintained at 20° C. for 1.5 hours. The reaction mixture was filtered, washed with IPA/water (9:1 v/v, 595 mL), and dried under vacuum at 40° C. to give ortho-chloro-D-tartranilic acid salt of the title compound as a white solid (115.3 g, 99.1% de, 99.6% purity by HPLC).

To a 500-mL vessel equipped with an overhead stirrer were added ortho-chloro-D-tartranilic acid salt of (S)-1-(6-bromo-1-methyl-1H-pyrrolo[3,2-b]pyridin-5-yl)ethan-1-amine (50.0 g, 97.3 mmol) followed by 2-methyltetrahydrofuran (250 mL). The resulting slurry was cooled to 15° C. An aqueous 45 wt % KOH solution (36.4 g, 0.292 mol, 3.0 eq) diluted with water (125 mL) was added. The resulting biphasic solution was stirred for three minutes. The organic and aqueous phases were separated. The aqueous phase was extracted with 2-methyltetrahydrofuran (250 mL). The aqueous phase contained 2.5% of amine. The organic extracts, which contained 4.4% H₂O by Karl Fischer analysis, were combined and distilled at 95° C. and atmospheric pressure to give the title compound as a solution in 2-methyltetrahydrofuran (125 mL; 98.8% purity and 0.5% of 2-chloroaniline by HPLC; 0.2% H₂O by KF).

Step C: (S)-1-(1-Methyl-6-morpholino-1H-pyrrolo[3,2-b]pyridin-5-yl)ethan-1-amine To a 100-mL three-neck round bottom flask equipped with an overhead stirrer, thermocouple, and condenser with gas inlet for nitrogen, was charged with KOt-Bu (95%, 8.3 g, 70.40 mmol, 4.0 eq) and 2-methyltetrahydrofuran (36 mL) followed by morpholine (18.5 mL, 210.6 mmol, 12.0 eq). The mixture was heated to 90-95° C. and then a solution of (S)-1-(6-bromo-1-methyl-1H-pyrrolo[3,2-b]pyridin-5-yl)ethan-1-amine (4.46 g, 210.6 mmol) in 2-methyltetrahydrofuran (9 mL) was added dropwise via a syringe pump over a period of one hour. Following addition of the amine, the transfer vessel was rinsed with 2-methyltetrahydrofuran (5 mL). The rinse was added to the reaction mixture, which was stirred at reflux for one hour. HPLC analysis indicated the reaction was complete. The slurry was then cooled to 60° C. and water (15 mL) was added, which dissolved the solids. The organic and aqueous phases were separated at 40-50° C. The aqueous phase was extracted with 2-methyltetrahydrofuran (20 mL) at 50° C. The organic layers were combined and concentrated under reduced pressure to afford crude product (9.0 g) which contained residual morpholine. The crude product was heated in hot toluene (30 mL). Some undissolved solids remained and the hot solution was decanted into a clean receiver. The toluene solution was cooled, resulting in crystallization of solids. The solution was further cooled in a refrigerator at 2-8° C. for one hour. The solids were filtered, washed with toluene (10 mL), and dried to afford the title compound as a tan solid (2.85 g).

To a vessel charged with (S)-1-(1-methyl-6-morpholino-1H-pyrrolo[3,2-b]pyridin-5-yl)ethan-1-amine (1.00 g, 3.84 mmol) was added and isopropanol (5 mL). The resulting slurry was heated to 80° C., which dissolved most of the solids. A solution of (S)-mandelic acid (584 mg, 3.84 mmol) in IPA (3 mL) was prepared with heating and then transferred to the vessel containing the amine. The resulting yellow solution was slowly cooled to RT. At 60° C. a small amount of pure (S)-mandelic acid salt of (S)-1-(1-methyl-6-morpholino-1H-pyrrolo[3,2-b]pyridin-5-yl)ethan-1-amine was added and crystallization occurred. The slurry was stirred at RT for one hour. The solids were filtered, washed with IPA (2×2 mL), and dried to give an isopropanol solvate of an (S)-mandelic acid salt of (S)-1-(1-methyl-6-morpholino-1H-pyrrolo[3,2-b]pyridin-5-yl)ethan-1-amine as a crystalline white solid (1.60 g; IPA solvate determination by $^1$H NMR).

Preparation x22: (S)-1-(1-Methyl-6-(1H-pyrazol-5-yl)-1H-pyrrolo[3,2-b]pyridin-5-yl)ethanamine

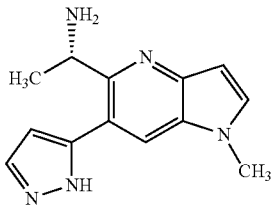 [SMILES: C[C@H](N)c1nc2ccn(C)c2cc1-c1ccn[nH]1]

A solution of (S)-tert-butyl (1-(6-bromo-1-methyl-1H-pyrrolo[3,2-b]pyridin-5-yl)ethyl)carbamate (2 g, 5.65 mmol), tert-butyl 5-(4,4,5,5-tetramethyl-1,3,2-dioxaborolan-2-yl)-1H-pyrazole-1-carboxylate (4.98 g, 16.9 mmol) and 1,1'-bis(diphenylphosphino)ferrocene-palladium(II)dichloride dichloromethane complex in dioxane (5 mL) was placed in a septum-sealed vial. A nitrogen-saturated, aqueous 2M cesium carbonate solution (5 mL) was added. The mixture was heated at 80° C. overnight. The solvent was evaporated in vacuo and the residue was dissolved in MeOH/DCM, absorbed on silica gel, and purified by column chromatography eluting with 20-80% EtOAc in hexane over a 60 minute period. The purified product was dissolved in dioxane (5 mL). A 4M solution of HCl in dioxane was added and the mixture was stirred at RT for 2 hours. Most of the solvent was removed in vacuo. The residue was diluted in ether, and the resulting precipitate was collected on a filter and was washed with ether to give an HCl salt of the title compound, which was used without further purification. ESI-MS m/z [M+H]$^+$ calc'd for $C_{13}H_{15}N_5$, 242. found 242.

Preparation x23: tert-Butyl ((1S)-1-(6-(3,5-dimethyl-1H-pyrazol-4-yl)-1-methyl-1H-pyrrolo[3,2-b]pyridin-5-yl)ethyl)carbamate

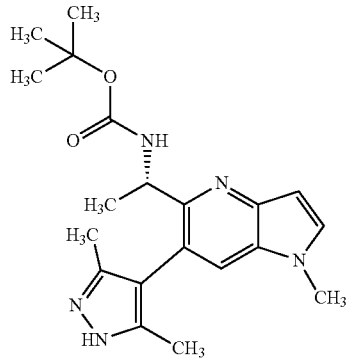 [SMILES: Cc1n[nH]c(C)c1-c1cc2c(ccn2C)nc1[C@H](C)NC(=O)OC(C)(C)C]

A solution of (S)-tert-butyl (1-(6-bromo-1-methyl-1H-pyrrolo[3,2-b]pyridin-5-yl)ethyl)carbamate (2 g, 5.65 mmol), 3,5-dimethyl-4-(4,4,5,5-tetramethyl-1,3,2-dioxaborolan-2-yl)-1H-pyrazole (1160 mg, 5.20 mmol) and PdCl$_2$(dppf)-CH$_2$Cl$_2$ adduct (147 mg, 0.180 mmol) in dioxane (3500 μL) and aqueous 3M potassium carbonate solution (5400 μL, 16 mmol) was heated at 120° C. for 5 hours in a microwave reactor. The mixture was diluted with ethyl acetate (177 mL), washed with saturated ammonium chloride (177 mL) and brine, dried over Na$_2$SO$_4$, and concentrated in vacuo. The crude product was purified on silica gel, eluting with EtOAc to give the title compound. ESI-MS m/z [M+H]$^+$ calc'd for $C_{20}H_{27}N_5O_2$, 370.2. found 370.6.

Preparation x24: (1S)-1-(6-(3,5-Dimethyl-1H-pyrazol-4-yl)-1-methyl-1H-pyrrolo[3,2-b]pyridin-5-yl)ethanamine

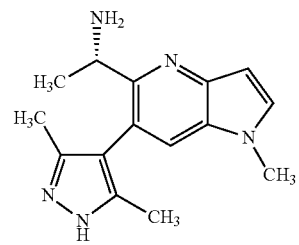 [SMILES: Cc1n[nH]c(C)c1-c1cc2c(ccn2C)nc1[C@H](C)N]

To a stirred solution of tert-butyl ((1S)-1-(6-(3,5-dimethyl-1H-pyrazol-4-yl)-1-methyl-1H-pyrrolo[3,2-b]pyridin-5-yl)ethyl)carbamate (149 mg, 0.403 mmol) in THF (4 mL) was added dropwise 4 M HCl (1 mL, 4.00 mmol) in dioxane. The mixture was stirred at RT for 2 hours and then concentrated in vacuo to give an HCl salt of the title compound as an off-white solid. ESI-MS m/z [M+H]$^+$ calc'd for $C_{15}H_{19}N_5$, 270.16; found 270.6.

Preparation x25: (S)-1-(6-(2-(Benzyloxy)pyridin-4-yl)-1-methyl-1H-pyrrolo[3,2-b]pyridin-5-yl)ethanamine

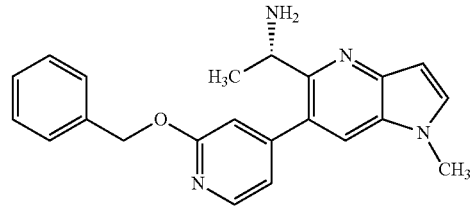 [SMILES: C[C@H](N)c1nc2ccn(C)c2cc1-c1ccnc(OCc2ccccc2)c1]

A solution of (S)-tert-butyl (1-(6-bromo-1-methyl-1H-pyrrolo[3,2-b]pyridin-5-yl)ethyl)carbamate (1 g, 2.82 mmol), tetrakis(triphenylphosphine)palladium(0) (0.163 g, 0.141 mmol) and (2-(benzyloxy)pyridin-4-yl)boronic acid (1.29 g, 5.65 mmol) in dioxane and saturated NaHCO$_3$ (1:1, 10 mL) was heated to 130° C. in a microwave reactor for 40 minutes. The solvent was removed and the residue was purified by flash column chromatography (SiO$_2$) eluting with 10-50% EtOAc in hexane. The desired fractions were pooled and concentrated. The residue was dissolved in THF, and 4M HCl in dioxane was added. The mixture was stirred at RT for 2 hours. Most of solvent was removed in vacuo. The residue was diluted in ether, and the solid precipitate was collected on a filter and washed with ether to give an HCl salt of the title compound (1.1 g, 99%). ESI-MS m/z [M+H]+ calc'd for $C_{22}H_{22}N_4O$, 359; found 359.

Preparation x26: (S)-1-(1-Methyl-6-(thiazol-4-yl)-1H-pyrrolo[3,2-b]pyridin-5-yl)ethanamine

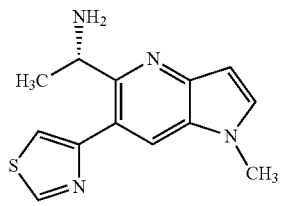 [SMILES: C[C@H](N)c1nc2ccn(C)c2cc1-c1cscn1]

A solution of (S)-tert-butyl (1-(6-bromo-1-methyl-1H-pyrrolo[3,2-b]pyridin-5-yl)ethyl)carbamate (1 g, 2.82 mmol), 4-(tributylstannyl)thiazole (1.06 g, 2.82 mmol) and tetrakis(triphenylphosphine)palladium(0) (0.033 g, 0.028 mmol) in toluene (10 mL) was heated to 110° C. in a microwave reactor for 1 hour. The solvent was removed and the residue was purified by flash column chromatography eluting with 30-50% EtOAc in hexane. The fractions containing the desired compound were combined, the solvents removed, and the residue dissolved in THF. To the solution was added 4M HCl in dioxane and the mixture was stirred at RT for 2 hours. About 90% of the solvent was removed in vacuo and the residue was diluted in ether. The precipitate was collected and washed with ether to give a di-HCl salt of the title compound. ESI-MS m/z [M+H]+ calc'd for $C_{13}H_{14}N_4S$, 259; found 259.

Preparation x27: (S)-4-Amino-6-((1-(1-methyl-6-(thiazol-4-yl)-1H-pyrrolo[3,2-b]pyridin-5-yl)ethyl)amino)-2-(methylthio)pyrimidine-5-carbonitrile

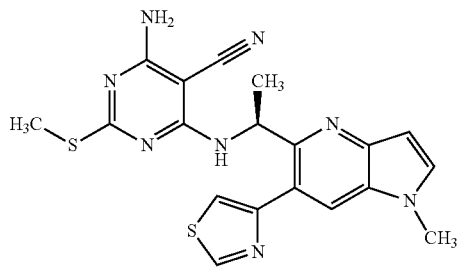 [SMILES: CSc1nc(N)c(C#N)c(N[C@@H](C)c2nc3ccn(C)c3cc2-c2cscn2)n1]

(S)-1-(1-methyl-6-(thiazol-4-yl)-1H-pyrrolo[3,2-b]pyridin-5-yl)ethanamine dihydrochloride (200 mg, 0.604 mmol), 4-amino-6-chloro-2-(methylthio)pyrimidine-5-carbonitrile (182 mg, 0.906 mmol), and N-ethyl-N-isopropylpropan-2-amine (0.315 mL, 1.81 mmol) were combined in acetonitrile (6 mL). The reaction mixture was heated in a microwave reactor at 120° C. for 2 hours and then concentrated. The residue was dissolved in MeOH/DCM, absorbed onto silica gel, and purified by column chromatography eluting with 20-80% EtOAc in hexane over 60 minutes. The fractions containing the desired product were collected and concentrated to give the title compound (22 mg, 9%). ESI-MS m/z [M+H]+ calc'd for $C_{19}H_{18}N_8S_2$, 423; found 423.

Preparation x28: (S)-4-amino-6-((1-(1-methyl-6-(thiazol-4-yl)-1H-pyrrolo[3,2-b]pyridin-5-yl)ethyl)amino)-2-(methylsulfonyl)pyrimidine-5-carbonitrile

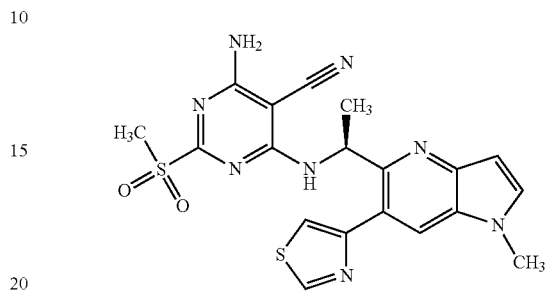

To a round-bottomed flask was added a mixture of (S)-4-amino-6-((1-(1-methyl-6-(thiazol-4-yl)-1H-pyrrolo[3,2-b]pyridin-5-yl)amino)-2-(methylthio)pyrimidine-5-carbonitrile (22 mg, 0.052 mmol) in acetonitrile (7 mL) and water (7 mL). The reaction mixture was cooled to 0° C. and Oxone (80 mg, 0.130 mmol) was added. The reaction mixture was stirred at 0° C. for 30 minutes and was then allowed to warm to RT. After 1.5 hours the reaction mixture was diluted with EtOAc and washed with $H_2O$ (3×). The combined organic layers were dried over $Na_2SO_4$, filtered, and concentrated to give the title compound as a yellow solid, which was used without further purification. ESI-MS m/z [M+H]+ calc'd for $C_{19}H_{18}N_8O_2S_2$, 455; found 455.

Preparation x29: (S)-1-(1-Methyl-6-(3-methyl-1H-pyrazol-4-yl)-1H-pyrrolo[3,2-b]pyridin-5-yl)ethanamine

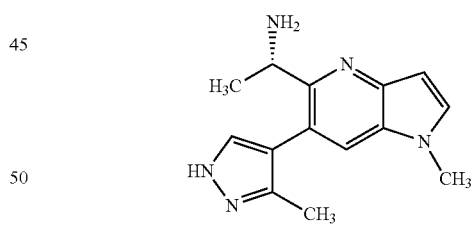

A solution of (S)-tert-butyl (1-(6-bromo-1-methyl-1H-pyrrolo[3,2-b]pyridin-5-yl)ethyl)carbamate (1.15 g, 3.25 mmol), tetrakis(triphenylphosphine)palladium (0) (0.188 g, 0.162 mmol) and 3-methyl-4-(4,4,5,5-tetramethyl-1,3,2-dioxaborolan-2-yl)-1H-pyrazole (2.026 g, 9.74 mmol) in dioxane/saturated aqueous $NaHCO_3$ (1:1, 20 mL) was heated to 150° C. in a microwave reactor for 12 hours. After cooling to RT, the solvent was removed, and the reaction mixture was purified by silica gel column chromatography eluting with 20-100% EtOAc in hexane over 1.5 hours. The intermediate was taken up in dioxane and 4 M HCl (1:1). The mixture was stirred at RT for 1 hour. The volatiles were removed to give the title compound as an HCl salt of the title compound, which was used without further purification (58%). ESI-MS m/z [M+H]$^+$ calc'd for $C_{14}H_{17}N_5$, 256; found 256.

Preparation x30: (S)-4-Methyl-6-((1-(1-methyl-6-(3-methyl-1H-pyrazol-4-yl)-1H-pyrrolo[3,2-b]pyridin-5-yl)ethyl)amino)-2-(methylthio)pyrimidine-5-carbonitrile

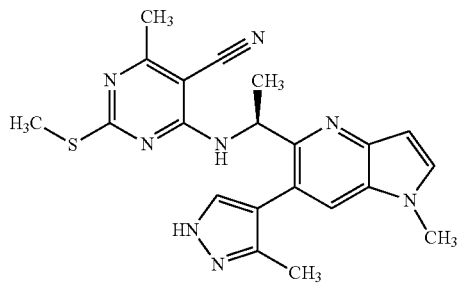 [SMILES: CSc1nc(C)c(C#N)c(N[C@@H](C)c2nc3ccn(C)c3cc2-c2c[nH]nc2C)n1]

A solution of (S)-1-(1-methyl-6-(3-methyl-1H-pyrazol-4-yl)-1H-pyrrolo[3,2-b]pyridin-5-yl)ethanamine dihydrochloride (200 mg, 0.609 mmol), 4-chloro-6-methyl-2-(methylthio)pyrimidine-5-carbonitrile (182 mg, 0.914 mmol), and N-ethyl-N-isopropylpropan-2-amine (0.318 mL, 1.83 mmol) in acetonitrile (5 mL) was heated in a microwave reactor at 120° C. for 2 hours. The mixture was then concentrated. The residue was dissolved in MeOH/DCM, absorbed onto silica gel, and purified by column chromatography eluting with 20-80% EtOAc in hexane over 60 minutes to give the title compound. ESI-MS m/z [M+H]$^+$ calc'd for $C_{21}H_{22}N_8S$, 419; found 419.

Preparation x31: (S)-4-Methyl-6-((1-(1-methyl-6-(3-methyl-1H-pyrazol-4-yl)-1H-pyrrolo[3,2-b]pyridin-5-yl)ethyl)amino)-2-(methylsulfonyl)pyrimidine-5-carbonitrile

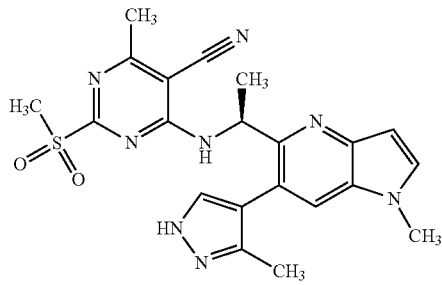 [SMILES: Cc1n[nH]cc1-c1cc2c(ccn2C)nc1[C@H](C)Nc1nc(S(C)(=O)=O)nc(C)c1C#N]

To a round-bottomed flask was added a mixture of (S)-4-methyl-6-((1-(1-methyl-6-(3-methyl-1H-pyrazol-4-yl)-1H-pyrrolo[3,2-b]pyridin-5-yl)ethyl)amino)-2-(methylthio)pyrimidine-5-carbonitrile (100 mg, 0.239 mmol) in acetonitrile (7 mL) and water (7 mL). The reaction mixture was cooled to 0° C. Oxone (367 mg, 0.597 mmol) was added and the reaction mixture was stirred at 0° C. for 30 minutes and then allowed to warm to RT. After 1.5 hours the reaction mixture was diluted with EtOAc and washed with H$_2$O (3×). The combined organic layers were dried over Na$_2$SO$_4$, filtered, and concentrated to give the title compound as a yellow solid, which was used without further purification. ESI-MS m/z [M+H]$^+$ calc'd for $C_{21}H_{22}N_8O_2S$, 451; found 451.

Preparation x32: (S)-1-(6-(1-(Difluoromethyl)-1H-pyrazol-5-yl)-1-methyl-1H-pyrrolo[3,2-b]pyridin-5-yl)ethanamine

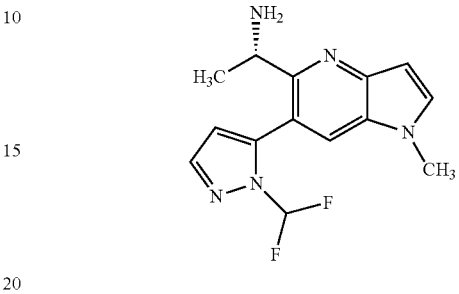

A solution of (S)-tert-butyl (1-(6-bromo-1-methyl-1H-pyrrolo[3,2-b]pyridin-5-yl)ethyl)carbamate (1.0 g, 2.8 mmol), tetrakis(triphenylphosphine)palladium(0) (0.163 g, 0.141 mmol) and (1-(difluoromethyl)-1H-pyrazol-5-yl)boronic acid (0.914 g, 5.65 mmol) in dioxane/sat. NaHCO$_3$ (1:1, 10 mL) was heated to 120° C. in a microwave reactor. The mixture was subsequently concentrated in vacuo and the residue was purified by silica gel column chromatography eluting with 20-80% EtOAc in hexane over 2 hours. The fractions containing the desired compound were combined and concentrated. The residue was dissolved in THF, and 4M HCl in dioxane was added. The mixture was stirred at RT for 2 hours. Approximate 90% of solvent was removed in vacuo, and the residue was diluted in ether. A precipitate formed. The solid was collected on a filter and washed with ether to give a di-HCl salt of the title compound (915 mg, 89%). ESI-MS m/z [M+H]$^+$ calc'd for $C_{14}H_{15}F_2N_5$, 292; found 292.

Preparation x33: (S)-1-(6-(1-Cyclopropyl-1H-pyrazol-5-yl)-1-methyl-1H-pyrrolo[3,2-b]pyridin-5-yl)ethanamine

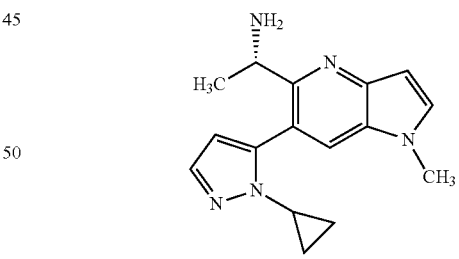

A solution of (S)-tert-butyl (1-(6-bromo-1-methyl-1H-pyrrolo[3,2-b]pyridin-5-yl)ethyl)carbamate (1.0 g, 2.8 mmol), tetrakis(triphenylphosphine)palladium(0) (0.163 g, 0.141 mmol) and (1-cyclopropyl-1H-pyrazol-5-yl)boronic acid (0.858 g, 5.65 mmol) in dioxane/sat. NaHCO$_3$ (1:1, 20 mL) was heated to 120° C. in a microwave reactor for 1 hour. The mixture was concentrated in vacuo, and the residue was purified by silica gel column chromatography eluting with 20-80% EtOAc in hexane over 2 hours. The fractions containing the desired compound were combined and concentrated. The residue was dissolved in THF, and 4M HCl in dioxane was added. The mixture was stirred at RT for 2 hours.

Approximate 90% of solvent was removed in vacuo, and the residue was diluted in ether. A precipitate formed. The solid was collected on a filter and washed with ether to give a di-HCl salt of the title compound (915 mg, 91%). ESI-MS m/z [M+H]$^+$ calc'd for $C_{16}H_{19}N_5$, 282; found 282.

Preparation x34: (S)-1-(6-(3-Methoxyazetidin-1-yl)-1-methyl-1H-pyrrolo[3,2-b]pyridin-5-yl)ethanamine

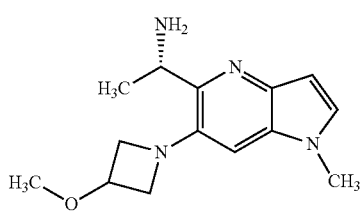 [SMILES: COC1CN(c2cc3c(ccn3C)nc2[C@H](C)N)C1]

To a microwave vial containing 3-methoxyazetidine hydrochloride (500 mg, 4.05 mmol) were added KOt-Bu (1339 mg, 11.93 mmol) and DME (8 mL) under an atmosphere of nitrogen. The mixture was heated to 90° C. in a sand bath. A solution of (S)-1-(6-bromo-1-methyl-1H-pyrrolo[3,2-b]pyridin-5-yl)ethanamine (461 mg, 1.82 mmol) in DME (8 mL) was added dropwise to the hot suspension. The mixture was stirred at 90° C. overnight. Additional KOt-Bu (1956 mg, 17.43 mmol) was added and the mixture was heated to 90° C. for 90 minutes. The reaction mixture was subsequently concentrated in vacuo. The residue was dispersed in DMSO/MeOH (1:1, 10 mL), filtered, and purified by preparative HPLC eluting with 15-40% ACN in water (with 0.035% NH$_4$HCO$_3$). The fractions containing the desired product were combined and concentrated in vacuo to give the title compound as an off-white solid (469 mg, 99%). ESI-MS m/z [M+H]+ calc'd for $C_{14}H_{20}N_4O$, 261; found 261.

Preparation x35: 6-(4-Hydroxy-4-methylpiperidin-1-yl)-1-methyl-1H-pyrrolo[3,2-b]pyridine-5-carbonitrile

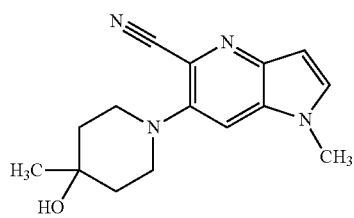 [SMILES: Cn1ccc2nc(C#N)c(N3CCC(C)(O)CC3)cc21]

In a flask were combined 6-bromo-1-methyl-1H-pyrrolo[3,2-b]pyridine-5-carbonitrile (500 mg, 2.118 mmol), 4-methylpiperidin-4-ol (244 mg, 2.118 mmol), Xantphos (123 mg, 0.212 mmol), Pd(OAc)$_2$ (47.6 mg, 0.212 mmol) and cesium carbonate (1380 mg, 4.24 mmol) in dioxane (10 mL) to give an orange suspension. The flask was degassed with N$_2$, sealed, and heated to 90° C. for 3 hours. The reaction mixture was diluted with EtOAc and washed with saturated aqueous NH$_4$Cl (3×10 mL). The combined organic layers were dried over MgSO$_4$, filtered, and concentrated in vacuo. The crude product was loaded onto a silica gel cartridge (ISCO®, 12 g) and eluted with an EtOAc/hexane gradient. The product was collected and concentrated in vacuo to give the title compound as a yellow solid (245 mg, 43%). ESI-MS m/z [M+H]$^+$ calc'd for $C_{15}H_{18}N_4O$, 271; found 271.

Preparation x36: 1-(5-(1-Aminoethyl)-1-methyl-1H-pyrrolo[3,2-b]pyridin-6-yl)-4-methylpiperidin-4-ol

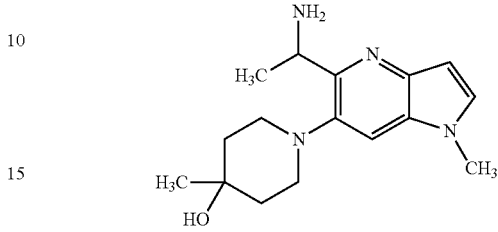

To a solution of 6-(4-hydroxy-4-methylpiperidin-1-yl)-1-methyl-1H-pyrrolo[3,2-b]pyridine-5-carbonitrile (245 mg, 0.906 mmol) in THF (5 mL) at 0° C. was slowly added 3M methylmagnesium bromide in ether (1.21 mL, 3.63 mmol). The resulting yellow solution was stirred at 0° C. for 2.5 hours. The reaction was quenched with MeOH (5 mL) and stirred for 15 minutes at RT. Sodium borohydride (68.6 mg, 1.81 mmol) was added. The reaction was stirred for 1 hour, quenched with 1M HCl (5 mL), and then stirred for an additional 15 minutes. The mixture was subsequently diluted with EtOAc and washed with saturated aqueous NaHCO$_3$ (3×). The combined organic layers were dried over MgSO$_4$, filtered, and concentrated in vacuo to give the title compound, which was used without further purification. ESI-MS m/z [M+H]$^+$ calc'd for $C_{16}H_{24}N_4$, 289; found 289.

Preparation x37: (S)-tert-Butyl (1-(6-(3,6-dihydro-2H-pyran-4-yl)-1-methyl-1H-pyrrolo[3,2-b]pyridin-5-yl)ethyl)carbamate

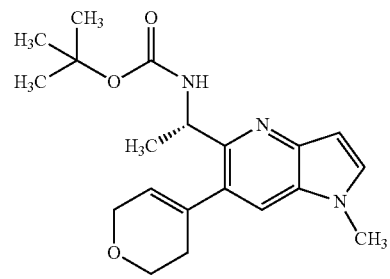 [SMILES: C[C@H](NC(=O)OC(C)(C)C)c1nc2ccn(C)c2cc1C1=CCOCC1]

To a 20 mL microwave vial were added (S)-tert-butyl (1-(6-bromo-1-methyl-1H-pyrrolo[3,2-b]pyridin-5-yl)ethyl)carbamate (1 g, 2.8 mmol), 2-(3,6-dihydro-2H-pyran-4-yl)-4,4,5,5-tetramethyl-1,3,2-dioxaborolane (0.890 g, 4.23 mmol), PdCl$_2$(dppf) (0.207 g, 0.282 mmol) and cesium carbonate (1.84 g, 5.65 mmol) in dioxane (12 mL) and water (2 mL). The resulting brown suspension was heated in a microwave reactor at 90° C. on high absorbance for 1 hour. The reaction mixture was diluted with EtOAc and washed with saturated aqueous NH$_4$Cl (3×). The combined organic layers were dried over MgSO$_4$, filtered, and concentrated. The product was purified using silica gel column chromatography (12 g, 2:8 to 8:2 EtOAc/hexane) to give the title compound as a yellow oil. $^1$H NMR (400 MHz, DMSO-d$_6$) δ ppm 0.99-1.13 (m, 9 H), 1.25-1.38 (m, 12 H), 3.74-3.97 (m, 7 H), 4.16-4.26

(m, 2H), 4.90-5.05 (m, 1 H), 5.68-5.77 (m, 1 H), 6.47-6.55 (m, 1 H), 6.76-6.87 (m, 1 H), 7.59 (s, 2 H); ESI-MS m/z [M+H]+ calc'd for $C_{20}H_{27}N_3O_3$, 358; found 358.

Preparation x38: (S)-tert-Butyl (1-(1-methyl-6-(tetrahydro-2H-pyran-4-yl)-1H-pyrrolo[3,2-b]pyridin-5-yl)ethyl)carbamate

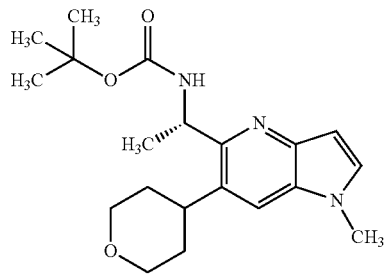 [SMILES: C[C@H](NC(=O)OC(C)(C)C)c1nc2ccn(C)c2cc1C1CCOCC1]

To a 100 mL round-bottom flask fitted with a 3-way valve and a hydrogen-filled balloon, were added (S)-tert-butyl (1-(6-(3,6-dihydro-2H-pyran-4-yl)-1-methyl-1H-pyrrolo[3,2-b]pyridin-5-yl)ethyl)carbamate (1.23 g, 3.44 mmol) in MeOH (20 mL) along with palladium hydroxide on carbon (0.097 g, 0.688 mmol). The flask was evacuated and hydrogen introduced via the three-way valve. The reaction mixture was stirred overnight at RT. The next day an additional equivalence of Pd(OH)$_2$ was added and the reaction mixture was stirred overnight. The reaction mixture was subsequently diluted with EtOAc, filtered through a pad of Celite, and concentrated to give the title compound as a yellow oil, which was used without further purification.

Preparation x39: (S)-1-(1-Methyl-6-(tetrahydro-2H-pyran-4-yl)-1H-pyrrolo[3,2-b]pyridin-5-yl)ethanamine

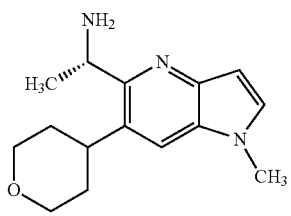 [SMILES: C[C@H](N)c1nc2ccn(C)c2cc1C1CCOCC1]

To a solution of (S)-tert-butyl (1-(1-methyl-6-(tetrahydro-2H-pyran-4-yl)-1H-pyrrolo[3,2-b]pyridin-5-yl)ethyl)carbamate (515 mg, 1.361 mmol) in dioxane (5 mL) was added 4.0 M HCl in 1,4-dioxane (3.40 mL, 13.6 mmol) at 23° C. The mixture was stirred for 30 minutes at 23° C. Additional 4.0 M HCl (3.40 mL, 13.6 mmol) was added at 23° C. and the mixture was stirred for 1.5 hours. The reaction mixture was concentrated via rotary evaporation, re-suspended in Et$_2$O (5 mL), filtered, and rinsed with Et$_2$O. The resulting solid was dried in vacuo to give an HCl salt of the title compound as a yellow solid (403 mg, 100%). ESI-MS m/z [M+H]+ calc'd for $C_{15}H_{21}N_3O$, 260; found 260.

Preparation x40: tert-Butyl ((1S)-1-(6-(3,5-dimethylisoxazol-4-yl)-1-methyl-1H-pyrrolo[3,2-b]pyridin-5-yl)ethyl)carbamate

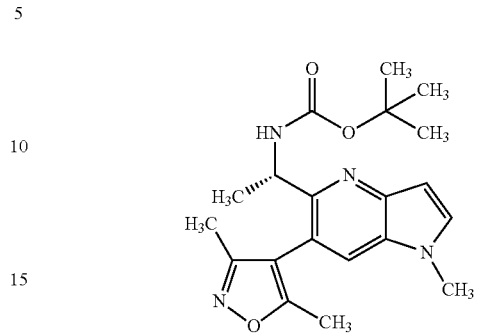

A solution of (S)-tert-butyl (1-(6-bromo-1-methyl-1H-pyrrolo[3,2-b]pyridin-5-yl)ethyl)carbamate (100 mg, 0.282 mmol), 3,5-dimethyl-4-(4,4,5,5-tetramethyl-1,3,2-dioxaborolan-2-yl)isoxazole (126 mg, 0.565 mmol) and PdCl$_2$(dppf)-CH$_2$Cl$_2$ adduct (11 mg, 0.014 mmol) in dioxane (1.0 mL) and 3 M aqueous potassium carbonate (1.01 mL, 3.02 mmol) were heated at 120° C. for 1 hour in a microwave reactor. The mixture was diluted with EtOAc (50 mL), washed with saturated aqueous ammonium chloride (50 mL) and brine, dried over MgSO$_4$, and concentrated in vacuo. The crude product was purified on a silica gel column (24 g) eluting with a 0-50% EtOAc gradient in hexanes to give the title compound as a clear, colorless oil (107 mg, 100%). $^1$H NMR (400 MHz, DMSO-d$_6$) δ ppm 1.27-1.35 (m, 9 H), 2.05 (d, J=12.6 Hz, 3 H), 2.20-2.28 (m, 3 H), 3.77-3.85 (m, 3 H), 4.52-4.68 (m, 1H), 6.59 (d, J=3.0 Hz, 1 H), 6.81-6.90 (m, 1 H), 7.68 (d, J=3.3 Hz, 1 H), 7.71 (d, J=8.8 Hz, 1 H); ESI-MS m/z [M+H]+ calc'd for $C_{20}H_{26}N_4O_3$, 371; found 371.

Preparation x41: (1S)-1-(6-(3,5-Dimethylisoxazol-4-yl)-1-methyl-1H-pyrrolo[3,2-b]pyridin-5-yl)ethanamine

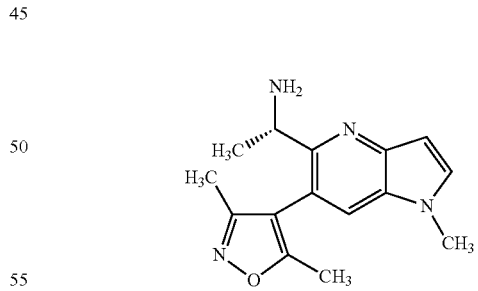

To a solution of tert-butyl ((1S)-1-(6-(3,5-dimethylisoxazol-4-yl)-1-methyl-1H-pyrrolo[3,2-b]pyridin-5-yl)ethyl)carbamate (105 mg, 0.283 mmol) in anhydrous DCM (3.0 mL) was added 4 N HCl in dioxane (0.40 mL, 1.6 mmol). The solution was stirred at 20° C. for 21 hours and then concentrated in vacuo to give an HCl salt of the title compound as a white solid, which was used without further purification. ESI-MS m/z [M+H]+ calc'd for $C_{15}H_{18}N_4O$, 271; found 271.

Preparation x42: 6-(3,3-Difluoroazetidin-1-yl)-1-methyl-1H-pyrrolo[3,2-b]pyridine-5-carbonitrile

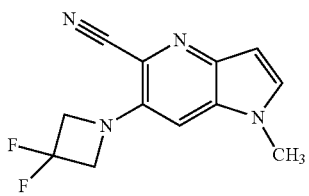 [SMILES: Cn1ccc2nc(C#N)c(N3CC(F)(F)C3)cc21]

To a 5 mL vial were added 6-bromo-1-methyl-1H-pyrrolo[3,2-b]pyridine-5-carbonitrile (500 mg, 2.12 mmol), Xantphos (123 mg, 0.212 mmol), palladium (II) acetate (47.6 mg, 0.212 mmol), cesium carbonate (1380 mg, 4.24 mmol) and 3,3-difluoroazetidine hydrochloride (549 mg, 4.24 mmol) in dioxane (5.0 mL). The resulting yellow suspension was heated to 110° C. for 22 hours. LC/MS showed about 50% conversion. More palladium (II) acetate (50 mg) was added and heating was continued at 110° C. for 2 days. The solution was diluted with EtOAc (up to 100 mL) and then washed with saturated aqueous ammonium chloride (100 mL) and filtered to remove solids. The layers were separated, and the organic layer was washed with brine, dried over MgSO$_4$, and concentrated in vacuo. The crude product was purified on a silica gel column (80 g) eluting with a 0-60% ethyl acetate in hexanes to give the title compound as a yellow solid (152 mg, 29%). $^1$H NMR (400 MHz, DMSO-d$_6$) δ ppm 3.79 (s, 3 H), 4.55 (t, J=12.4 Hz, 4 H), 6.55 (dd, J=3.3, 0.8 Hz, 1 H), 7.38 (d, J=0.8 Hz, 1 H), 7.69 (d, J=3.5 Hz, 1 H); ESI-MS m/z [M+H]$^+$ calc'd for C$_{12}$H$_{10}$F$_2$N$_4$, 249; found 249.

Preparation x43: 1-(6-(3,3-Difluoroazetidin-1-yl)-1-methyl-1H-pyrrolo[3,2-b]pyridin-5-yl)ethanamine

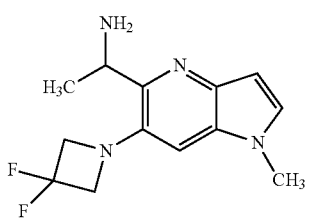 [SMILES: CC(N)c1nc2ccn(C)c2cc1N1CC(F)(F)C1]

To a slurry of 6-(3,3-difluoroazetidin-1-yl)-1-methyl-1H-pyrrolo[3,2-b]pyridine-5-carbonitrile (130 mg, 0.524 mmol) in toluene (3.0 mL) at −30° C. was added dropwise methylmagnesium chloride (0.262 mL, 0.786 mmol). The mixture was moved to an ice bath at 0° C. and stirred for 2 hours. The reaction mixture had lots of solid and was about 50% complete by LC/MS. THF (1 mL) was added at 0° C. followed by more methylmagnesium chloride (0.262 mL, 0.786 mmol) and the solution was allowed to sit in a refrigerator at −10° C. for 16 hours. The solution was subsequently warmed to 0° C. and the reaction was quenched with anhydrous methanol (1 mL). A solid formed which dissolved upon stirring. The mixture was added to a solution of sodium borohydride (99 mg, 2.62 mmol) in methanol (5 mL) at 0° C. The resulting mixture was stirred for 30 minutes at 0° C. Excess sodium borohydride was consumed by adding acetic acid (0.300 mL, 5.24 mmol). The solution was allowed to warm to 20° C. and was concentrated in vacuo. The concentrate was taken up in EtOAc (50 mL), washed with saturated aqueous sodium bicarbonate, dried over MgSO$_4$, and concentrated in vacuo to give the title compound, which was used without further purification (84 mg, 60%). ESI-MS m/z [M+H]$^+$ calc'd for C$_{13}$H$_{16}$F$_2$N$_4$, 267; found 267.

Preparation x44: 6-(3-Hydroxyazetidin-1-yl)-1-methyl-1H-pyrrolo[3,2-b]pyridine-5-carbonitrile

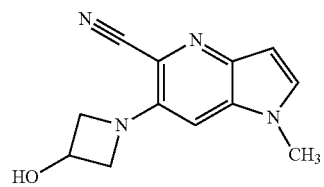 [SMILES: Cn1ccc2nc(C#N)c(N3CC(O)C3)cc21]

6-Bromo-1-methyl-1H-pyrrolo[3,2-b]pyridine-5-carbonitrile (4.27 g, 18.1 mmol), azetidin-3-ol (2.36 g, 18.1 mmol), Xantphos (1.05 g, 1.81 mmol), Pd(OAc)$_2$ (0.406 g, 1.81 mmol) and cesium carbonate (11.8 g, 36.2 mmol) in dioxane (100 mL) were combined in a flask to give an orange suspension. The flask was purged with N$_2$, sealed, and heated to 90° C. for 3 hours. The crude material was diluted with EtOAc (25 mL) and filtered through a pad of Celite. The filtrate was washed with saturated aqueous NH$_4$Cl (3×). The combined organic layers were dried over MgSO$_4$, filtered, and concentrated. The crude product was loaded onto a silica gel cartridge (ISCO®, 120 g) and eluted using an EtOAc/hexane gradient. The product was collected and concentrated in vacuo to afford the title compound as a yellow solid (2.8 g, 67%). ESI-MS m/z [M+H]$^+$ calc'd for C$_{12}$H$_{12}$N$_4$O, 229; found 229.

Preparation x45: 1-(5-(1-Aminoethyl)-1-methyl-1H-pyrrolo[3,2-b]pyridin-6-yl)azetidin-3-ol

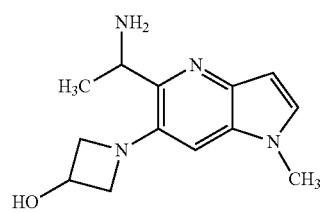 [SMILES: CC(N)c1nc2ccn(C)c2cc1N1CC(O)C1]

To a solution of 6-(3-hydroxyazetidin-1-yl)-1-methyl-1H-pyrrolo[3,2-b]pyridine-5-carbonitrile (2.6 g, 11 mmol) in THF 100 mL at 0° C. was slowly added 3M methylmagnesium bromide in ether (15.2 mL, 45.6 mmol) to give a yellow solution. After 1 hour, the reaction mixture was warmed to RT and was stirred for an additional 2.5 hours. The reaction was then quenched with MeOH (5 mL). The mixture was stirred for 15 minutes. Sodium borohydride (0.862, 22.8 mmol) was added and the reaction mixture was stirred for 1 hour. The reaction was subsequently quenched with 1M HCl (5 mL). The mixture was stirred for 15 minutes, diluted with EtOAc, and washed with saturated aqueous NH$_4$Cl (3×). The aqueous layer was concentrated to give the title compound as a brown solid, which was used without further purification.

Preparation x46: 1-Methyl-6-(2-oxa-6-azaspiro[3,3]heptan-6-yl)-1H-pyrrolo[3,2-b]pyridine-5-carbonitrile

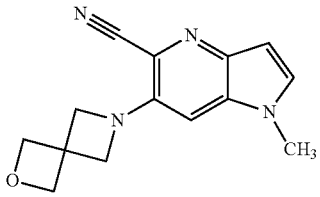 [SMILES: Cn1ccc2nc(C#N)c(N3CC4(COC4)C3)cc21]

6-Bromo-1-methyl-1H-pyrrolo[3,2-b]pyridine 5-carbonitrile (300 mg, 1.27 mmol), sodium tert-butoxide (366 mg, 3.81 mmol), racemic BINAP (79 mg, 0.127 mmol), $Pd_2 dba_3$ (58 mg, 0.064 mmol), and 2-oxo-6-azaspiro[3,3]heptane, 0.5 oxylic acid salt (274 mg, 1.91 mmol) were combined in DMA (12 mL) under $N_2$. The reaction mixture was heated at 102° C. in a microwave for 1 hour and was then diluted with DCM, washed with brine, dried over $MgSO_4$, and concentrated. Purification by silica gel chromatography (2-5% MeOH in DCM) gave the title compound as a pale yellow solid (222 mg, 69%). $^1$H NMR (500 MHz, $CDCl_3$) δ ppm 7.21 (d, 1H, J=3.5 Hz), 6.60 (s, 1H), 6.58 (d, 1H, J=3.5 Hz), 4.89 (s, 4H), 4.34 (s, 4H), 3.73 (s, 3H). ESI-MS m/z [M+H]$^+$ calc'd for $C_{14}H_{14}F_4O$, 255; found 255.

Preparation x47: 1-(1-Methyl-6-(2-oxa-6-azaspiro[3,3]heptan-6-yl)-1H-pyrrolo[3,2-b]pyridin-5-yl)ethanamine

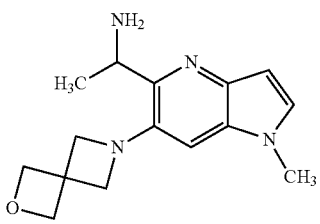 [SMILES: CC(N)c1nc2ccn(C)c2cc1N1CC2(COC2)C1]

Methylmagnesium bromide (1.56 mL, 2.18 mmol) was added slowly to a stirred solution of 1-methyl-6-(2-oxa-6-azaspiro[3.3]heptan-6-yl)-1H-pyrrolo[3,2-b]pyridine-5-carbonitrile (222 mg, 0.873 mmol) in THF (20 mL). The reaction was stirred at 40° C. for 1.5 hours, then cooled to 0° C. and quenched with MeOH (10 mL). After 10 minutes, sodium tetrahydroborate (83 mg, 2.18 mmol) was added. The reaction mixture was stirred for 20 minutes. Water (1 mL) was added and the reaction mixture was stirred for an additional 10 minutes. The reaction mixture was dried over $MgSO_4$, filtered through Celite, and concentrated. The crude product was purified by basic silica column chromatography (3-5% MeOH in DCM) to give the title compound as a clear oil (111 mg, 47%). $^1$H NMR (500 MHz, $CD_3OD$) δ ppm 7.28 (d, 1H, J=3.5 Hz), 7.14 (s, 1H), 6.47 (d, 1H, J=3.5 Hz), 4.89 (s, 4H), 4.33 (q, 1H, J=7.0 Hz), 4.10 ($q_{AB}$, 4H, J=35.5, 7.5 Hz), 3.36 (s, 3H), 1.43 (d, 3H, J=7.0 Hz). ESI-MS m/z [M+H]$^+$ calc'd for $C_{15}H_{20}F_4O$, 273; found 273.

Preparation x48: (R)-1-(6-Bromo-1-methyl-1H-pyrrolo[3,2-b]pyridin-5-yl)ethan-1-amine

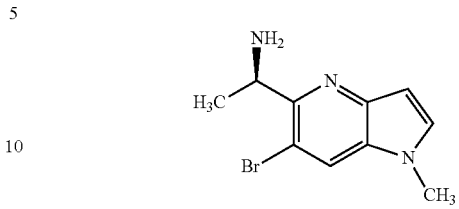

A 100 mL pear flask was charged with 4.0M hydrogen chloride in dioxane (2.117 mL, 8.47 mmol) and cooled in an ice-bath. To the beige solution was added (R)-tert-butyl (1-(6-bromo-1-methyl-1H-pyrrolo[3,2-b]pyridin-5-yl)ethyl) carbamate (3 g, 8.47 mmol) in one portion. The ice-bath was removed and the mixture was stirred at RT for 90 minutes. Ethoxyethane was added (80 mL) and the mixture was cooled in an ice-bath. A resulting white precipitate was collected on a fritted glass funnel to give an HCl salt of the title compound, which was used without further purification.

Preparation x49: (R)-1-(1-Methyl-6-morpholino-1H-pyrrolo[3,2-b]pyridin-5-yl)ethan-1-amine

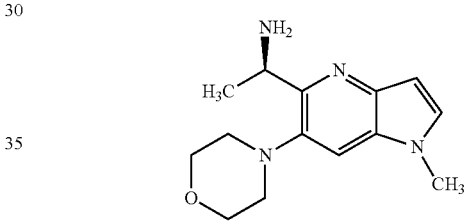

To a suspension of (R)-1-(6-bromo-1-methyl-1H-pyrrolo[3,2-b]pyridin-5-yl)ethanamine, HCl (2.6 g, 8.95 mmol) in 2-MeTHF was added an aqueous saturated sodium bicarbonate solution. The resulting aqueous and organic phases were mixed in a separatory funnel and then separated. The aqueous layer was extracted with 2-MeTHF (2×). The organic layers were combined, dried over $MgSO_4$, filtered, and concentrated to a volume of about 80 mL. The filtrate was further dried by azeotropic distillation with 2-MeTHF. The distillate was isolated in a Dean-Stark trap and removed, while the vessel containing the bromide was replenished with 2-MeTHF (about 50 mL) and redistilled. This process was repeated once more. To the dry filtrate (~5 mL) was added DME (12 mL), morpholine (6 mL, 70 mmol) and potassium 2-methylpropan-2-olate (2.0 g, 18 mmol) at room temperature. The resulting light-orange suspension was heated to 95° C. for about 55 minutes, resulting in a thick brown suspension. UPLC indicated the reaction was complete. Saturated $NaHCO_3$ and EtOAc were added and the layers were separated. The aqueous layer was extracted with EtOAc (1×) and then with 2-MeTHF (2×). The organic layers were combined, dried over $MgSO_4$, filtered, and concentrated to a suspension. Ethoxyethane was added. The resulting crystalline solid was collected on a fritted glass funnel, washed with $Et_2O$, and dried under a stream of nitrogen overnight to give the title compound as a tan solid (605 mg, 26.0%). $^1$H NMR (400 MHz, DMSO-$d_6$) δ ppm 1.28 (d, J=6.32 Hz, 3 H), 1.88 (br s, 2 H), 2.81 (dt, J=11.68, 4.52 Hz, 2 H), 3.02 (dt, J=11.56, 4.58

Hz, 2 H), 3.62-3.91 (m, 6 H), 4.38-4.69 (m, 1 H), 6.45 (dd, J=3.28, 0.76 Hz, 1 H), 7.48 (d, J=3.03 Hz, 1 H), 7.67 (d, J=0.76 Hz, 1 H); ESI-MS m/z [M+H]$^+$ calc'd for C$_{14}$H$_{20}$N$_4$O, 261; found 261.

Preparation x50: (S)-5-(1-((2,6-Diamino-5-cyanopyrimidin-4-yl)amino)ethyl)-1-methyl-6-morpholino-1H-pyrrolo[3,2-b]pyridin-3-yl acetate

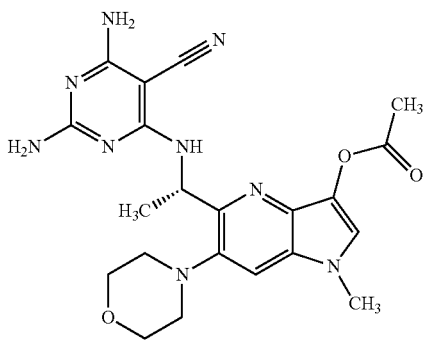 [SMILES: CC(=O)Oc1cn(C)c2cc(N3CCOCC3)c([C@H](C)Nc3nc(N)nc(N)c3C#N)nc12]

Iodobenzene diacetate (0.819 g, 2.54 mmol) was added to a 50 mL pear flask charged with (S)-2,4-diamino-6-((1-(1-methyl-6-morpholino-1H-pyrrolo[3,2-b]pyridin-5-yl)ethyl)amino)pyrimidine-5-carbonitrile (1 g, 2.54 mmol) in acetonitrile. The reaction mixture was stirred for 2 hours during which time the color of the mixture turned darker green. NaOH (7.5 eq) was then added. The mixture was purified by preparative HPLC (acid mode, 5% to 25% ACN/water gradient). The product-containing fractions were pooled, neutralized with NaHCO$_3$, and extracted with EtOAc. The combined organic layers were dried over MgSO$_4$, filtered, and concentrated to give the title compound as a yellow solid (125 mg, 11%). $^1$H NMR (400 MHz, DMSO-d$_6$) δ ppm 1.34 (d, J=6.57 Hz, 3 H) 2.69-2.80 (m, 2 H) 2.96-3.07 (m, 2 H) 3.15 (s, 2 H) 3.60 (br s, 2 H) 3.70-3.89 (m, 4 H) 5.81-5.92 (m, 1 H) 6.03-6.11 (m, 1 H) 6.34-6.42 (m, 2 H) 6.55 (br s, 2 H) 7.32 (s, 1 H); ESI-MS m/z [M+H]$^+$ calc'd for C$_{21}$H$_{25}$N$_9$O$_3$, 452; found 452.

Example 1

(S)-5-Chloro-N$^4$-(1-(1-methyl-6-(1-methyl-1H-pyrazol-5-yl)-1H-pyrrolo[3,2-b]pyridin-5-yl)ethyl)pyrimidine-2,4-diamine

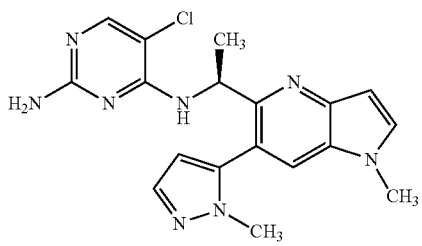 [SMILES: C[C@H](Nc1nc(N)ncc1Cl)c1nc2ccn(C)c2cc1-c1ccnn1C]

A 7 N solution of ammonia (1 mL, 7.00 mmol) in MeOH was added to (S)-2,5-dichloro-N-(1-(1-methyl-6-(1-methyl-1H-pyrazol-5-yl)-1H-pyrrolo[3,2-b]pyridin-5-yl)ethyl)pyrimidin-4-amine (20 mg, 0.050 mmol) while stirring at room temperature. The reaction mixture was stirred at room temperature for 1 hour and then at 100° C. in a microwave reactor for 1 hour. The mixture was concentrated, dissolved in dioxane (1 mL), and treated with ammonium hydroxide (1 mL, 7.19 mmol). The mixture was heated at 100° C. in a microwave reactor for 12 hours. The reaction was concentrated and purified by preparative HPLC (basic mode, 25% to 50% ACN/water gradient) to give the title compound as an off-white solid (13.7 mg, 72.0%). $^1$H NMR (500 MHz, CD$_3$OD) δ ppm 1.42 (d, J=6.35 Hz, 3 H), 3.66 (s, 3 H), 3.90 (s, 3 H), 5.46 (q, J=6.51 Hz, 1 H), 6.45-6.49 (m, 1 H), 6.69-6.72 (m, 1 H), 7.65 (d, J=2.93 Hz, 2 H), 7.69 (s, 1 H), 7.84 (s, 1 H); ESI-MS m/z [M+H]$^+$ calc'd for C$_{18}$H$_{19}$ClN$_8$, 383.14; found 383.3.

Example 2

(S)-2,4-Diamino-6-((1-(1-methyl-6-(1-methyl-1H-pyrazol-5-yl)-1H-pyrrolo[3,2-b]pyridin-5-yl)ethyl)amino)pyrimidine-5-carbonitrile

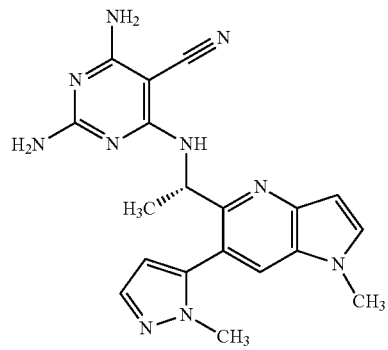 [SMILES: C[C@H](Nc1nc(N)nc(N)c1C#N)c1nc2ccn(C)c2cc1-c1ccnn1C]

(S)-4-Amino-6-((1-(1-methyl-6-(1-methyl-1H-pyrazol-5-yl)-1H-pyrrolo[3,2-b]pyridin-5-yl)ethyl)amino)-2-(methylsulfonyl)pyrimidine-5-carbonitrile (45.2 mg, 0.1 mmol) in dioxane (2174 μL) along with 0.5 M ammonia in dioxane (600 μL, 0.300 mmol) were added to an 8 mL vial to give a yellow solution. The vial was sealed and the reaction mixture was heated to 60° C. and stirred overnight. LCMS showed the reaction to be complete. The reaction mixture was concentrated and then taken up in DMF (1 mL). The crude product was purified by preparative HPLC using a 5-30% CH$_3$CN gradient in H$_2$O with 0.05% TFA. The pure fractions were combined and lyophilized to give a TFA salt of the title compound as a clear film (3.5 mg, 9.0%). $^1$H NMR (500 MHz, DMSO-d$_6$) δ ppm 1.23 (d, J=6.35 Hz, 3 H), 3.61 (s, 3 H), 3.85 (s, 3 H), 5.21-5.28 (m, 1 H), 6.35 (s, 2 H), 6.43 (d, J=1.95 Hz, 1 H), 6.57 (s, 2 H), 6.62-6.65 (m, 1 H), 6.81 (d, J=7.32 Hz, 1 H), 7.58 (d, J=1.95 Hz, 1 H), 7.77 (d, J=3.42 Hz, 1 H), 7.92 (d, J=0.98 Hz, 1 H); ESI-MS m/z [M+H]$^+$ calc'd for C$_{19}$H$_{20}$N$_{10}$, 389.19; found 389.6.

Example 3

(S)-2-Amino-4-methyl-6-((1-(1-methyl-6-(1-methyl-1H-pyrazol-5-yl)-1H-pyrrolo[3,2-b]pyridin-5-yl)ethyl)amino)pyrimidine-5-carbonitrile

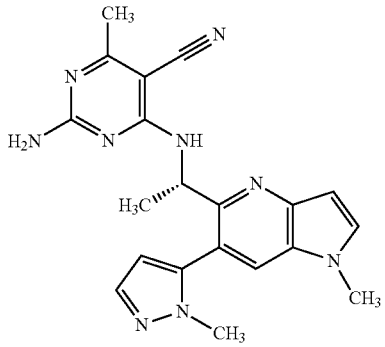 [SMILES: Cc1nc(N)nc(N[C@@H](C)c2nc3ccn(C)c3cc2-c2ccnn2C)c1C#N]

(S)-4-Methyl-6-((1-(1-methyl-6-(1-methyl-1H-pyrazol-5-yl)-1H-pyrrolo[3,2-b]pyridin-5-yl)ethyl)amino)-2-(methylsulfonyl)pyrimidine-5-carbonitrile (174 mg, 0.386 mmol) in dioxane (8396 μL) along with 0.5 M ammonia in dioxane (2317 μL, 1.159 mmol) were added to a vial to give a yellow solution. The vial was sealed and the reaction mixture was heated to 60° C. and stirred overnight. The reaction mixture was subsequently concentrated and taken up in DMF (1 mL). The crude product was purified by preparative HPLC using a 5-30% $CH_3CN$ gradient in $H_2O$ with 0.05% TFA. The pure fractions were combined and lyophilized to give a TFA salt of the title compound as a clear film (15.6 mg, 0.040 mmol, 10.4%). $^1$H NMR (500 MHz, $CD_3OD$) δ ppm 1.51 (d, J=6.83 Hz, 3 H), 2.53 (s, 3 H), 3.70 (s, 3 H), 3.95 (s, 3 H), 5.53-5.59 (m, 1 H), 6.51 (d, J=1.95 Hz, 1 H), 6.77-6.78 (m, 1H), 7.62 (d, J=1.95 Hz, 1H), 7.80 (d, J=2.93 Hz, 1H), 8.08 (s, 1H); ESI-MS m/z $[M+H]^+$ calc'd for $C_{20}H_{21}N_9$, 388.19; found 388.6.

Example 4

(S)-2-Amino-4-((1-(1-methyl-6-(1-methyl-1H-pyrazol-5-yl)-1H-pyrrolo[3,2-b]pyridin-5-yl)ethyl)amino)pyrimidine-5-carbonitrile

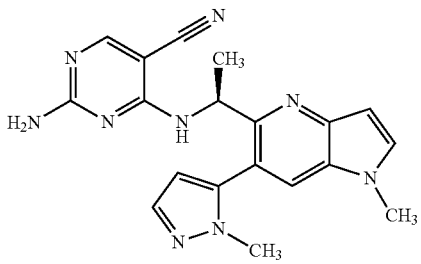 [SMILES: C[C@H](Nc1nc(N)ncc1C#N)c1nc2ccn(C)c2cc1-c1ccnn1C]

A mixture of (S)-2-chloro-4-((1-(1-methyl-6-(1-methyl-1H-pyrazol-5-yl)-1H-pyrrolo[3,2-b]pyridin-5-yl)ethyl)amino)pyrimidine-5-carbonitrile (60 mg, 0.153 mmol) in dioxane (1 mL) and ammonium hydroxide (1 mL, 7.19 mmol) was heated at 100° C. in a microwave reactor for 1 hour. The reaction mixture was subsequently concentrated and purified by preparative HPLC (basic mode, 25% to 50% ACN/water gradient) to give the title compound as an off-white solid (14.2 mg, 24.9%). $^1$H NMR (500 MHz, $CD_3OD$) δ ppm 1.41 (br s, 3 H), 3.59-3.74 (m, 3 H), 3.86-3.92 (m, 3 H), 5.16-5.36 (m, 1 H), 6.39-6.50 (m, 1 H), 6.63-6.73 (m, 1 H), 7.57-7.67 (m, 2 H), 7.77-7.88 (m, 1H), 8.04-8.13 (m, 1H); ESI-MS m/z $[M+H]^+$ calc'd for $C_{19}H_{19}N_9$, 374.18; found 374.3.

Example 5

(S)-5-Chloro-$N^4$-(1-(1-methyl-6-morpholino-1H-pyrrolo[3,2-b]pyridin-5-yl)ethyl)pyrimidine-2,4-diamine

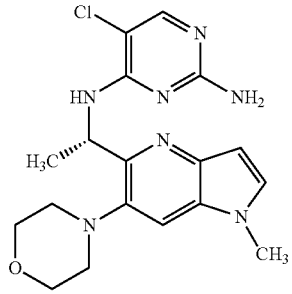 [SMILES: C[C@H](Nc1nc(N)ncc1Cl)c1nc2ccn(C)c2cc1N1CCOCC1]

(S)-1-(1-Methyl-6-morpholino-1H-pyrrolo[3,2-b]pyridin-5-yl)ethanamine (76 mg, 0.290 mmol), 4,5-dichloropyrimidin-2-amine (50 mg, 0.305 mmol), and N-ethyl-N-isopropylpropan-2-amine (0.155 mL, 0.871 mmol) were combined in acetonitrile (4 mL) and the resulting mixture was heated in a sealed tube at 128° C. in a microwave reactor for 1 hour. The reaction mixture was subsequently concentrated and purified by preparative HPLC (10% to 30% ACN/water gradient with 0.035% TFA) to give a TFA salt of the title compound as a white solid (28%). $^1$H NMR (500 MHz, $CD_3OD$) δ ppm 7.79 (s, 1H), 7.69 (s, 1H), 7.44 (d, 1H, J=3.5 Hz), 6.57 (d, 1H, J=3.5 Hz), 6.10 (q, 1H, J=7.0 Hz), 3.88-4.00 (m, 4H), 3.84 (s, 3H), 3.10-3.20 (m, 2H), 2.81-2.90 (m, 2H), 1.52 (d, 3H, J=7.0 Hz); ESI-MS m/z $[M+H]^+$ calc'd for $C_{18}H_{22}ClN_7O$, 388.3; found 388.3.

Example 6

4-Amino-2-methyl-6-((1-(1-methyl-6-morpholino-1H-pyrrolo[3,2-b]pyridin-5-yl)ethyl)amino)pyrimidine-5-carbonitrile

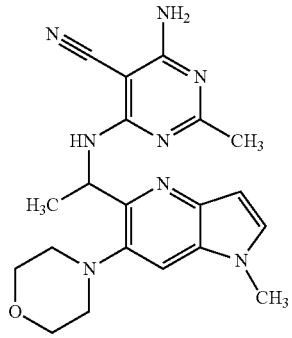 [SMILES: Cc1nc(N)c(C#N)c(NC(C)c2nc3ccn(C)c3cc2N2CCOCC2)n1]

1-(1-Methyl-6-morpholino-1H-pyrrolo[3,2-b]pyridin-5-yl)ethanamine (50 mg, 0.192 mmol), 4-amino-6-chloro-2-methylpyrimidine-5-carbonitrile (35.6 mg, 0.211 mmol), and N-ethyl-N-isopropylpropan-2-amine (0.103 mL, 0.576 mmol) were combined in acetonitrile (4 mL) and the resulting mixture was heated in a sealed tube at 128° C. for 1 hour in a microwave reactor. The reaction mixture was subsequently concentrated and purified by preparative HPLC (10% to 35% ACN/water gradient with 0.03% TFA) and dried under vacuum to give a TFA salt of the title compound as a white solid (42 mg, 56%). $^1$H NMR (500 MHz, CD$_3$OD) δ ppm 7.93 (s, 1H), 7.53 (d, 1H, J=3.5 Hz), 6.65 (d, 1H, J=3.5 Hz), 6.17 (q, 1H, J=7.0 Hz), 3.91-4.02 (m, 4H), 3.91 (s, 3H), 3.33-3.40 (m, 2H), 2.87-2.95 (m, 2H), 2.26 (s, 3H), 1.60 (d, 3H, J=7.0 Hz); ESI-MS m/z [M+H]$^+$ calc'd for C$_{20}$H$_{24}$N$_8$O, 393; found 393.

Example 7

(S)-5-Fluoro-N$^4$-(1-(1-methyl-6-(1-methyl-1H-pyrazol-5-yl)-1H-pyrrolo[3,2-b]pyridin-5-yl)ethyl)pyrimidine-2,4-diamine

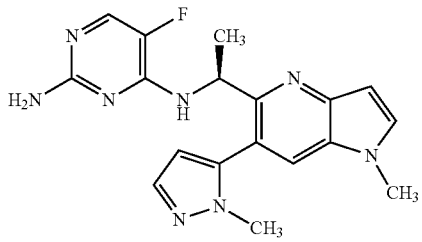

A suspension of (S)-2-chloro-5-fluoro-N-(1-(1-methyl-6-(1-methyl-1H-pyrazol-5-yl)-1H-pyrrolo[3,2-b]pyridin-5-yl)ethyl)pyrimidin-4-amine (136 mg, 0.352 mmol) in NH$_4$OH (4 mL) was heated to 100° C. in a microwave reactor for 1.5 hours. UPLC showed only starting material, so the reaction was heated to 120° C. in an oil bath for 6 hours. UPLC showed 30% starting material and the reaction was stopped. Solvent was removed in vacuo. The resulting residue was diluted with MeOH and DCM, and was purified via preparative HPLC using 15-25% ACN gradient in water with 0.35% TFA. The fractions were collected and solvent was removed in vacuo to give a TFA salt of the title compound (27.4 mg, 21.2%). $^1$H NMR (500 MHz, CD$_3$OD) δ ppm 1.54 (d, J=6.83 Hz, 3 H), 3.68 (d, J=1.95 Hz, 4H), 3.92 (s, 3 H), 5.59 (d, J=6.83 Hz, 1 H), 6.43-6.51 (m, 1 H), 6.75 (br s, 1 H), 7.54-7.63 (m, 1 H), 7.72-7.86 (m, 2 H), 8.03 (s, 1 H); ESI-MS m/z [M+H]$^+$ calc'd for C$_{18}$H$_{19}$FN$_8$, 367. found 367.

Example 8

(S)-4-Amino-2-hydroxy-6-((1-(1-methyl-6-morpholino-1H-pyrrolo[3,2-b]pyridin-5-yl)ethyl)amino)pyrimidine-5-carbonitrile

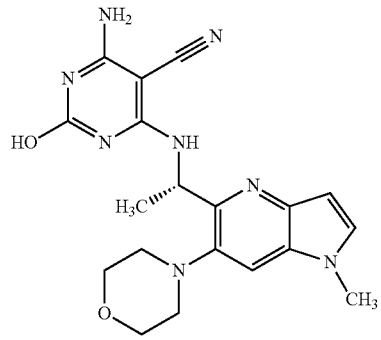 [SMILES: C[C@H](Nc1nc(O)nc(N)c1C#N)c1nc2ccn(C)c2cc1N1CCOCC1]

(S)-4-Amino-6-((1-(1-methyl-6-morpholino-1H-pyrrolo[3,2-b]pyridin-5-yl)ethyl)amino)-2-(methylsulfonyl)pyrimidine-5-carbonitrile (66 mg, 0.145 mmol) in THF (2 mL) was combined with sodium hydroxide (0.289 mL, 0.289 mmol) to give a yellow solution, which was heated to 50° C. and stirred for 3 hours. The product was purified by LC/MS using a 5-30% CH$_3$CN gradient in H$_2$O with 0.035% formic acid. The pure fractions were combined and lyophilized to give a formic acid salt of the title compound as a white solid (7 mg, 12%). $^1$H NMR (400 MHz, DMSO-d$_6$) δ ppm 1.32-1.46 (m, 3 H), 2.70-2.85 (m, 2H), 3.00-3.13 (m, 2 H), 3.81 (s, 8 H), 5.67-5.86 (m, 1 H), 6.43-6.53 (m, 1 H), 7.05-7.23 (m, 1 H), 7.27-7.45 (m, 2 H), 7.52-7.64 (m, 1 H), 7.85-7.94 (m, 1 H); ESI-MS m/z [M+H]$^+$ calc'd for C$_{19}$H$_{22}$N$_8$O$_2$, 395.4; found 395.5.

Example 9

(S)-2-Amino-4-methyl-6-((1-(1-methyl-6-morpholino-1H-pyrrolo[3,2-b]pyridin-5-yl)ethyl)amino)pyrimidine-5-carbonitrile

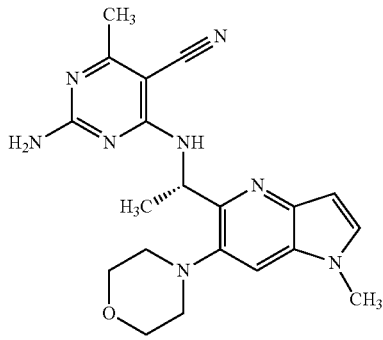 [SMILES: Cc1nc(N)nc(N[C@@H](C)c2nc3ccn(C)c3cc2N2CCOCC2)c1C#N]

(S)-4-Methyl-6-((1-(1-methyl-6-morpholino-1H-pyrrolo[3,2-b]pyridin-5-yl)ethyl)amino)-2-(methylsulfonyl)pyrimidine-5-carbonitrile (15 mg, 0.033 mmol) in dioxane (2 mL) was combined with ammonia in dioxane 0.5 M (0.198 mL, 0.099 mmol) to give a yellow solution, which was stirred for 6 hours at room temperature. The product was purified by LC/MS using a 20-45% CH$_3$CN gradient in H$_2$O with 0.035% formic acid. The pure fractions were combined and lyophilized to give a formic acid salt of the title compound as a white solid (2 mg, 17%). $^1$H NMR (400 MHz, DMSO-d$_6$) δ ppm 1.34-1.47 (m, 3 H), 2.17-2.28 (m, 3 H), 2.70-2.85 (m, 2 H), 2.96-3.13 (m, 2 H), 3.67-3.92 (m, 8 H), 5.82-5.97 (m, 1 H), 6.45-6.59 (m, 1 H), 6.87-6.98 (m, 2 H), 7.52-7.62 (m, 1 H), 7.82-7.91 (m, 1 H); ESI-MS m/z [M+H]$^+$ calc'd for C$_{20}$H$_{24}$N$_8$O$_3$S, 393.4; found 393.4.

Example 10

(S)-2,4-Diamino-6-((1-(1-methyl-6-morpholino-1H-pyrrolo[3,2-b]pyridin-5-yl)ethyl)amino)pyrimidine-5-carbonitrile

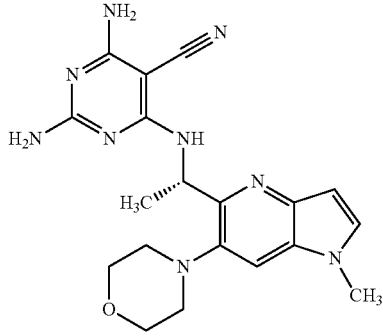 [SMILES: C[C@H](Nc1nc(N)nc(N)c1C#N)c1nc2ccn(C)c2cc1N1CCOCC1]

(S)-4-Amino-6-((1-(1-methyl-6-morpholino-1H-pyrrolo[3,2-b]pyridin-5-yl)ethyl)amino)-2-(methylsulfonyl)pyrimidine-5-carbonitrile (108 mg, 0.237 mmol) in dioxane (3 mL)

was combined with 0.5 M ammonia in dioxane (1.419 mL, 0.710 mmol) to give a yellow solution, which was stirred overnight at 60° C. The product was purified by LC/MS using a 5-30% $CH_3CN$ gradient in $H_2O$ with 0.035% formic acid. The pure fractions were combined and lyophilized to give a formic acid salt of the title compound as a white solid (14 mg, 15%). $^1H$ NMR (400 MHz, DMSO-$d_6$) δ ppm 1.43-1.59 (m, 3 H), 2.74-2.87 (m, 2 H), 3.03-3.17 (m, 2 H), 3.70-3.99 (m, 8 H), 5.76-5.91 (m, 1 H), 6.52-6.69 (m, 1H), 7.45-7.48 (br s, 2 H), 7.52-7.62 (m, 1 H), 7.75-7.79 (br s, 2 H), 7.82-7.91 (m, 1 H); ESI-MS m/z [M+H]$^+$ calc'd for $C_{19}H_{23}N_9O$, 394.4; found 394.5.

Example 11

(S)-4-Amino-2-hydroxy-6-((1-(1-methyl-6-(1-methyl-1H-pyrazol-5-yl)-1H-pyrrolo[3,2-b]pyridin-5-yl)ethyl)amino)pyrimidine-5-carbonitrile

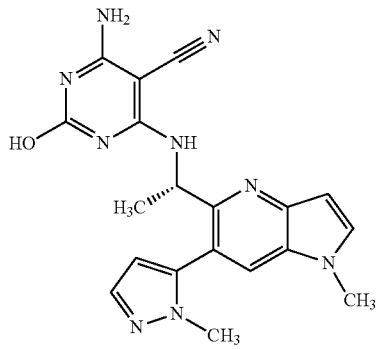 [SMILES: C[C@H](Nc1nc(O)nc(N)c1C#N)c1nc2ccn(C)c2cc1-c1ccnn1C]

(S)-4-Amino-6-((1-(1-methyl-6-(1-methyl-1H-pyrazol-5-yl)-1H-pyrrolo[3,2-b]pyridin-5-yl)ethyl)amino)-2-(methylthio)pyrimidine-5-carbonitrile (322 mg, 0.768 mmol) in ethanol (6 mL) was combined with concentrated hydrochloric acid (1 mL, 12 mmol), and the resulting mixture was heated at 85° C. in a microwave reactor for 12 hours. The reaction mixture was subsequently concentrated and purified twice by preparative HPLC (5% to 20% ACN/water gradient with 0.035% TFA) to give a TFA salt of the title compound as an off-white solid (14.4 mg, 4.81%). $^1H$ NMR (500 MHz, $CD_3OD$) δ ppm 1.58 (d, J=6.83 Hz, 3 H), 3.85 (s, 3 H), 4.00 (s, 3 H), 5.20 (br s, 1 H), 6.64 (br s, 1 H), 6.82 (d, J=2.93 Hz, 1 H), 7.64 (d, J=1.46 Hz, 1 H), 7.98 (br s, 1 H), 8.42 (br s, 1 H); ESI-MS m/z [M+H]$^+$ calc'd for $C_{19}H_{19}N_9O$, 390.2; found 390.5.

Example 12

(S)-2,4-Diamino-6-((1-(1-methyl-6-(pyridin-2-yl)-1H-pyrrolo[3,2-b]pyridin-5-yl)ethyl)amino)pyrimidine-5-carbonitrile

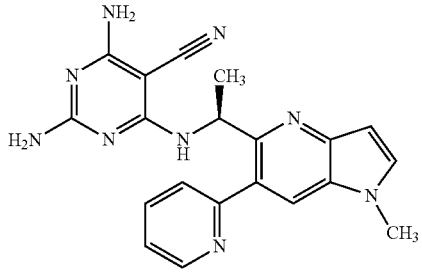 [SMILES: C[C@H](Nc1nc(N)nc(N)c1C#N)c1nc2ccn(C)c2cc1-c1ccccn1]

A solution of (S)-1-(1-methyl-6-(pyridin-2-yl)-1H-pyrrolo[3,2-b]pyridin-5-yl)ethanamine hydrochloride (50 mg, 0.198 mmol), 2,4-diamino-6-chloropyrimidine-5-carbonitrile (50.4 mg, 0.297 mmol), and N-ethyl-N-isopropylpropan-2-amine (0.104 mL, 0.594 mmol) in acetonitrile (6 mL), was heated in a microwave reactor at 120° C. for 2 hours. After cooling to room temperature, the reaction mixture was concentrated, re-dissolved in DMF, and purified by preparative HPLC (basic mode) using a 20-30% $CH_3CN$ gradient in $H_2O$. The desired fractions were combined and solvent was removed in vacuo. The residue was purified again by preparative HPLC (basic mode) using a 25-35% $CH_3CN$ gradient in $H_2O$. The pure fractions were combined and the solvent was removed in vacuo to give the title compound as a colorless film (24 mg, 31%). $^1H$ NMR (500 MHz, $CD_3OD$) δ ppm 1.59 (d, J=7.32 Hz, 3 H), 4.04 (br s, 3 H), 5.84 (q, J=7.32 Hz, 1 H), 6.88 (d, J=3.42 Hz, 1 H), 7.62-7.68 (m, 1 H), 7.90 (d, J=7.81 Hz, 1 H), 8.08 (d, J=2.93 Hz, 1 H), 8.16 (td, J=7.81, 1.95 Hz, 1H), 8.66 (s, 1H), 8.83 (d, J=4.88 Hz, 1H). ESI-MS m/z [M+H]$^+$ calc'd for $C_{20}H_{19}N_9$, 386. found 386.

Example 13

(S)-2,4-Diamino-6-((1-(1-methyl-6-(1H-pyrazol-5-yl)-1H-pyrrolo[3,2-b]pyridin-5-yl)ethyl)amino)pyrimidine-5-carbonitrile

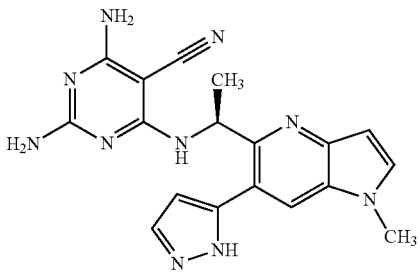 [SMILES: C[C@H](Nc1nc(N)nc(N)c1C#N)c1nc2ccn(C)c2cc1-c1ccn[nH]1]

A solution of (S)-1-(1-methyl-6-(1H-pyrazol-5-yl)-1H-pyrrolo[3,2-b]pyridin-5-yl)ethanamine hydrochloride (500 mg, 1.8 mmol), 2,4-diamino-6-chloropyrimidine-5-carbonitrile (458 mg, 2.70 mmol), and N-ethyl-N-isopropylpropan-2-amine (0.941 mL, 5.40 mmol) were combined in acetonitrile (10 mL). The reaction mixture was heated in a microwave reactor at 120° C. for 2 hours and then concentrated in vacuo. The residue was diluted with MeOH/DMSO and purified by preparative HPLC (acid mode) eluting with 1-20% ACN in water. The fractions containing the desired product were pooled and then concentrated in vacuo to give a TFA salt of the title compound (84 mg, 12%). $^1H$ NMR (500 MHz, $CD_3OD$) δ ppm 1.61 (d, J=7.32 Hz, 3 H), 4.05 (s, 3 H), 5.91 (q, J=7.16 Hz, 1 H), 6.79 (dd, J=6.10, 2.68 Hz, 2 H), 7.89 (s, 1 H), 7.97 (d, J=2.93 Hz, 1 H), 8.57 (s, 1 H); ESI-MS m/z [M+H]$^+$ calc'd for $C_{18}H_{18}N_{10}$, 375; found 375.

Example 14

2,4-Diamino-6-(((1S)-1-(6-(3,5-dimethyl-1H-pyrazol-4-yl)-1-methyl-1H-pyrrolo[3,2-b]pyridin-5-yl)ethyl)amino)pyrimidine-5-carbonitrile

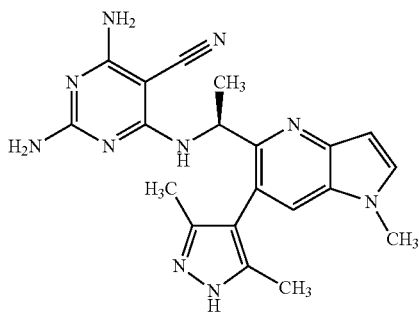 [SMILES: Cc1n[nH]c(C)c1-c1cc2c(ccn2C)nc1[C@H](C)Nc1nc(N)nc(N)c1C#N]

(1S)-1-(6-(3,5-Dimethyl-1H-pyrazol-4-yl)-1-methyl-1H-pyrrolo[3,2-b]pyridin-5-yl)ethanamine hydrochloride (123 mg, 0.403 mmol), 2,4-diamino-6-chloropyrimidine-5-carbonitrile (82 mg, 0.484 mmol), and N-ethyl-N-isopropylpropan-2-amine (211 µL, 1.21 mmol) were combined in acetonitrile (4030 µL). The reaction mixture was heated in a microwave reactor at 120° C. for 2 hours and then concentrated in vacuo. The residue was taken up in DMF and purified by preparative HPLC (basic mode) eluting with 30% ACN in water. The fractions containing the desired product were combined, concentrated, and lyophilized to give the title compound as an off-white solid (89 mg, 55%). $^1$H NMR (500 MHz, DMSO-$d_6$) δ ppm 1.12 (d, J=6.35 Hz, 3 H), 1.92 (br s, 3 H), 2.06 (br s, 3 H), 3.82 (s, 3H), 5.20 (br s, 1 H), 6.43 (br s, 2 H), 6.53-6.60 (m, 3 H), 6.96 (br s, 1 H), 7.62-7.69 (m, 2H), 12.36 (br s, 1 H); ESI-MS m/z [M+H]$^+$ calc'd for $C_{26}H_{22}N_{10}$, 403; found 403.

Example 15

(S)-2,4-Diamino-6-((1-(6-(2-hydroxypyridin-4-yl)-1-methyl-1H-pyrrolo[3,2-b]pyridin-5-yl)ethyl)amino)pyrimidine-5-carbonitrile

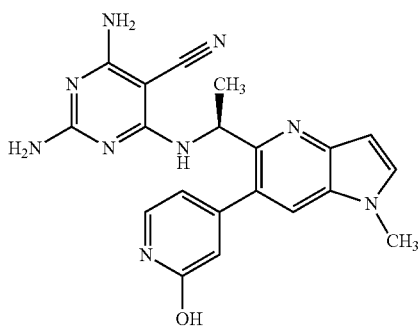 [SMILES: C[C@H](Nc1nc(N)nc(N)c1C#N)c1nc2ccn(C)c2cc1-c1ccnc(O)c1]

A mixture of (S)-1-(6-(2-(benzyloxy)pyridin-4-yl)-1-methyl-1H-pyrrolo[3,2-b]pyridin-5-yl)ethanamine hydrochloride (155 mg, 0.393 mmol) and (S)-4-(5-(1-aminoethyl)-1-methyl-1H-pyrrolo[3,2-b]pyridin-6-yl)pyridin-2-ol hydrochloride (120 mg, 0.393 mmol) along with 2,4-diamino-6-chloropyrimidine-5-carbonitrile (100 mg, 0.590 mmol) and N-ethyl-N-isopropylpropan-2-amine (0.205 mL, 1.18 mmol) were combined in acetonitrile (6 mL). The reaction mixture was heated in a microwave reactor at 120° C. for 2 hours and then concentrated. The residue was dissolved in MeOH (10 mL). Pd/C (10%, 700 mg) was added and the reaction mixture was maintained under an atmosphere of hydrogen for 30 minutes. The mixture was filtered through Celite and concentrated. The residue was taken up in DMF and purified by preparative HPLC (basic mode) eluting with 20-35% ACN in water. The fractions containing the desired product were combined and concentrated in vacuo to give the title compound (73 mg, 46%). $^1$H NMR (500 MHz, DMSO-$d_6$) δ ppm 1.22-1.32 (m, 3 H), 3.80 (br s, 3 H), 5.58 (quin, J=6.71 Hz, 1 H), 6.31 (d, J=6.83 Hz, 1 H), 6.48 (br s, 2 H), 6.52-6.63 (m, 5 H), 6.66 (d, J=7.81 Hz, 1 H), 7.52 (d, J=6.35 Hz, 1 H), 7.72 (d, J=2.93 Hz, 1 H), 7.80 (s, 1 H); ESI-MS m/z [M+H]$^+$ calc'd for $C_{20}H_{19}N_9O$, 402; found 402.

Example 16

(S)—$N^6$-(1-(1-Methyl-6-(1-methyl-1H-pyrazol-5-yl)-1H-pyrrolo[3,2-b]pyridin-5-yl)ethyl)-9H-purine-2,6-diamine

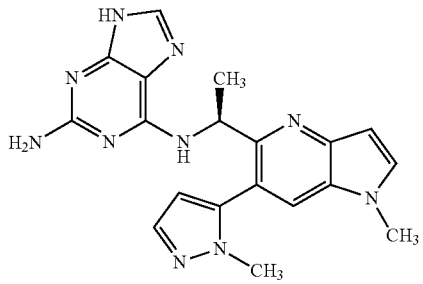 [SMILES: C[C@H](Nc1nc(N)nc2[nH]cnc12)c1nc2ccn(C)c2cc1-c1ccnn1C]

(S)-1-(1-Methyl-6-(1-methyl-1H-pyrazol-5-yl)-1H-pyrrolo[3,2-b]pyridin-5-yl)ethanamine hydrochloride (500 mg, 1.71 mmol), 6-chloro-9H-purin-2-amine (436 mg, 2.57 mmol), and N-ethyl-N-isopropylpropan-2-amine (0.895 mL, 5.14 mmol) were combined in acetonitrile (10 mL). The reaction mixture was heated in a microwave reactor at 120° C. for 2 hours and then concentrated. The residue was diluted with MeOH/DMSO and purified by preparative HPLC (basic mode) eluting with 20-30% ACN in water. The fractions containing the desired compound were collected and concentrated in vacuo. The residue was re-crystallized in an EtOAc/MeOH/hexane mixture to give the title compound (295 mg, 44.4%). $^1$H NMR (500 MHz, CD$_3$OD) δ ppm 1.50 (d, J=6.83 Hz, 3 H), 3.59-3.66 (m, 3 H), 3.89 (br s, 3 H), 5.56 (br s, 1 H), 6.45 (d, J=1.95 Hz, 1 H), 6.68-6.73 (m, 1 H), 7.58-7.65 (m, 2 H), 7.77-7.89 (m, 2 H); ESI-MS m/z [M+H]$^+$ calc'd for $C_{19}H_{20}N_{10}$, 389; found 389.

Example 17

(S)-2,4-Diamino-6-((1-(1-methyl-6-(thiazol-4-yl)-1H-pyrrolo[3,2-b]pyridin-5-yl)ethyl)amino)pyrimidine-5-carbonitrile

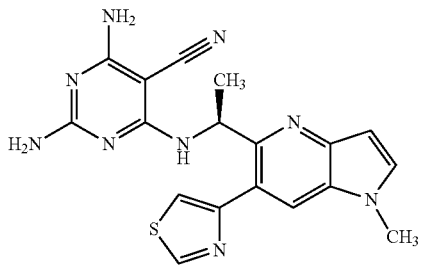 [SMILES: C[C@H](Nc1nc(N)nc(N)c1C#N)c1nc2ccn(C)c2cc1-c1cscn1]

To a sealed tube were added (S)-4-amino-6-((1-(1-methyl-6-(thiazol-4-yl)-1H-pyrrolo[3,2-b]pyridin-5-yl)ethyl)amino)-2-(methylsulfonyl)pyrimidine-5-carbonitrile (20 mg, 0.044 mmol) in dioxane (5 mL) along with 0.5M ammonia in dioxane (0.440 mL, 0.220 mmol). The reaction mixture was heated at 60° C. overnight and then concentrated. The crude product was taken up in DMF and purified by preparative HPLC (basic mode) eluting with 30-40% ACN in water. The fractions containing the desired product were combined and concentrated in vacuo to give the title compound as an off-white solid (12 mg, 70%). $^1$H NMR (500 MHz, CD$_3$OD) δ ppm 1.42 (d, J=6.83 Hz, 3 H), 3.87 (s, 3 H), 5.76 (d, J=6.83 Hz, 1 H), 6.60-6.67 (m, 1 H), 7.56 (s, 1 H), 7.76 (s, 1 H), 7.91 (d, J=0.98 Hz, 1 H), 9.16 (d, J=1.95 Hz, 1 H); ESI-MS m/z [M+H]$^+$ calc'd for C$_{18}$H$_{17}$N$_9$S, 392; found 392.

Example 18

(S)—N$^4$-(1-(1-Methyl-6-(1-methyl-1H-pyrazol-5-yl)-1H-pyrrolo[3,2-b]pyridin-5-yl)ethyl)-1H-pyrazolo[3,4-d]pyrimidine-4,6-diamine

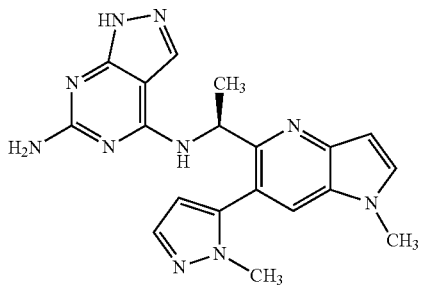 [SMILES: C[C@H](Nc1nc(N)nc2[nH]ncc12)c1nc2ccn(C)c2cc1-c1ccnn1C]

(S)-1-(1-Methyl-6-(1-methyl-1H-pyrazol-5-yl)-1H-pyrrolo[3,2-b]pyridin-5-yl)ethanamine hydrochloride (500 mg, 1.71 mmol), 4-chloro-1H-pyrazolo[3,4-d]pyrimidine-6-amine (436 mg, 2.57 mmol), and N-ethyl-N-isopropylpropan-2-amine (0.895 mL, 5.14 mmol) were combined in acetonitrile (10 mL). The reaction mixture was heated in a microwave reactor at 120° C. for 2 hours and then concentrated. The residue was diluted with MeOH/DMSO and purified by preparative HPLC (basic mode) eluting with 35% ACN in water. The fractions containing the desired product were combined and lyophilized to give the title compound as a pale yellow solid (360 mg, 54.2%). $^1$H NMR (500 MHz, DMSO-d$_6$) δ ppm 1.41 (d, J=6.83 Hz, 3 H), 3.59-3.68 (m, 3 H), 3.83 (s, 3 H), 5.57 (dd, J=13.42, 6.59 Hz, 3 H), 6.46 (d, J=1.46 Hz, 1 H), 6.61 (d, J=2.93 Hz, 1 H), 7.55 (d, J=1.46 Hz, 1 H), 7.72 (d, J=3.42 Hz, 1 H), 7.89 (s, 1 H), 7.95-8.03 (m, 2 H), 12.33 (br s, 1 H); ESI-MS m/z [M+H]$^+$ calc'd for C$_{19}$H$_{20}$N$_{10}$,389; found 389.

Example 19

(S)-2-Amino-4-methyl-6-((1-(1-methyl-6-(3-methyl-1H-pyrazol-4-yl)-1H-pyrrolo[3,2-b]pyridin-5-yl)ethyl)amino)pyrimidine-5-carbonitrile

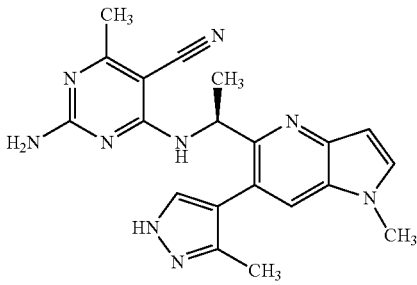 [SMILES: Cc1n[nH]cc1-c1cc2c(ccn2C)nc1[C@H](C)Nc1nc(N)nc(C)c1C#N]

To a sealed tube were added (S)-4-methyl-6-((1-(1-methyl-6-(3-methyl-1H-pyrazol-4-yl)-1H-pyrrolo[3,2-b]pyridin-5-yl)ethyl)amino)-2-(methylsulfonyl)pyrimidine-5-carbonitrile (30 mg, 0.067 mmol) in dioxane (5 mL) along with 0.5M ammonia in dioxane (0.666 mL, 0.333 mmol). The reaction mixture was heated at 60° C. overnight and then concentrated. The residue was taken up in DMF and purified by preparative HPLC (basic mode) eluting with 30% ACN in water. The fractions containing the desired compound were combined and concentrated in vacuo. The residue was purified again by preparative HPLC (acid mode) eluting with 5-20% ACN in water. The fractions containing the desired product were combined and concentrated in vacuo to give a TFA salt of the title compound as a colorless film (16.3 mg, 63%). $^1$H NMR (500 MHz, CD$_3$OD) δ ppm 1.56 (d, J=6.83 Hz, 3 H), 2.20-2.26 (m, 3 H), 2.47 (br s, 3 H), 4.01 (s, 3 H), 5.62-5.73 (m, 1 H), 6.80 (d, J=2.93 Hz, 1 H), 7.91 (d, J=2.93 Hz, 1 H), 8.27 (s, 1 H); ESI-MS m/z [M+H]$^+$ calc'd for C$_{20}$H$_{21}$N$_9$, 388. found 388.

Example 20

2,4-Diamino-6-((1-(6-(4-hydroxy-4-methylpiperidin-1-yl)-1-methyl-1H-pyrrolo[3,2-b]pyridin-5-yl)ethyl)amino)pyrimidine-5-carbonitrile

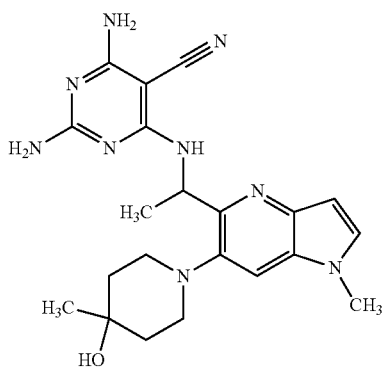 [SMILES: CC(Nc1nc(N)nc(N)c1C#N)c1nc2ccn(C)c2cc1N1CCC(C)(O)CC1]

To a 10 mL vial were added 1-(5-(1-aminoethyl)-1-methyl-1H-pyrrolo[3,2-b]pyridin-6-yl)-4-methylpiperidin-4-ol (56 mg, 0.194 mmol), 2,4-diamino-6-chloropyrimidine-5-carbonitrile (32.9 mg, 0.194 mmol) and Et$_3$N (0.054 mL, 0.388 mmol) in DMF (3 mL). The resulting yellow solution was heated to 90° C. and stirred overnight. The reaction mixture was purified by preparative HPLC eluting with 5-30% ACN in water (with 0.05% ammonium carbonate). The fractions containing the desired product were combined and lyophilized to give the title compound (racemate) as a white solid (40 mg, 49%). $^1$H NMR (400 MHz, DMSO-d$_6$) δ ppm 1.17-1.29 (m, 3 H), 1.32-1.43 (m, 3 H), 1.52-1.87 (m, 4 H), 2.57-2.72 (m, 2 H), 2.73-2.94 (m, 2 H), 3.16-3.29 (m, 1 H), 3.71-3.86 (m, 3 H), 4.24-4.32 (m, 1 H), 5.74-5.88 (m, 1 H), 6.34-6.44 (m, 2 H), 6.44-6.52 (m, 1 H), 6.53-6.65 (m, 3 H), 7.48-7.58 (m, 1 H), 7.77-7.84 (m, 1 H); ESI-MS m/z [M+H]$^+$ calc'd for C$_{21}$H$_{27}$N$_9$O, 422.2; found 422.5.

Example 21

(S)-2,4-Diamino-6-((1-(6-(4-hydroxy-4-methylpiperidin-1-yl)-1-methyl-1H-pyrrolo[3,2-b]pyridin-5-yl)ethyl)amino)pyrimidine-5-carbonitrile

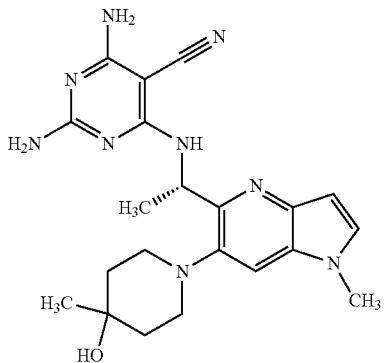 [SMILES: C[C@H](Nc1nc(N)nc(N)c1C#N)c1nc2ccn(C)c2cc1N1CCC(C)(O)CC1]

Example 22

(R)-2,4-Diamino-6-((1-(6-(4-hydroxy-4-methylpiperidin-1-yl)-1-methyl-1H-pyrrolo[3,2-b]pyridin-5-yl)ethyl)amino)pyrimidine-5-carbonitrile

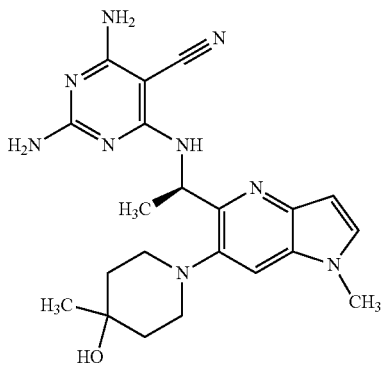 [SMILES: C[C@@H](Nc1nc(N)nc(N)c1C#N)c1nc2ccn(C)c2cc1N1CCC(C)(O)CC1]

Racemic 2,4-diamino-6-((1-(6-(4-hydroxy-4-methylpiperidin-1-yl)-1-methyl-1H-pyrrolo[3,2-b]pyridin-5-yl)ethyl)amino)pyrimidine-5-carbonitrile (40 mg, 49%) was resolved by Gilson supercritical fluid chromatography (ChiralPak™ AS, 5 μm, 20×150 mm) eluting with 25% MeOH (with 0.1% DEA) in liquid CO$_2$ flowing at 50 mL/min over a 10-minute period. EXAMPLE 21 stereoisomer was contained in fractions collected at the earliest retention time and was assigned S-stereochemical configuration. ESI-MS m/z [M+H]$^+$ calc'd for C$_{21}$H$_{27}$N$_9$O, 422.2; found 422.5. EXAMPLE 22 stereoisomer was contained in fractions collected at the later retention time and was assigned R-stereochemical configuration. ESI-MS m/z [M+H]$^+$ calc'd for C$_{21}$H$_{27}$N$_9$O, 422.2; found 422.5

Example 23

(S)-2-Amino-4-((1-(6-(2-hydroxypyridin-4-yl)-1-methyl-1H-pyrrolo[3,2-b]pyridin-5-yl)ethyl)amino)-6-methylpyrimidine-5-carbonitrile

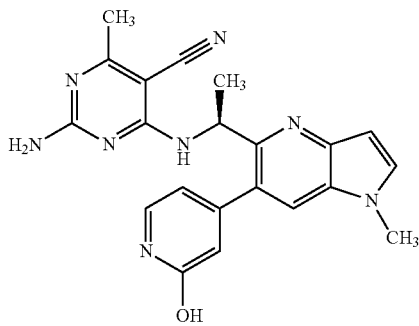 [SMILES: Cc1nc(N)nc(N[C@@H](C)c2nc3ccn(C)c3cc2-c2ccnc(O)c2)c1C#N]

(S)-1-(6-(2-(Benzyloxy)pyridin-4-yl)-1-methyl-1H-pyrrolo[3,2-b]pyridin-5-yl)ethanamine hydrochloride (187 mg, 0.475 mmol), 2-amino-4-chloro-6-methylpyrimidine-5-carbonitrile (80 mg, 0.475 mmol), and N-ethyl-N-isopropylpropan-2-amine (0.248 mL, 1.42 mmol) were combined in acetonitrile (6 mL). The reaction mixture was heated in a microwave reactor at 120° C. for 2 hours and then concentrated. The residue was taken up in MeOH (10 mL). Pd/C (10%, 700 mg) was added and the reaction mixture was maintained under an atmosphere of hydrogen for 30 minutes. The mixture was filtered through Celite and concentrated. The residue was taken up in DMF and purified by preparative HPLC (acid mode) eluting with 1-15% ACN in water. The fractions containing the desired product were combined and concentrated in vacuo to give a TFA salt of the title compound (48 mg, 25%). $^1$H NMR (500 MHz, CD$_3$OD) δ ppm 1.42 (d, J=6.35 Hz, 3 H), 2.32 (s, 3 H), 3.87 (s, 3 H), 5.70-5.77 (m, 1 H), 6.53-6.56 (m, 1 H), 6.64 (dd, J=3.42, 0.98 Hz, 1 H), 6.77 (d, J=0.98 Hz, 1 H), 7.55 (d, J=6.83 Hz, 1 H), 7.59 (d, J=3.42 Hz, 1 H), 7.76 (d, J=0.98 Hz, 1 H); ESI-MS m/z [M+H]$^+$ calc'd for C$_{21}$H$_{20}$N$_8$O, 401; found 401.

Example 24

(S)-2-Amino-4-methyl-6-((1-(1-methyl-6-(pyridin-2-yl)-1H-pyrrolo[3,2-b]pyridin-5-yl)ethyl)amino)pyrimidine-5-carbonitrile

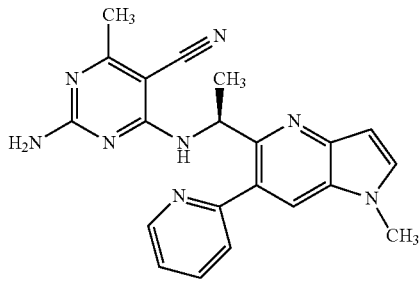 [SMILES: Cc1nc(N)nc(N[C@@H](C)c2nc3ccn(C)c3cc2-c2ccccn2)c1C#N]

(S)-1-(1-Methyl-6-(pyridin-2-yl)-1H-pyrrolo[3,2-b]pyridin-5-yl)ethanamine hydrochloride (151 mg, 0.522 mmol), 2-amino-4-chloro-6-methylpyrimidine-5-carbonitrile (80 mg, 0.475 mmol), and N-ethyl-N-isopropylpropan-2-amine (0.248 mL, 1.42 mmol) were combined in acetonitrile (6 mL). The reaction mixture was heated in a microwave reactor at 120° C. for 2 hours and then concentrated. The residue was taken up in DMF and purified by preparative HPLC (basic mode) eluting with 20-35% ACN in water. The fractions containing the desired compound were combined and concentrated in vacuo. The residue was taken up in DMF and further purified by preparative HPLC (acid mode) eluting with 1-25% ACN in water. The fractions containing the desired compound were combined, neutralized with NaHCO$_3$, and extracted with EtOAc (200 mL). The organic layers were combined, dried over Na$_2$SO$_4$, and concentrated in vacuo to give the title compound (53 mg, 29%). $^1$H NMR (500 MHz, CD$_3$OD) δ ppm 1.34-1.41 (m, 3 H), 2.31 (d, J=1.46 Hz, 3 H), 3.88 (d, J=1.46 Hz, 3H), 5.68-5.79 (m, 1 H), 6.67 (d, J=2.44 Hz, 1 H), 7.47 (dd, J=7.32, 4.88 Hz, 1 H), 7.58-7.61 (m, 1 H), 7.67 (d, J=7.81 Hz, 1 H), 7.86 (s, 1 H), 7.99 (t, J=7.81 Hz, 1 H), 8.68-8.73 (m, 1 H); ESI-MS m/z [M+H]$^+$ calc'd for C$_{21}$H$_{20}$N$_8$, 385; found 385.

Example 25

(S)-2-Amino-4-methyl-6-((1-(1-methyl-6-(tetrahydro-2H-pyran-4-yl)-1H-pyrrolo[3,2-b]pyridin-5-yl)ethyl)amino)pyrimidine-5-carbonitrile

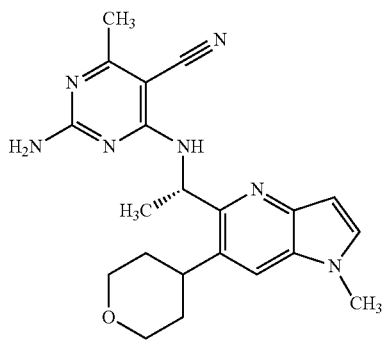

To a 10 mL vial were added (S)-1-(1-methyl-6-(tetrahydro-2H-pyran-4-yl)-1H-pyrrolo[3,2-b]pyridin-5-yl)ethanamine (271 mg, 1.05 mmol), 2-amino-4-chloro-6-methylpyrimidine-5-carbonitrile (194 mg, 1.149 mmol) and Et$_3$N (0.29 mL, 2.1 mmol) in DMF (5 mL). The resulting yellow solution was heated to 90° C. and stirred overnight. The product was purified by preparative HPLC eluting with 20-40% ACN in water (with 0.05% ammonium formate). The fractions containing the product were combined and lyophilized to give the title compound as a white solid (27 mg, 6.6%). $^1$H NMR (400 MHz, DMSO-d$_6$) δ ppm 1.39-1.53 (m, 3 H), 1.58-1.86 (m, 3 H), 1.91-2.11 (m, 1 H), 2.18-2.29 (m, 3 H), 2.99-3.17 (m, 1 H), 3.37-3.61 (m, 2 H), 3.75-3.90 (m, 3 H), 3.90-4.10 (m, 2 H), 5.63-5.80 (m, 1 H), 6.44-6.57 (m, 1 H), 6.97-7.25 (m, 2 H), 7.32-7.45 (m, 1 H), 7.55-7.65 (m, 1 H), 7.83-7.97 (m, 1 H); ESI-MS m/z [M+H]$^+$ calc'd for C$_{21}$H$_{25}$N$_7$O, 392; found 392.

Example 26

(S)-2,4-Diamino-6-((1-(1-methyl-6-(tetrahydro-2H-pyran-4-yl)-1H-pyrrolo[3,2-b]pyridin-5-yl)ethyl)amino)pyrimidine-5-carbonitrile

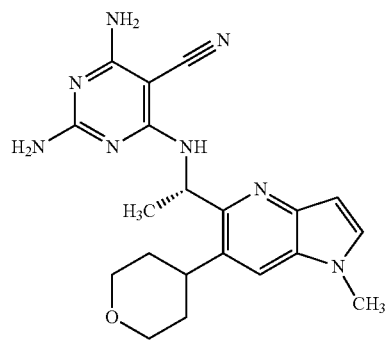

To a 20 mL vial were added (S)-1-(1-methyl-6-(tetrahydro-2H-pyran-4-yl)-1H-pyrrolo[3,2-b]pyridin-5-yl)ethanamine (336 mg, 1.296 mmol), 2,4-diamino-6-chloropyrimidine-5-carbonitrile (242 mg, 1.425 mmol) and Et$_3$N (1.8 mL, 13 mmol) in DMF (7 mL). The resulting yellow solution was heated to 90° C. and stirred overnight. The crude product was purified by preparative HPLC eluting with 25-50% ACN in water (with 0.05% ammonium bicarbonate). The fractions containing the desired product were combined and lyophilized to give the title compound as a white solid (147 mg, 28%). $^1$H NMR (400 MHz, DMSO-d$_6$) δ ppm 1.37-1.51 (m, 3 H), 1.58-1.87 (m, 3 H), 1.91-2.07 (m, 1 H), 3.04-3.18 (m, 1 H), 3.43-3.60 (m, 3 H), 3.77-3.88 (m, 3 H), 3.90-4.08 (m, 2 H), 5.64-5.80 (m, 1H), 6.39-6.54 (m, 3 H), 6.56-6.67 (m, 2 H), 6.82-6.96 (m, 1 H), 7.54-7.66 (m, 1 H), 7.81-7.96 (m, 1 H),); ESI-MS m/z [M+H]$^+$ calc'd for C$_{20}$H$_{24}$N$_8$O, 393; found 393.

Example 27

(S)—N$^6$-(1-(1-Methyl-6-morpholino-1H-pyrrolo[3,2-b]pyridin-5-yl)ethyl)-9H-purine-2,6-diamine

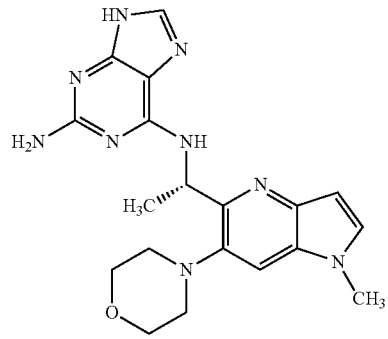 [SMILES: C[C@H](Nc1nc(N)nc2[nH]cnc12)c1nc2ccn(C)c2cc1N1CCOCC1]

To a 10 mL vial were added (S)-1-(1-methyl-6-morpholino-1H-pyrrolo[3,2-b]pyridin-5-yl)ethanamine (100 mg, 0.384 mmol), 6-chloro-9H-purin-2-amine (65.1 mg, 0.384 mmol) and Et$_3$N (0.11 mL, 0.77 mmol) in DMF (3 mL). The resulting yellow solution was heated to 90° C. and stirred overnight. The reaction mixture was purified by preparative HPLC eluting with 20-40% ACN in water (with 0.05% ammonium formate). The fractions containing the desired product were combined and lyophilized to give the title compound as a white solid (38 mg, 25%). $^1$H NMR (400 MHz, DMSO-$d_6$) δ ppm 1.38-1.52 (m, 4 H), 2.68-2.86 (m, 3 H), 3.01-3.18 (m, 3 H), 3.69-3.95 (m, 9 H), 5.62-5.82 (m, 2 H), 5.88-6.08 (m, 1 H), 6.46-6.59 (m, 2 H), 6.74-6.92 (m, 1 H), 7.52-7.59 (m, 1 H), 7.59-7.74 (m, 1 H), 7.76-7.90 (m, 1 H), 12.00-12.22 (m, 1 H); ESI-MS m/z [M+H]$^+$ calc'd for $C_{19}H_{23}N_9O$, 394. found 394.

Example 28

(S)-5-Chloro-$N^4$-(1-(1-methyl-6-morpholino-1H-pyrrolo[3,2-b]pyridin-5-yl)ethyl)pyrimidine-2,4,6-triamine

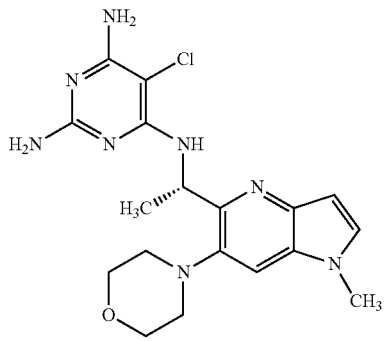 [SMILES: C[C@H](Nc1nc(N)nc(N)c1Cl)c1nc2ccn(C)c2cc1N1CCOCC1]

To a 10 mL vial were added (S)-1-(1-methyl-6-morpholino-1H-pyrrolo[3,2-b]pyridin-5-yl)ethanamine (100 mg, 0.384 mmol), 5,6-dichloropyrimidine-2,4-diamine (68.8 mg, 0.384 mmol) and Et$_3$N (0.11 mL, 0.77 mmol) in DMF (3 mL). The resulting yellow solution was heated to 90° C. and stirred overnight. The reaction mixture was purified by preparative HPLC eluting with 20-40% ACN in water (with 0.05% ammonium formate). The fractions containing the desired product were combined and lyophilized to give the title compound as a white solid (22 mg, 14%). $^1$H NMR (400 MHz, DMSO-$d_6$) δ ppm 1.31-1.41 (m, 3 H), 2.70-2.82 (m, 2 H), 3.00-3.15 (m, 3 H), 3.69-3.93 (m, 10 H), 5.55-5.67 (m, 2H), 5.79-5.89 (m, 1 H), 5.89-5.96 (m, 2 H), 6.11-6.22 (m, 1 H), 6.47-6.57 (m, 1 H), 7.49-7.59 (m, 1 H), 7.75-7.84 (m, 1 H); ESI-MS m/z [M+H]$^+$ calc'd for $C_{18}H_{23}ClN_8O$, 403. found 403.

Example 29

(S)-2,4-Diamino-6-((1-(1-methyl-6-morpholino-1H-pyrrolo[3,2-b]pyridin-5-yl)ethyl)amino)pyrimidine-5-carbonitrile

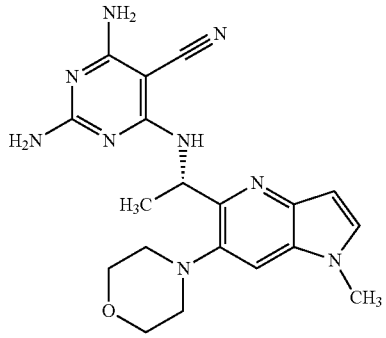 [SMILES: C[C@H](Nc1nc(N)nc(N)c1C#N)c1nc2ccn(C)c2cc1N1CCOCC1]

To a 25-mL three-neck round bottom flask equipped with a stir bar, thermocouple, and condenser under nitrogen were added (S)-1-(1-methyl-6-morpholino-1H-pyrrolo[3,2-b]pyridin-5-yl)ethan-1-amine, (S)-mandelic acid salt (1.50 g, 3.64 mmol) followed by ACN (4.5 mL), DMSO (2.25 mL), and DIPEA (2.5 mL). Guanidine hemicarbonate ([NH$_2$C(=NH)NH$_2$]$_2$.H$_2$CO$_3$) (853 mg, 4.73 mmol) was added, followed by 2-(bis(methylthio)methylene)malononitrile (619 mg, 3.64 mmol). The reaction mixture was stirred at 15° C. for five minutes and then heated to reflux for 7 hours, cooled to room temperature, and stirred overnight. HPLC analysis showed greater than 99% conversion of the amine starting material. Water (6 mL) was slowly added to afford a slurry, which was stirred at RT for one hour. The solids were filtered, washed with water (2×3 mL) and dried to give a hydrate of the title compound as a white solid (1.14 g).

Example 30

2,4-Diamino-6-(((1S)-1-(6-(3,5-dimethylisoxazol-4-yl)-1-methyl-1H-pyrrolo[3,2-b]pyridin-5-yl)ethyl)amino)pyrimidine-5-carbonitrile

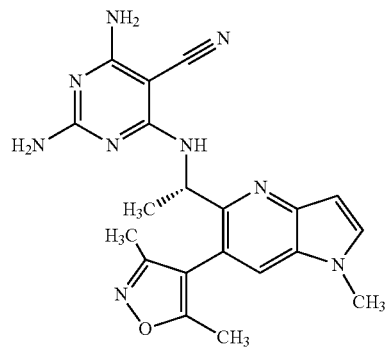 [SMILES: Cc1noc(C)c1-c1cc2c(ccn2C)nc1[C@H](C)Nc1nc(N)nc(N)c1C#N]

(1S)-1-(6-(3,5-Dimethylisoxazol-4-yl)-1-methyl-1H-pyrrolo[3,2-b]pyridin-5-yl)ethanamine (106 mg, 0.393 mmol), 2,4-diamino-6-chloropyrimidine-5-carbonitrile (100 mg, 0.590 mmol), and N-ethyl-N-isopropylpropan-2-amine (0.205 mL, 1.179 mmol) were combined in acetonitrile (6 mL). The reaction mixture was heated in a microwave reactor at 120° C. for 2 hours and then concentrated. The residue was taken up in DMF and purified by preparative HPLC (basic mode) eluting with 35% ACN in water. The fractions containing the desired product were combined and concentrated in vacuo to give the title compound (89 mg, 56%). $^1$H NMR (500 MHz, CD$_3$OD) δ ppm 1.36 (ddd, J=13.42, 6.59, 1.46 Hz, 3 H), 2.01 (d, J=1.46 Hz, 2 H), 2.15 (d, J=1.95 Hz, 1 H), 2.18-2.21 (m, 1 H), 2.32 (d, J=1.46 Hz, 2 H), 3.86 (d, J=1.46 Hz, 3 H), 5.38-5.49 (m, 1 H), 6.67 (dd, J=2.20, 1.22 Hz, 1H), 7.58 (dd, J=2.93, 1.46 Hz, 1 H), 7.69 (d, J=5.86 Hz, 1 H); ESI-MS m/z [M+H]$^+$ calc'd for $C_{20}H_{21}N_9O$, 404; found 404.

Example 31

2-Amino-4-(((1S)-1-(6-(3,5-dimethylisoxazol-4-yl)-1-methyl-1H-pyrrolo[3,2-b]pyridin-5-yl)ethyl)amino)-6-methylpyrimidine-5-carbonitrile

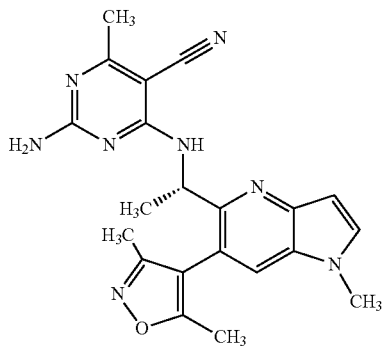 [SMILES: Cc1nc(N)nc(N[C@@H](C)c2nc3ccn(C)c3cc2-c2c(C)noc2C)c1C#N]

(1S)-1-(6-(3,5-Dimethylisoxazol-4-yl)-1-methyl-1H-pyrrolo[3,2-b]pyridin-5-yl)ethanamine (107 mg, 0.395 mmol), 2-amino-4-chloro-6-methylpyrimidine-5-carbonitrile (100 mg, 0.593 mmol), and N-ethyl-N-isopropylpropan-2-amine (0.21 mL, 1.2 mmol) were combined in acetonitrile (6 mL). The reaction mixture was heated in a microwave reactor at 120° C. for 2 hours and then concentrated. The residue was taken up in DMF and purified by preparative HPLC (basic mode) eluting with 45% ACN in water. The fractions containing the desired product were combined and concentrated in vacuo to give the title compound (62 mg, 39%). $^1$H NMR (500 MHz, CD$_3$OD) δ ppm 1.31-1.42 (m, 3 H), 2.01 (s, 2 H), 2.15 (s, 1 H), 2.19 (s, 1 H), 2.32 (d, J=4.39 Hz, 5 H), 3.86 (s, 3 H), 5.39-5.48 (m, 1 H), 6.65-6.69 (m, 1H), 7.59 (d, J=3.42 Hz, 1 H), 7.68-7.73 (m, 1 H); ESI-MS m/z [M+H]$^+$ calc'd for C$_2$H$_{22}$N$_8$O, 403; found 403.

Example 32

(S)-2,4-Diamino-6-((1-(6-(1-(difluoromethyl)-1H-pyrazol-5-yl)-1-methyl-1H-pyrrolo[3,2-b]pyridin-5-yl)ethyl)amino)pyrimidine-5-carbonitrile

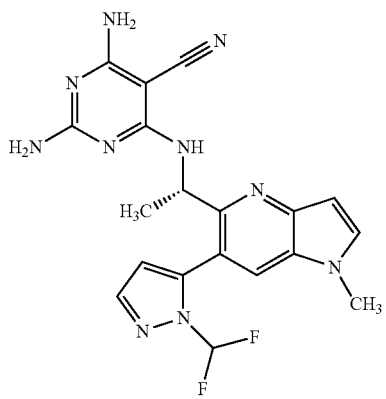 [SMILES: C[C@H](Nc1nc(N)nc(N)c1C#N)c1nc2ccn(C)c2cc1-c1ccnn1C(F)F]

(S)-1-(6-(1-(Difluoromethyl)-1H-pyrazol-5-yl)-1-methyl-1H-pyrrolo[3,2-b]pyridin-5-yl)ethanamine (115 mg, 0.393 mmol), 2-amino-4-chloro-6-methylpyrimidine-5-carbonitrile (100 mg, 0.593 mmol), and N-ethyl-N-isopropylpropan-2-amine (0.21 mL, 1.2 mmol) were combined in acetonitrile (6 mL). The reaction mixture was heated in a microwave reactor at 120° C. for 2 hours and then concentrated. The residue was taken up in DMF and purified by preparative HPLC (basic mode) eluting with 30-45% ACN in water. The fractions containing the desired compound were combined and extracted with EtOAc (200 mL). The combined organic layers were dried over Na$_2$SO$_4$, filtered, and concentrated in vacuo to give the title compound (97 mg, 58%). $^1$H NMR (500 MHz, CD$_3$OD) δ ppm 1.41-1.49 (m, 3 H), 3.88 (s, 3 H), 5.91 (q, J=6.67 Hz, 1 H), 6.63 (d, J=2.93 Hz, 1 H), 6.86 (d, J=2.44 Hz, 1 H), 7.49-7.77 (m, 2 H), 7.95 (s, 1 H), 8.19 (d, J=2.93 Hz, 1 H); ESI-MS m/z [M+H]$^+$ calc'd for C$_{19}$H$_{18}$F$_2$N$_{10}$, 425; found 425.

Example 33

(S)-5-Chloro-N$^4$-(1-(1-methyl-6-(1-methyl-1H-pyrazol-5-yl)-1H-pyrrolo[3,2-b]pyridin-5-yl)ethyl)pyrimidine-2,4,6-triamine

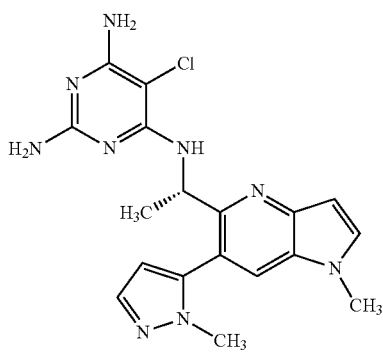 [SMILES: C[C@H](Nc1nc(N)nc(N)c1Cl)c1nc2ccn(C)c2cc1-c1ccnn1C]

(S)-1-(1-Methyl-6-(1-methyl-1H-pyrazol-5-yl)-1H-pyrrolo[3,2-b]pyridin-5-yl)ethanamine hydrochloride (95 mg, 0.372 mmol), 5,6-dichloropyrimidine-2,4-diamine (100 mg, 0.559 mmol), and N-ethyl-N-isopropylpropan-2-amine (0.20 mL, 1.1 mmol) were combined in acetonitrile (6 mL). The reaction mixture was heated in a microwave reactor at 120° C. for 2 hours and then at 160° C. for 1.5 hours. The mixture was concentrated. The residue was taken up in DMF and purified by preparative HPLC (basic mode) eluting with 30% ACN in water. The fractions containing the desired compound were combined and extracted with EtOAc (200 mL). The combined organic layers were dried over Na$_2$SO$_4$, filtered, and concentrated in vacuo to give the title compound (21 mg, 14%). $^1$H NMR (500 MHz, CD$_3$OD) δ ppm 1.38 (d, J=6.35 Hz, 3 H), 3.65 (s, 3 H), 3.83-3.89 (m, 3 H), 5.38 (q, J=6.67 Hz, 1 H), 6.40-6.46 (m, 1 H), 6.65-6.70 (m, 1 H), 7.58-7.64 (m, 2 H), 7.80 (s, 1 H); ESI-MS m/z [M+H]$^+$ calc'd for C$_{18}$H$_{20}$ClN$_9$, 398; found 398.

Example 34

(S)—N$^6$-(1-(1-Methyl-6-(pyridin-2-yl)-1H-pyrrolo[3,2-b]pyridin-5-yl)ethyl)-9H-purine-2,6-diamine

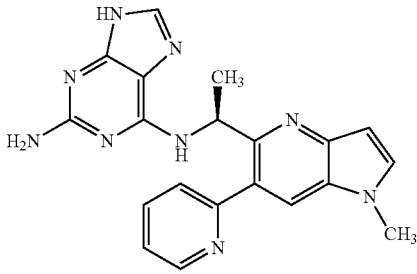 [SMILES: C[C@H](Nc1nc(N)nc2[nH]cnc12)c1nc2ccn(C)c2cc1-c1ccccn1]

(S)-1-(1-Methyl-6-(pyridin-2-yl)-1H-pyrrolo[3,2-b]pyridin-5-yl)ethanamine hydrochloride (511 mg, 1.77 mmol), 6-chloro-9H-purin-2-amine (200 mg, 1.18 mmol), and N-ethyl-N-isopropylpropan-2-amine (0.62 mL, 3.5 mmol)

were combined in acetonitrile (10 mL). The reaction mixture was heated in a microwave reactor at 120° C. for 2 hours and then concentrated. The residue was taken up in MeOH and DMSO and was purified by preparative HPLC (acid mode) eluting with 5-15% ACN in water. The fractions containing the desired compound were combined and concentrated in vacuo. The residue was recrystallized from EtOAc/MeOH/hexane to give a TFA salt of the title compound (15 mg, 3.3%). $^1$H NMR (500 MHz, CD$_3$OD) δ ppm 1.55-1.68 (m, 3 H), 3.95 (s, 3H), 5.81 (br s, 1 H), 6.68-6.79 (m, 1H), 7.51-7.59 (m, 1 H), 7.75-7.85 (m, 2 H), 7.99-8.10 (m, 2 H), 8.20 (br s, 1 H), 8.74 (d, J=4.88 Hz, 1 H); ESI-MS m/z [M+H]$^+$ calc'd for C$_{20}$H$_{19}$N$_9$, 386; found 386.

Example 35

(S)-2,4-Diamino-6-((1-(6-(1-cyclopropyl-1H-pyrazol-5-yl)-1-methyl-1H-pyrrolo[3,2-b]pyridin-5-yl) ethyl)amino)pyrimidine-5-carbonitrile

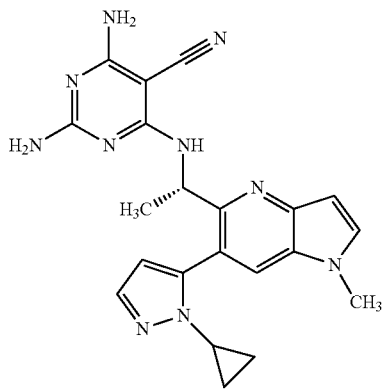 [SMILES: C[C@H](Nc1nc(N)nc(N)c1C#N)c1nc2ccn(C)c2cc1-c1ccnn1C1CC1]

(S)-1-(6-(1-Cyclopropyl-1H-pyrazol-5-yl)-1-methyl-1H-pyrrolo[3,2-b]pyridin-5-yl)ethanamine (151 mg, 0.536 mmol), 2,4-diamino-6-chloropyrimidine-5-carbonitrile (100 mg, 0.590 mmol), and N-ethyl-N-isopropylpropan-2-amine (0.280 mL, 1.61 mmol) were combined in acetonitrile (6 mL). The reaction mixture was heated in a microwave reactor at 120° C. for 2 hours and then concentrated. The residue was taken up in DMF and was purified by preparative HPLC (acid mode) eluting with 10-20% ACN in water. The fractions containing the desired product were combined and concentrated in vacuo to give a TFA salt of the title compound (91 mg, 41%). $^1$H NMR (500 MHz, CD$_3$OD) δ ppm 0.74-0.85 (m, 2H), 0.98-1.12 (m, 2 H), 1.47 (d, J=6.83 Hz, 3 H), 3.40 (tt, J=7.32, 3.66 Hz, 1 H), 3.93 (s, 3H), 5.55 (q, J=6.51 Hz, 1 H), 6.48 (d, J=1.46 Hz, 1 H), 6.71-6.78 (m, 1 H), 7.57 (d, J=1.95 Hz, 1 H), 7.78 (d, J=2.93 Hz, 1 H), 8.11 (s, 1 H); ESI-MS m/z [M+H]$^+$ calc'd for C$_{21}$H$_{22}$N$_{10}$, 415; found 415.

Example 36

(S)-N$^6$-(1-(6-(1-Cyclopropyl-1H-pyrazol-5-yl)-1-methyl-1H-pyrrolo[3,2-b]pyridin-5-yl)ethyl)-9H-purine-2,6-diamine

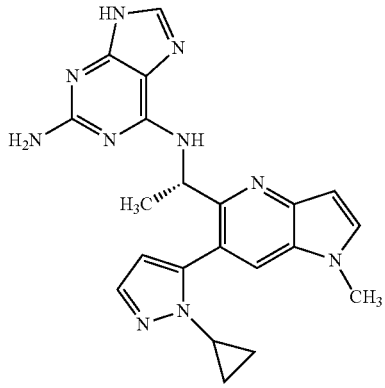 [SMILES: C[C@H](Nc1nc(N)nc2[nH]cnc12)c1nc2ccn(C)c2cc1-c1ccnn1C1CC1]

(S)-1-(6-(1-Cyclopropyl-1H-pyrazol-5-yl)-1-methyl-1H-pyrrolo[3,2-b]pyridin-5-yl)ethanamine (166 mg, 0.590 mmol), 6-chloro-9H-purin-2-amine (100 mg, 0.590 mmol), and N-ethyl-N-isopropylpropan-2-amine (0.31 mL, 1.8 mmol) were combined in acetonitrile (6 mL). The reaction mixture was heated in a microwave reactor at 120° C. for 2 hours and then concentrated. The residue was taken up in DMF and was purified by preparative HPLC (acid mode) eluting with 10-15% ACN in water. The fractions containing the desired compound were combined and concentrated in vacuo. The residue was further purified by preparative HPLC (basic mode) eluting with 25-35% ACN in water. The fractions containing the desired product were combined and concentrated in vacuo to give the title compound as a white solid (23 mg, 9.2%). $^1$H NMR (500 MHz, CD$_3$OD) δ ppm 0.59-0.75 (m, 2 H), 0.87-1.03 (m, 2H), 1.50 (d, J=6.35 Hz, 3 H), 3.38-3.47 (m, 1 H), 3.87 (d, J=0.98 Hz, 3 H), 5.56 (br s, 1 H), 6.44 (s, 1 H), 6.70 (d, J=2.93 Hz, 1 H), 7.54-7.71 (m, 3 H), 7.83 (s, 1 H); ESI-MS m/z [M+H]$^+$ calc'd for C$_{21}$H$_{22}$N$_{10}$, 415; found 415.

Example 37

(S)-N$^6$-(1-(6-(1-(Difluoromethyl)-1H-pyrazol-5-yl)-1-methyl-1H-pyrrolo[3,2-b]pyridin-5-yl)ethyl)-9H-purine-2,6-diamine

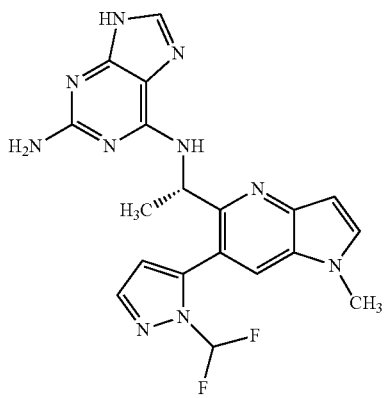 [SMILES: C[C@H](Nc1nc(N)nc2[nH]cnc12)c1nc2ccn(C)c2cc1-c1ccnn1C(F)F]

(S)-1-(6-(1-(Difluoromethyl)-1H-pyrazol-5-yl)-1-methyl-1H-pyrrolo[3,2-b]pyridin-5-yl)ethanamine (172 mg, 0.590 mmol), 6-chloro-9H-purin-2-amine (100 mg, 0.590 mmol), and N-ethyl-N-isopropylpropan-2-amine (0.31 mL, 1.8 mmol) were combined in acetonitrile (6 mL). The reaction mixture was heated in a microwave reactor at 120° C. for 2 hours and then concentrated. The residue was taken up in DMF and was purified by preparative HPLC (acid mode) eluting with 5-20% ACN in water. The fractions containing the desired compound were combined and concentrated in vacuo. The residue was further purified by preparative HPLC (basic mode) eluting with 25-35% ACN in water. The fractions containing the desired product were combined and concentrated in vacuo to give the title compound as a white solid. $^1$H NMR (500 MHz, CD$_3$OD) δ ppm 1.58 (d, J=6.83 Hz, 3 H), 3.87 (s, 3 H), 5.94-6.01 (m, 1 H), 6.64 (d, J=2.93 Hz, 1 H), 6.87 (d, J=2.44 Hz, 1 H), 7.46-7.76 (m, 2 H), 7.93 (s, 1 H), 8.18 (s, 1 H); ESI-MS m/z [M+H]$^+$ calc'd for C$_{19}$H$_{18}$F$_2$N$_{10}$, 425; found 425.

Example 38

5-Chloro-N$^4$-(1-(6-(3,3-difluoroazetidin-1-yl)-1-methyl-1H-pyrrolo[3,2-b]pyridin-5-yl)ethyl)pyrimidine-2,4,6-triamine

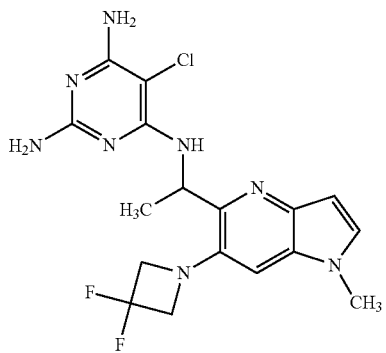 [SMILES: CC(Nc1nc(N)nc(N)c1Cl)c1nc2ccn(C)c2cc1N1CC(F)(F)C1]

To a 10 mL vial were added 1-(6-(3,3-difluoroazetidin-1-yl)-1-methyl-1H-pyrrolo[3,2-b]pyridin-5-yl)ethanamine (61 mg, 0.23 mmol), 5,6-dichloropyrimidine-2,4-diamine (41.0 mg, 0.229 mmol) and Et$_3$N (0.064 mL, 0.46 mmol) in DMF (2 mL). The resulting yellow solution was heated to 90° C. and stirred for 48 hours. The crude product was purified by preparative HPLC eluting with 30-55% ACN in water (with ammonium bicarbonate). The fractions containing the desired product were combined and lyophilized to give the title compound as a pale yellow solid (5 mg, 5%). $^1$H NMR (400 MHz, DMSO-d$_6$) δ ppm 1.29-1.41 (m, 3 H), 3.73-3.86 (m, 3 H), 4.17-4.35 (m, 2 H), 4.43-4.58 (m, 2 H), 5.33-5.48 (m, 1 H), 5.69-5.80 (m, 2 H), 5.89-6.01 (m, 2 H), 6.32-6.43 (m, 1 H), 6.45-6.54 (m, 1 H), 7.37-7.43 (m, 1 H), 7.45-7.51 (m, 1 H); ESI-MS m/z [M+H]$^+$ calc'd for C$_{17}$H$_{19}$ClF$_2$N$_8$, 409; found 409.

Example 39

2,4-Diamino-6-((1-(6-(3-hydroxyazetidin-1-yl)-1-methyl-1H-pyrrolo[3,2-b]pyridin-5-yl)ethyl)amino)pyrimidine-5-carbonitrile

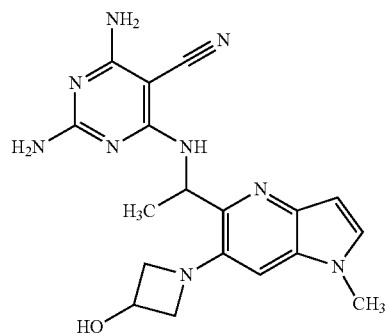 [SMILES: CC(Nc1nc(N)nc(N)c1C#N)c1nc2ccn(C)c2cc1N1CC(O)C1]

To a 10 mL vial were added 1-(5-(1-aminoethyl)-1-methyl-1H-pyrrolo[3,2-b]pyridin-6-yl)azetidin-3-ol (75 mg, 0.304 mmol), 2,4-diamino-6-chloropyrimidine-5-carbonitrile (62.0 mg, 0.365 mmol) and Et$_3$N (0.085 mL, 0.61 mmol) in acetonitrile (2 mL). The resulting yellow solution was heated to 90° C. and stirred overnight. The crude product was purified by preparative HPLC eluting with 20-40% ACN in water (with 0.05% ammonium bicarbonate). The fractions containing the desired product were combined and lyophilized to give the title compound as a pale yellow solid (5 mg, 5%). $^1$H NMR (400 MHz, DMSO-d$_6$) δ ppm 1.30-1.40 (m, 4 H), 3.47-3.58 (m, 1 H), 3.67-3.75 (m, 1 H), 3.75-3.80 (m, 4 H), 4.05-4.14 (m, 1 H), 4.20-4.33 (m, 1 H), 4.51-4.63 (m, 1 H), 5.40-5.53 (m, 1H), 5.57-5.68 (m, 1 H), 6.38-6.53 (m, 3 H), 6.54-6.66 (m, 2 H), 6.76-6.86 (m, 1 H), 7.10-7.20 (m, 1 H), 7.36-7.46 (m, 1 H); ESI-MS m/z [M+H]$^+$ calc'd for C$_{18}$H$_{21}$N$_9$O, 380; found 380.

Example 40

1-(5-(1-((2,6-Diamino-5-chloropyrimidin-4-yl)amino)ethyl)-1-methyl-1H-pyrrolo[3,2-b]pyridin-6-yl)azetidin-3-ol

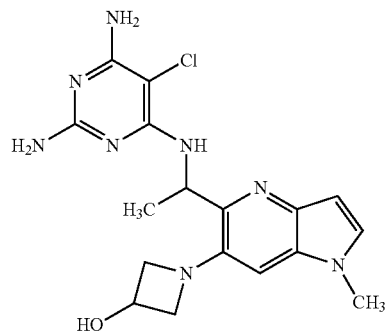 [SMILES: CC(Nc1nc(N)nc(N)c1Cl)c1nc2ccn(C)c2cc1N1CC(O)C1]

To a 10 mL vial were added 1-(5-(1-aminoethyl)-1-methyl-1H-pyrrolo[3,2-b]pyridin-6-yl)azetidin-3-ol (75 mg, 0.304 mmol), 5,6-dichloropyrimidine-2,4-diamine (65.4 mg, 0.365 mmol) and Et$_3$N (0.085 mL, 0.61 mmol) in acetonitrile (2 mL) and water (0.5 mL). The resulting brown solution was heated to 90° C. and stirred overnight. The crude product was purified by preparative HPLC eluting with 20-40% ACN in water (with 0.05% ammonium bicarbonate). The fractions containing the desired product were combined and lyophilized to give the title compound as an off-white solid (10 mg, 8.5%). $^1$H NMR (400 MHz, DMSO-$d_6$) δ ppm 1.03-1.14 (m, 3 H), 1.28-1.37 (m, 3 H), 3.48-3.56 (m, 1 H), 3.65-3.74 (m, 1 H), 3.74-3.83 (m, 3 H), 4.02-4.15 (m, 1 H), 4.23-4.33 (m, 1 H), 4.51-4.61 (m, 1 H), 5.33-5.48 (m, 1 H), 5.56-5.63 (m, 1 H), 5.64-5.73 (m, 2 H), 5.86-6.00 (m, 2H), 6.40-6.52 (m, 2 H), 7.07-7.16 (m, 1 H), 7.35-7.46 (m, 1 H); ESI-MS m/z [M+H]$^+$ calc'd for $C_{17}H_{21}ClN_8O$, 389; found 389.

Example 41

(S)-2,4-Diamino-6-((1-(6-(3-methoxyazetidin-1-yl)-1-methyl-1H-pyrrolo[3,2-b]pyridin-5-yl)ethyl)amino)pyrimidine-5-carbonitrile

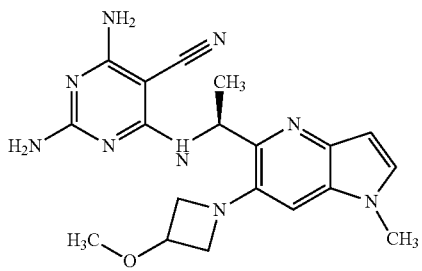 [SMILES: COC1CN(c2cc3c(ccn3C)nc2[C@H](C)Nc2nc(N)nc(N)c2C#N)C1]

(S)-1-(6-(3-Methoxyazetidin-1-yl)-1-methyl-1H-pyrrolo[3,2-b]pyridin-5-yl)ethanamine (469 mg, 1.80 mmol), 2,4-diamino-6-chloropyrimidine-5-carbonitrile (367 mg, 2.16 mmol), and N-ethyl-N-isopropylpropan-2-amine (628 µl, 3.60 mmol) were combined in acetonitrile (1.8 mL). The reaction mixture was heated in a microwave reactor at 120° C. for 2 hours. Additional 2,4-diamino-6-chloropyrimidine-5-carbonitrile (367 mg, 2.16 mmol) and N-ethyl-N-isopropylpropan-2-amine (628 µL, 3.60 mmol) were added. The reaction mixture was heated in a microwave reactor at 120° C. for 1 hour and then concentrated in vacuo. The residue was taken up in DMF and purified by preparative HPLC (basic mode) eluting with 25-50% ACN in water. The fractions containing the desired compound were combined and concentrated in vacuo. The residue was added to a silica gel column and was eluted with EtOAc. The fractions containing the desired product were combined and concentrated in vacuo to give the title compound as an off-white solid (106 mg, 15%). $^1$H NMR (500 MHz, CD$_3$OD) δ ppm 1.49 (d, J=6.83 Hz, 3 H), 3.40 (s, 3 H), 3.70-3.74 (m, 1 H), 3.82 (s, 3 H), 3.89 (dd, J=7.32, 4.39 Hz, 1 H), 4.15-4.20 (m, 1 H), 4.32-4.40 (m, 2 H), 5.64 (q, J=6.83 Hz, 1 H), 6.51 (dd, J=3.42, 0.98 Hz, 1 H), 7.20 (s, 1 H), 7.31 (d, J=2.93 Hz, 1 H); ESI-MS m/z [M+H]$^+$ calc'd for $C_{19}H_{23}N_9O$, 394.2; found 394.5.

Example 42

2,4-Diamino-6-((1-(6-(3,3-difluoroazetidin-1-yl)-1-methyl-1H-pyrrolo[3,2-b]pyridin-5-yl)ethyl)amino)pyrimidine-5-carbonitrile

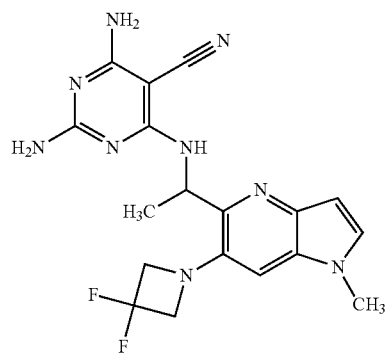 [SMILES: CC(Nc1nc(N)nc(N)c1C#N)c1nc2ccn(C)c2cc1N1CC(F)(F)C1]

To a 10 mL vial were added 1-(6-(3,3-difluoroazetidin-1-yl)-1-methyl-1H-pyrrolo[3,2-b]pyridin-5-yl)ethanamine (61 mg, 0.23 mmol) in DMF (2 mL) along with 2,4-diamino-6-chloropyrimidine-5-carbonitrile (38.8 mg, 0.229 mmol) and Et$_3$N (0.064 mL, 0.46 mmol). The resulting yellow solution was heated to 90° C. and stirred for 5 hours. The reaction mixture was diluted with EtOAc and washed with saturated NH$_4$Cl (3×). The combined organic layers were dried over MgSO$_4$, filtered, and concentrated. The product was precipitated with ether, filtered, and purified by silica gel column chromatography, eluting with 1:1 EtOAc/hexane to 100% EtOAc to 9:1 EtOAc/MeOH gradient. The resulting yellow foam was further purified by preparative HPLC eluting with 20-40% ACN in water (with 0.05% ammonium bicarbonate). The fractions containing the desired product were combined and lyophilized to give the title compound (racemate) as a white solid. $^1$H NMR (400 MHz, DMSO-$d_6$) δ ppm 1.29-1.43 (m, 3 H), 3.74-3.85 (m, 3 H), 4.18-4.37 (m, 2 H), 4.41-4.59 (m, 2 H), 5.38-5.52 (m, 1 H), 6.39-6.56 (m, 3 H), 6.57-6.65 (m, 2 H), 6.68-6.76 (m, 1H), 7.39-7.45 (m, 1 H), 7.46-7.53 (m, 1 H); ESI-MS m/z [M+H]$^+$ calc'd for $C_{18}H_{19}F_2N_9$, 400.2; found 400.4.

Example 43

(R)-2,4-Diamino-6-((1-(6-(3,3-difluoroazetidin-1-yl)-1-methyl-1H-pyrrolo[3,2-b]pyridin-5-yl)ethyl)amino)pyrimidine-5-carbonitrile

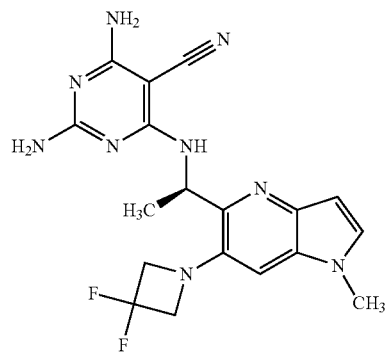 [SMILES: C[C@@H](Nc1nc(N)nc(N)c1C#N)c1nc2ccn(C)c2cc1N1CC(F)(F)C1]

Example 44

(S)-2,4-Diamino-6-((1-(6-(3,3-difluoroazetidin-1-yl)-1-methyl-1H-pyrrolo[3,2-b]pyridin-5-yl)ethyl)amino)pyrimidine-5-carbonitrile

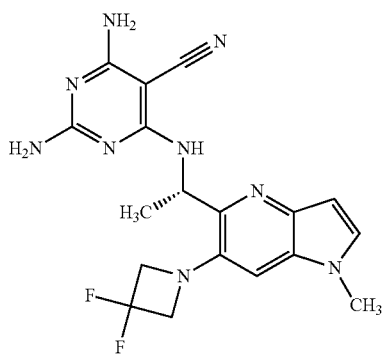 [SMILES: C[C@H](Nc1nc(N)nc(N)c1C#N)c1nc2ccn(C)c2cc1N1CC(F)(F)C1]

Racemic 2,4-diamino-6-((1-(6-(3,3-difluoroazetidin-1-yl)-1-methyl-1H-pyrrolo[3,2-b]pyridin-5-yl)ethyl)amino) pyrimidine-5-carbonitrile was resolved by Gilson supercritical fluid chromatography. EXAMPLE 43 stereoisomer was contained in fractions collected at the earliest retention time and was assigned R-stereochemical configuration. $^1$H NMR (400 MHz, DMSO-$d_6$) δ ppm 1.30-1.41 (m, 3 H), 3.74-3.85 (m, 3 H), 4.19-4.35 (m, 2 H), 4.42-4.58 (m, 2 H), 5.39-5.52 (m, 1 H), 6.40-6.56 (m, 3 H), 6.56-6.66 (m, 2 H), 6.66-6.78 (m, 1H), 7.39-7.45 (m, 1 H), 7.47-7.52 (m, 1 H); ESI-MS m/z [M+H]$^+$ calc'd for $C_{18}H_{19}F_2N_9$, 400.2; found 400.5. EXAMPLE 44 stereoisomer was contained in fractions collected at the later retention time was assigned S-stereochemical configuration. $^1$H NMR (400 MHz, DMSO-$d_6$) δ ppm 1.30-1.43 (m, 3 H), 3.75-3.85 (m, 3 H), 4.19-4.36 (m, 2 H), 4.42-4.59 (m, 2 H), 5.39-5.54 (m, 1 H), 6.41-6.56 (m, 3 H), 6.56-6.66 (m, 2 H), 6.66-6.77 (m, 1H), 7.39-7.46 (m, 1 H), 7.46-7.53 (m, 1 H); ESI-MS m/z [M+H]$^+$ calc'd for $C_{18}H_{19}F_2N_9$, 400.2; found 400.5.

Example 45

2,4-Diamino-6-((1-(1-methyl-6-(2-oxa-6-azaspiro[3.3]heptan-6-yl)-1H-pyrrolo[3,2-b]pyridin-5-yl)ethyl)amino)pyrimidine-5-carbonitrile

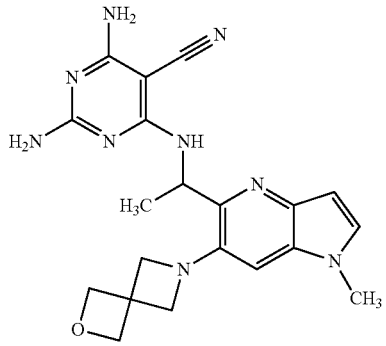

To a 10 mL vial were added 1-(1-methyl-6-(2-oxa-6-azaspiro[3.3]heptan-6-yl)-1H-pyrrolo[3,2-b]pyridin-5-yl)etha- namine (81 mg, 0.30 mmol), 2,4-diamino-6-chloropyrimidine-5-carbonitrile (50.4 mg, 0.297 mmol) and Et$_3$N (0.083 mL, 0.60 mmol) in DMF (2 mL). The resulting yellow solution was heated to 90° C. and stirred for 5 hours. The reaction mixture was diluted with EtOAc and washed with saturated NH$_4$Cl (3×). The combined organic layers were dried over MgSO$_4$, filtered, and concentrated. The desired compound was precipitated with ether, filtered, and purified by silica gel column chromatography, eluting with 1:1 EtOAc/hexane to 100% EtOAc to 9:1 EtOAc/MeOH gradient. The resulting yellow foam was further purified by preparative HPLC eluting with 20-40% ACN in water (with 0.05% ammonium bicarbonate). The fractions containing the product were combined and lyophilized to give the title compounds (racemate) as a white solid. $^1$H NMR (400 MHz, DMSO-$d_6$) δ ppm 1.28-1.40 (m, 3 H), 3.71-3.82 (m, 3 H), 3.96-4.07 (m, 2 H), 4.14-4.25 (m, 2 H), 4.72-4.85 (m, 4 H), 5.44-5.58 (m, 1 H), 6.37-6.45 (m, 1 H), 6.45-6.55 (m, 2H), 6.55-6.66 (m, 2 H), 6.68-6.79 (m, 1 H), 7.08-7.16 (m, 1 H), 7.37-7.45 (m, 1 H); ESI-MS m/z [M+H]$^+$ calc'd for $C_{20}H_{23}N_9O$, 406.2; found 406.5.

Example 46

(R)-2,4-Diamino-6-((1-(1-methyl-6-(2-oxa-6-azaspiro[3.3]heptan-6-yl)-1H-pyrrolo[3,2-b]pyridin-5-yl)ethyl)amino)pyrimidine-5-carbonitrile

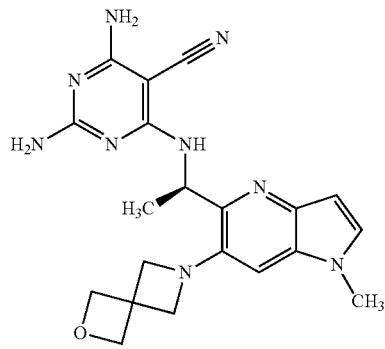 [SMILES: C[C@@H](Nc1nc(N)nc(N)c1C#N)c1nc2ccn(C)c2cc1N1CC2(COC2)C1]

Example 47

(S)-2,4-Diamino-6-((1-(1-methyl-6-(2-oxa-6-azaspiro[3.3]heptan-6-yl)-1H-pyrrolo[3,2-b]pyridin-5-yl)ethyl)amino)pyrimidine-5-carbonitrile

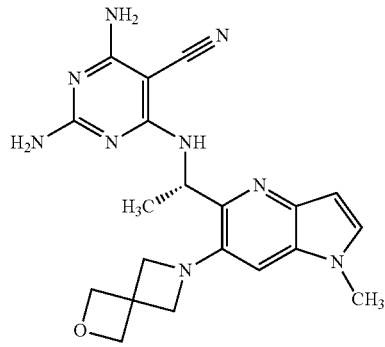 [SMILES: C[C@H](Nc1nc(N)nc(N)c1C#N)c1nc2ccn(C)c2cc1N1CC2(COC2)C1]

Racemic 2,4-diamino-6-((1-(1-methyl-6-(2-oxa-6-azaspiro[3.3]heptan-6-yl)-1H-pyrrolo[3,2-b]pyridin-5-yl)ethyl)amino)pyrimidine-5-carbonitrile was resolved by Gilson supercritical fluid chromatography. EXAMPLE 46 stereoisomer was contained in fractions collected at the earliest retention time and was assigned R-stereochemical configuration. $^1$H NMR (400 MHz, DMSO-$d_6$) δ ppm 1.29-1.39 (m, 3 H), 3.72-3.83 (m, 3 H), 3.98-4.07 (m, 2 H), 4.14-4.25 (m, 2 H), 4.70-4.84 (m, 4 H), 5.43-5.58 (m, 1 H), 6.40-6.45 (m, 1 H), 6.45-6.55 (m, 2 H), 6.56-6.65 (m, 2 H), 6.68-6.77 (m, 1 H), 7.07-7.15 (m, 1 H), 7.37-7.45 (m, 1 H); ESI-MS m/z [M+H]$^+$ calc'd for $C_{20}H_{23}N_9O$, 406.2; found 406.5. EXAMPLE 47 stereoisomer was contained in fractions collected at the later retention time and was assigned S-stereochemical configuration. $^1$H NMR (400 MHz, DMSO-$d_6$) δ ppm 1.28-1.40 (m, 3 H), 3.69-3.85 (m, 3 H), 3.97-4.08 (m, 2 H), 4.13-4.25 (m, 2 H), 4.72-4.84 (m, 4H), 5.44-5.58 (m, 1 H), 6.38-6.46 (m, 1 H), 6.46-6.56 (m, 2 H), 6.57-6.67 (m, 2 H), 6.69-6.79 (m, 1 H), 7.06-7.18 (m, 1 H), 7.36-7.46 (m, 1 H); ESI-MS m/z [M+H]$^+$ calc'd for $C_{20}H_{23}N_9O$, 406.2; found 406.5.

Example 48

(R)-2,4-Diamino-6-((1-(1-methyl-6-morpholino-1H-pyrrolo[3,2-b]pyridin-5-yl)ethyl)amino)pyrimidine-5-carbonitrile

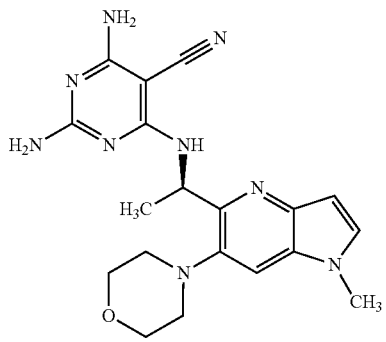 [SMILES: C[C@@H](Nc1nc(N)nc(N)c1C#N)c1nc2ccn(C)c2cc1N1CCOCC1]

To a 50 mL pear flask were added (R)-1-(1-methyl-6-morpholino-1H-pyrrolo[3,2-b]pyridin-5-yl)ethan-1-amine (0.5 g, 1.921 mmol) and 2,4-diamino-6-chloropyrimidine-5-carbonitrile (0.326 g, 1.92 mmol) in DMF (9.60 mL) to give a white suspension. To the suspension was added Et$_3$N (0.535 mL, 3.84 mmol) and the mixture was stirred at 100° C. for 6 hours. The mixture was allowed to stand at RT overnight. Saturated aqueous sodium bicarbonate solution (100 mL) was added, and the mixture was extracted with EtOAc (3×). The organic layers were combined, dried over MgSO$_4$, filtered, and concentrated. The damp residue was slurried in Et$_2$O. The solids were collected on a fritted glass funnel and washed with Et$_2$O. UPLC indicated the presence of a small impurity having a slightly shorter retention time than the desired product. The solids were dissolved in hot EtOH and recrystallized overnight to give the title compound as an off-white solid (340 mg, 45.0%). $^1$H NMR (400 MHz, DMSO-$d_6$) δ ppm 1.39 (d, J=6.32 Hz, 3 H), 2.70-2.83 (m, 2 H), 3.05 (br s, 2 H), 3.72-3.91 (m, 7 H), 5.90 (quin, J=6.76 Hz, 1 H), 6.41 (s, 2 H), 6.45-6.53 (m, 2 H), 6.58 (s, 2 H), 7.51-7.61 (m, 1 H), 7.84 (s, 1 H); ESI-MS m/z [M+H]$^+$ calc'd for $C_{19}H_{23}N_9O$, 394; found 394.

Example 49

(S)-2,4-Diamino-6-((1-(3-hydroxy-1-methyl-6-morpholino-1H-pyrrolo[3,2-b]pyridin-5-yl)ethyl)amino)pyrimidine-5-carbonitrile

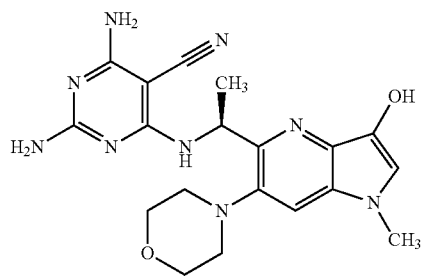 [SMILES: C[C@H](Nc1nc(N)nc(N)c1C#N)c1nc2c(O)cn(C)c2cc1N1CCOCC1]

1N NaOH was added to a 50 mL pear flask charged with (S)-5-(1-((2,6-diamino-5-cyanopyrimidin-4-yl)amino)ethyl)-1-methyl-6-morpholino-1H-pyrrolo[3,2-b]pyridin-3-yl acetate (3.29 g, 7.29 mmol) in methanol (25 mL). The reaction was complete within about 15 minutes. Saturated sodium bicarbonate solution was added. The aqueous layer was extracted with EtOAc (3×). The combined organic layers were dried over MgSO$_4$, filtered, and concentrated. The crude product was purified by preparative HPLC (acid mode, 5% to 25% ACN/water gradient). The product-containing fractions were pooled, neutralized with saturated sodium bicarbonate, and then extracted with EtOAc (3×). The combined organic layers were dried over MgSO$_4$, filtered, and concentrated to give the title compound as an off-white solid (210 mg, 7.04%). $^1$H NMR (400 MHz, DMSO-$d_6$) δ ppm 1.34 (d, J=6.57 Hz, 3 H), 2.70-2.80 (m, 2 H), 2.96-3.07 (m, 2 H), 3.15 (s, 3 H), 3.63 (d, J=2.53 Hz, 2 H), 3.71-3.88 (m, 4 H), 5.78-5.96 (m, 1 H), 6.07 (s, 1 H), 6.41 (br s, 2 H), 6.60 (s, 2 H), 7.33 (s, 1 H); ESI-MS m/z [M+H]$^+$ calc'd for $C_{19}H_{23}N_9O_2$, 410; found 410.

TABLE 1 lists PI3Kδ inhibition data for many of the compounds described in the examples, where larger pIC$_{50}$ values represent higher potency. The compounds were tested in accordance with the assay described on page 41 of the specification.

TABLE 1

| PI3Kδ Inhibition (pIC$_{50}$) for Example Compounds | |
|---|---|
| Example No. | pIC$_{50}$ |
| 1 | 6.9 |
| 2 | 8.6 |
| 3 | 8.8 |
| 4 | 7.2 |
| 5 | 6.9 |
| 6 | 7.2 |
| 7 | 4.1 |
| 8 | 6.0 |
| 9 | 9.1 |
| 10 | >8.6 |
| 11 | 5.9 |
| 12 | 8.8 |
| 13 | 8.7 |
| 14 | 8.1 |
| 15 | >9.0 |
| 16 | 8.1 |
| 17 | >9.0 |
| 18 | 6.3 |
| 19 | 8.3 |

TABLE 1-continued

PI3Kδ Inhibition (pIC$_{50}$) for Example Compounds

| Example No. | pIC$_{50}$ |
|---|---|
| 20 | — |
| 21 | 8.3 |
| 22 | 5.7 |
| 23 | >9.0 |
| 24 | >9.0 |
| 25 | >8.9 |
| 26 | >8.7 |
| 27 | 8.0 |
| 28 | 6.9 |
| 29 | >8.9 |
| 30 | >9.0 |
| 31 | 8.4 |
| 32 | 8.8 |
| 33 | 7.5 |
| 34 | 8.3 |
| 35 | 8.6 |
| 36 | 8.0 |
| 37 | 8.0 |
| 38 | 6.8 |
| 39 | >8.8 |
| 40 | 7.1 |
| 41 | >8.8 |
| 42 | — |
| 43 | 6.0 |
| 44 | 8.7 |
| 45 | — |
| 46 | 6.7 |
| 47 | 7.8 |
| 48 | 7.1 |
| 49 | 6.6 |

As used in the description and the claims, singular articles such as "a," "an," and "the," may refer to a single object or to a plurality of objects unless the context clearly indicates otherwise. Thus, for example, reference to a composition containing "a compound" may include a single compound or two or more compounds. The above description is intended to be illustrative and not restrictive. Therefore, the scope of the invention should be determined with reference to the claims and includes the full scope of equivalents to which such claims are entitled. The disclosures of all articles and references, including patents and published patent applications, are herein incorporated by reference in their entirety and for all purposes.

What is claimed is:

1. A compound of Formula 1,

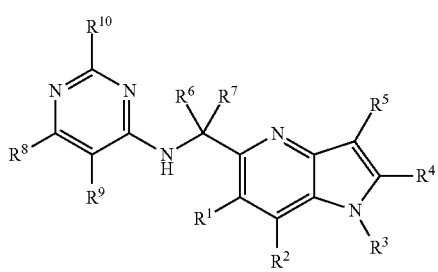

or a pharmaceutically acceptable salt thereof, wherein:
$R^1$ is selected from $C_{3-8}$ cycloalkyl, $C_{2-6}$ heterocyclyl, $C_{6-14}$ aryl, and $C_{1-9}$ heteroaryl, each optionally substituted with from one to five substituents independently selected from halo, oxo, —CN, $R^{11}$, and $R^{12}$;
$R^2$, $R^4$, and $R^5$ are each independently selected from hydrogen, halo, —OH, —CN, $C_{1-3}$ alkyl, and $C_{1-3}$ haloalkyl;
$R^3$ is selected from hydrogen, $C_{1-3}$ alkyl, and $C_{1-3}$ haloalkyl;
$R^6$ and $R^7$ are each independently selected from hydrogen, $C_{1-3}$ alkyl, and $C_{1-3}$ haloalkyl;
$R^8$ is selected from hydrogen, methyl, and —NH$_2$;
$R^9$ is selected from hydrogen, halo, —CN, $C_{1-3}$ haloalkyl, —OR$^{16}$, —C(O)R$^{16}$, —C(O)OR$^{16}$, —C(O)N(R$^{16}$)R$^{17}$, —C(O)N(R$^{16}$)OR$^{17}$, —C(O)N(R$^{16}$)S(O)$_2$R$^{18}$, SR$^{16}$, —S(O)R$^{18}$, —S(O)$_2$R$^{18}$, and —S(O)$_2$N(R$^{16}$)R$^{17}$; or
$R^8$ is selected from —NH— and —CH$_2$—, and $R^8$ and $R^9$, together with the carbon atoms to which they are attached, form a $C_{2-4}$ heteroarylene having 5 ring atoms and 1 to 3 heteroatoms, each of the heteroatoms being nitrogen, and wherein the $C_{2-4}$ heteroarylene is optionally substituted with $R^{12}$;
$R^{10}$ is selected from halo, —OH, $C_{1-3}$ alkyl, —NHR$^{16}$, and —NHC(O)R$^{16}$;
each $R^{11}$ is independently selected from —OR$^{13}$, —N(R$^{13}$)R$^{14}$, —NR$^{13}$C(O)R$^{14}$, —NHC(O)NR$^{13}$R$^{14}$, —NR$^{13}$C(O)NHR$^{14}$, —C(O)R$^{13}$, —C(O)OR$^{13}$, —C(O)N(R$^{13}$)R$^{14}$, —C(O)N(R$^{13}$)OR$^{14}$, —C(O)N(R$^{13}$)S(O)$_2$R$^{12}$, —N(R$^{13}$)S(O)$_2$R$^{12}$, —SR$^{13}$, —S(O)R$^{12}$, —S(O)$_2$R$^{12}$, and —S(O)$_2$N(R$^{13}$)R$^{14}$;
each $R^{12}$ is independently selected from $C_{1-6}$ alkyl, $C_{2-6}$ alkenyl, $C_{2-6}$ alkynyl, $C_{3-8}$ cycloalkyl-(CH$_2$)$_m$—, $C_{6-14}$ aryl-(CH$_2$)$_m$—, $C_{2-6}$ heterocyclyl-(CH$_2$)$_m$—, and $C_{1-9}$ heteroaryl-(CH$_2$)$_m$—, each optionally substituted with from one to five substituents independently selected from halo, oxo, —CN, $C_{1-6}$ alkyl, $C_{1-6}$ haloalkyl, and $R^{15}$;
each $R^{13}$ and $R^{14}$ is independently selected from
(a) hydrogen; and
(b) $C_{1-6}$ alkyl, $C_{2-6}$ alkenyl, $C_{2-6}$ alkynyl, $C_{3-6}$ cycloalkyl-(CH$_2$)$_m$—, $C_{6-14}$ aryl-(CH$_2$)$_m$—, $C_{2-6}$ heterocyclyl-(CH$_2$)$_m$—, and $C_{1-9}$ heteroaryl-(CH$_2$)$_m$—, each optionally substituted with from one to five substituents independently selected from halo, oxo, —CN, $C_{1-6}$ alkyl, $C_{1-6}$ haloalkyl, and $R^{15}$;
each $R^{15}$ is independently selected from –OR$^{16}$, —N(R$^{16}$)R$^{17}$, —N(R$^{16}$)C(O)R$^{17}$, —NHC(O)NR$^{16}$R$^{17}$, —NR$^{16}$C(O)NHR$^{17}$, —C(O)R$^{16}$, —C(O)OR$^{16}$, —C(O)N(R$^{16}$)R$^{17}$, —C(O)N(R$^{16}$)OR$^{17}$, —C(O)N(R$^{16}$)S(O)$_2$R$^{18}$, —NR$^{16}$S(O)$_2$R$^{18}$, —SR$^{16}$, —S(O)R$^{18}$, —S(O)$_2$R$^{18}$, and —S(O)$_2$N(R$^{16}$)R$^{17}$;
each $R^{16}$ and $R^{17}$ is independently selected from hydrogen, $C_{1-6}$ alkyl, and $C_{3-6}$ cycloalkyl;
each $R^{18}$ is independently selected from $C_{1-6}$ alkyl and $C_{3-6}$ cycloalkyl;
each m is independently selected from 0, 1, 2, 3, and 4;
wherein each of the aforementioned heteroaryl moieties independently has 1 to 4 heteroatoms independently selected from N, O, and S, and each of the aforementioned heterocyclyl moieties independently has 1 to 4 heteroatoms independently selected from N, O, and S.

2. A compound or pharmaceutically acceptable salt according to claim 1, wherein $R^1$ is selected from pyrazolyl, thiazolyl, isoxazolyl, phenyl, pyridinyl, azetidinyl, 1,2-dihydropyridinyl, piperidinyl, tetrahydropyranyl, morpholinyl, and 2-oxa-6-azaspiro[3.3]heptanyl, each optionally substituted.

3. A compound or pharmaceutically acceptable salt according to claim 1, wherein $R^1$ is selected from pyrazolyl, thiazolyl, isoxazolyl, pyridinyl, azetidinyl, piperidinyl, tetrahydropyranyl, morpholinyl, and 2-oxa-6-azaspiro[3.3]heptanyl, each optionally substituted.

4. A compound or pharmaceutically acceptable salt according to claim 1, wherein R$^1$ is selected from pyrazolyl, pyridinyl, and morpholinyl, each optionally substituted.

5. A compound or pharmaceutically acceptable salt according to claim 1, wherein R$^2$, R$^4$, and R$^5$ are each independently selected from hydrogen and halo.

6. A compound or pharmaceutically acceptable salt according to claim 1, wherein (a) R$^2$, R$^4$, and R$^5$ are each hydrogen, (b) R$^4$ and R$^5$ are each hydrogen and R$^2$ is halo, (c) R$^2$ and R$^5$ are each hydrogen and R$^4$ is halo, or (d) R$^2$ and R$^4$ are each hydrogen and R$^5$ is halo.

7. A compound or pharmaceutically acceptable salt according to claim 1, wherein each of R$^2$ and R$^4$ is hydrogen.

8. A compound or pharmaceutically acceptable salt according to claim 1, wherein R$^3$ is C$_{1-3}$ alkyl or C$_{1-3}$ haloalkyl.

9. A compound or pharmaceutically acceptable salt according to claim 8, wherein R$^3$ is methyl.

10. A compound or pharmaceutically acceptable salt according to claim 1, wherein one of R$^6$ and R$^7$ is hydrogen.

11. A compound or pharmaceutically acceptable salt according to claim 10, wherein one of R$^6$ and R$^7$ is C$_{1-3}$ alkyl.

12. A compound or pharmaceutically acceptable salt according to claim 1, wherein R$^8$ is selected from methyl and —NH$_2$.

13. A compound or pharmaceutically acceptable salt according to claim 1, wherein R$^9$ is selected from halo, —CN, and C$_{1-3}$ haloalkyl.

14. A compound or pharmaceutically acceptable salt according to claim 13, wherein R$^9$ is —CN.

15. A compound or pharmaceutically acceptable salt according to claim 1, wherein R$^8$ is —NH—, and R$^8$ and R$^9$, together with the carbon atoms to which they are attached, form a 1H-imidazol-4,5-diyl or a 1H-pyrazol-4,5-diyl, each optionally substituted.

16. A compound or pharmaceutically acceptable salt according to claim 1, wherein R$^{10}$ is —NH$_2$.

17. A compound according to claim 1, which is selected from the following compounds:
   (S)-5-Chloro-N$^4$-(1-(1-methyl-6-(1-methyl-1H-pyrazol-5-yl)-1H-pyrrolo[3,2-b]pyridin-5-yl)ethyl)pyrimidine-2,4-diamine;
   (S)-2,4-Diamino-6-((1-(1-methyl-6-(1-methyl-1H-pyrazol-5-yl)-1H-pyrrolo[3,2-b]pyridin-5-yl)ethyl)amino)pyrimidine-5-carbonitrile;
   (S)-2-Amino-4-methyl-6-((1-(1-methyl-6-(1-methyl-1H-pyrazol-5-yl)-1H-pyrrolo[3,2-b]pyridin-5-yl)ethyl)amino)pyrimidine-5-carbonitrile;
   (S)-2-Amino-4-((1-(1-methyl-6-(1-methyl-1H-pyrazol-5-yl)-1H-pyrrolo[3,2-b]pyridin-5-yl)ethyl)amino)pyrimidine-5-carbonitrile;
   (S)-5-Chloro-N$^4$-(1-(1-methyl-6-morpholino-1H-pyrrolo[3,2-b]pyridin-5-yl)ethyl)pyrimidine-2,4-diamine;
   4-Amino-2-methyl-6-((1-(1-methyl-6-morpholino-1H-pyrrolo[3,2-b]pyridin-5-yl)ethyl)amino)pyrimidine-5-carbonitrile;
   (S)-5-Fluoro-N$^4$-(1-(1-methyl-6-(1-methyl-1H-pyrazol-5-yl)-1H-pyrrolo[3,2-b]pyridin-5-yl)ethyl)pyrimidine-2,4-diamine;
   (S)-4-Amino-2-hydroxy-6-((1-(1-methyl-6-morpholino-1H-pyrrolo[3,2-b]pyridin-5-yl)ethyl)amino)pyrimidine-5-carbonitrile;
   (S)-2-Amino-4-methyl-6-((1-(1-methyl-6-morpholino-1H-pyrrolo[3,2-b]pyridin-5-yl)ethyl)amino)pyrimidine-5-carbonitrile;
   (S)-2,4-Diamino-6-((1-(1-methyl-6-morpholino-1H-pyrrolo[3,2-b]pyridin-5-yl)ethyl)amino)pyrimidine-5-carbonitrile;
   (S)-4-Amino-2-hydroxy-6-((1-(1-methyl-6-(1-methyl-1H-pyrazol-5-yl)-1H-pyrrolo[3,2-b]pyridin-5-yl)ethyl)amino)pyrimidine-5-carbonitrile;
   (S)-2,4-Diamino-6-((1-(1-methyl-6-(pyridin-2-yl)-1H-pyrrolo[3,2-b]pyridin-5-yl)ethyl)amino)pyrimidine-5-carbonitrile;
   (S)-2,4-Diamino-6-((1-(1-methyl-6-(1H-pyrazol-5-yl)-1H-pyrrolo[3,2-b]pyridin-5-yl)ethyl)amino)pyrimidine-5-carbonitrile;
   2,4-Diamino-6-(((1S)-1-(6-(3,5-dimethyl-1H-pyrazol-4-yl)-1-methyl-1H-pyrrolo[3,2-b]pyridin-5-yl)ethyl)amino)pyrimidine-5-carbonitrile;
   (S)-2,4-Diamino-6-((1-(6-(2-hydroxypyridin-4-yl)-1-methyl-1H-pyrrolo[3,2-b]pyridin-5-yl)ethyl)amino)pyrimidine-5-carbonitrile;
   (S)-N$^6$-(1-(1-Methyl-6-(1-methyl-1H-pyrazol-5-yl)-1H-pyrrolo[3,2-b]pyridin-5-yl)ethyl)-9H-purine-2,6-diamine;
   (S)-2,4-Diamino-6-((1-(1-methyl-6-(thiazol-4-yl)-1H-pyrrolo[3,2-b]pyridin-5-yl)ethyl)amino)pyrimidine-5-carbonitrile;
   (S)-N$^4$-(1-(1-Methyl-6-(1-methyl-1H-pyrazol-5-yl)-1H-pyrrolo[3,2-b]pyridin-5-yl)ethyl)-1H-pyrazolo[3,4-d]pyrimidine-4,6-diamine;
   (S)-2-Amino-4-methyl-6-((1-(1-methyl-6-(3-methyl-1H-pyrazol-4-yl)-1H-pyrrolo[3,2-b]pyridin-5-yl)ethyl)amino)pyrimidine-5-carbonitrile;
   2,4-Diamino-6-((1-(6-(4-hydroxy-4-methylpiperidin-1-yl)-1-methyl-1H-pyrrolo[3,2-b]pyridin-5-yl)ethyl)amino)pyrimidine-5-carbonitrile;
   (S)-2,4-Diamino-6-((1-(6-(4-hydroxy-4-methylpiperidin-1-yl)-1-methyl-1H-pyrrolo[3,2-b]pyridin-5-yl)ethyl)amino)pyrimidine-5-carbonitrile;
   (R)-2,4-Diamino-6-((1-(6-(4-hydroxy-4-methylpiperidin-1-yl)-1-methyl-1H-pyrrolo[3,2-b]pyridin-5-yl)ethyl)amino)pyrimidine-5-carbonitrile;
   (S)-2-Amino-4-((1-(6-(2-hydroxypyridin-4-yl)-1-methyl-1H-pyrrolo[3,2-b]pyridin-5-yl)ethyl)amino)-6-methylpyrimidine-5-carbonitrile;
   (S)-2-Amino-4-methyl-6-((1-(1-methyl-6-(pyridin-2-yl)-1H-pyrrolo[3,2-b]pyridin-5-yl)ethyl)amino)pyrimidine-5-carbonitrile;
   (S)-2-Amino-4-methyl-6-((1-(1-methyl-6-(tetrahydro-2H-pyran-4-yl)-1H-pyrrolo[3,2-b]pyridin-5-yl)ethyl)amino)pyrimidine-5-carbonitrile;
   (S)-2,4-Diamino-6-((1-(1-methyl-6-(tetrahydro-2H-pyran-4-yl)-1H-pyrrolo[3,2-b]pyridin-5-yl)ethyl)amino)pyrimidine-5-carbonitrile;
   (S)-N$^6$-(1-(1-Methyl-6-morpholino-1H-pyrrolo[3,2-b]pyridin-5-yl)ethyl)-9H-purine-2,6-diamine;
   (S)-5-Chloro-N$^4$-(1-(1-methyl-6-morpholino-1H-pyrrolo[3,2-b]pyridin-5-yl)ethyl)pyrimidine-2,4,6-triamine;
   2,4-Diamino-6-(((1S)-1-(6-(3,5-dimethylisoxazol-4-yl)-1-methyl-1H-pyrrolo[3,2-b]pyridin-5-yl)ethyl)amino)pyrimidine-5-carbonitrile;
   2-Amino-4-(((1S)-1-(6-(3,5-dimethylisoxazol-4-yl)-1-methyl-1H-pyrrolo[3,2-b]pyridin-5-yl)ethyl)amino)-6-methylpyrimidine-5-carbonitrile;
   (S)-2,4-Diamino-6-((1-(6-(1-(difluoromethyl)-1H-pyrazol-5-yl)-1-methyl-1H-pyrrolo[3,2-b]pyridin-5-yl)ethyl)amino)pyrimidine-5-carbonitrile;
   (S)-5-Chloro-N$^4$-(1-(1-methyl-6-(1-methyl-1H-pyrazol-5-yl)-1H-pyrrolo[3,2-b]pyridin-5-yl)ethyl)pyrimidine-2,4,6-triamine;

(S)-N⁶-(1-(1-Methyl-6-(pyridin-2-yl)-1H-pyrrolo[3,2-b]pyridin-5-yl)ethyl)-9H-purine-2,6-diamine;

(S)-2,4-Diamino-6-((1-(6-(1-cyclopropyl-1H-pyrazol-5-yl)-1-methyl-1H-pyrrolo[3,2-b]pyridin-5-yl)ethyl)amino)pyrimidine-5-carbonitrile;

(S)-N⁶-(1-(6-(1-Cyclopropyl-1H-pyrazol-5-yl)-1-methyl-1H-pyrrolo[3,2-b]pyridin-5-yl)ethyl)-9H-purine-2,6-diamine;

(S)-N⁶-(1-(6-(1-(Difluoromethyl)-1H-pyrazol-5-yl)-1-methyl-1H-pyrrolo[3,2-b]pyridin-5-yl)ethyl)-9H-purine-2,6-diamine;

5-Chloro-N⁴-(1-(6-(3,3-difluoroazetidin-1-yl)-1-methyl-1H-pyrrolo[3,2-b]pyridin-5-yl)ethyl)pyrimidine-2,4,6-triamine;

2,4-Diamino-6-((1-(6-(3-hydroxyazetidin-1-yl)-1-methyl-1H-pyrrolo[3,2-b]pyridin-5-yl)ethyl)amino)pyrimidine-5-carbonitrile;

1-(5-(1-((2,6-Diamino-5-chloropyrimidin-4-yl)amino)ethyl)-1-methyl-1H-pyrrolo[3,2-b]pyridin-6-yl)azetidin-3-ol;

(S)-2,4-Diamino-6-((1-(6-(3-methoxyazetidin-1-yl)-1-methyl-1H-pyrrolo[3,2-b]pyridin-5-yl)ethyl)amino)pyrimidine-5-carbonitrile;

2,4-Diamino-6-((1-(6-(3,3-difluoroazetidin-1-yl)-1-methyl-1H-pyrrolo[3,2-b]pyridin-5-yl)ethyl)amino)pyrimidine-5-carbonitrile;

(R)-2,4-Diamino-6-((1-(6-(3,3-difluoroazetidin-1-yl)-1-methyl-1H-pyrrolo[3,2-b]pyridin-5-yl)ethyl)amino)pyrimidine-5-carbonitrile;

(S)-2,4-Diamino-6-((1-(6-(3,3-difluoroazetidin-1-yl)-1-methyl-1H-pyrrolo[3,2-b]pyridin-5-yl)ethyl)amino)pyrimidine-5-carbonitrile;

2,4-Diamino-6-((1-(1-methyl-6-(2-oxa-6-azaspiro[3.3]heptan-6-yl)-1H-pyrrolo[3,2-b]pyridin-5-yl)ethyl)amino)pyrimidine-5-carbonitrile;

(R)-2,4-Diamino-6-((1-(1-methyl-6-(2-oxa-6-azaspiro[3.3]heptan-6-yl)-1H-pyrrolo[3,2-b]pyridin-5-yl)ethyl)amino)pyrimidine-5-carbonitrile;

(S)-2,4-Diamino-6-((1-(1-methyl-6-(2-oxa-6-azaspiro[3.3]heptan-6-yl)-1H-pyrrolo[3,2-b]pyridin-5-yl)ethyl)amino)pyrimidine-5-carbonitrile;

(R)-2,4-Diamino-6-((1-(1-methyl-6-morpholino-1H-pyrrolo[3,2-b]pyridin-5-yl)ethyl)amino)pyrimidine-5-carbonitrile;

(S)-2,4-Diamino-6-((1-(3-hydroxy-1-methyl-6-morpholino-1H-pyrrolo[3,2-b]pyridin-5-yl)ethyl)amino)pyrimidine-5-carbonitrile;

a stereoisomer of any of the aforementioned compounds; and a pharmaceutically acceptable salt of any of the aforementioned compounds or stereoisomers.

18. A compound according to claim 1, which is (S)-2-Amino-4-methyl-6-((1-(1-methyl-6-morpholino-1H-pyrrolo[3,2-b]pyridin-5-yl)ethyl)amino)pyrimidine-5-carbonitrile or a pharmaceutically acceptable salt thereof.

19. A compound according to claim 1, which is (S)-2,4-Diamino-6-((1-(1-methyl-6-morpholino-1H-pyrrolo[3,2-b]pyridin-5-yl)ethyl)amino)pyrimidine-5-carbonitrile or a pharmaceutically acceptable salt thereof.

20. A compound according to claim 1, which is (S)-2,4-Diamino-6-((1-(6-(2-hydroxypyridin-4-yl)-1-methyl-1H-pyrrolo[3,2-b]pyridin-5-yl)ethyl)amino)pyrimidine-5-carbonitrile or a pharmaceutically acceptable salt thereof.

21. A compound according to claim 1, which is (S)-2,4-Diamino-6-((1-(1-methyl-6-(thiazol-4-yl)-1H-pyrrolo[3,2-b]pyridin-5-yl)ethyl)amino)pyrimidine-5-carbonitrile or a pharmaceutically acceptable salt thereof.

22. A compound according to claim 1, which is (S)-2-Amino-4-((1-(6-(2-hydroxypyridin-4-yl)-1-methyl-1H-pyrrolo[3,2-b]pyridin-5-yl)ethyl)amino)-6-methylpyrimidine-5-carbonitrile or a pharmaceutically acceptable salt thereof.

23. A compound according to claim 1, which is (S)-2-Amino-4-methyl-6((1-(1-methyl-6-(pyridin-2-yl)-1H-pyrrolo[3,2-b]pyridin-5-yl)ethyl)amino)pyrimidine-5-carbonitrile or a pharmaceutically acceptable salt thereof.

24. A compound according to claim 1, which is (S)-2-Amino-4-methyl-6-((1-(1-methyl-6-(tetrahydro-2H-pyran-4-yl)-1H-pyrrolo[3,2-b]pyridin-5-yl)ethyl)amino)pyrimidine-5-carbonitrile or a pharmaceutically acceptable salt thereof.

25. A compound according to claim 1, which is (S)-2,4-Diamino-6-((1-(1-methyl-6-(tetrahydro-2H-pyran-4-yl)-1H-pyrrolo[3,2-b]pyridin-5-yl)ethyl)amino)pyrimidine-5-carbonitrile or a pharmaceutically acceptable salt thereof.

26. A compound according to claim 1, which is 2,4-Diamino-6-(((1S)-1-(6-(3,5-dimethylisoxazol-4-yl)-1-methyl-1H-pyrrolo[3,2-b]pyridin-5-yl)ethyl)amino)pyrimidine-5-carbonitrile or a pharmaceutically acceptable salt thereof.

27. A compound according to claim 1, which is (S)-2,4-Diamino-6-((1-(6-(3-methoxyazetidin-1-yl)-1-methyl-1H-pyrrolo[3,2-b]pyridin-5-yl)ethyl)amino)pyrimidine-5-carbonitrile or a pharmaceutically acceptable salt thereof.

28. A compound according to claim 1, which is (S)-2,4-Diamino-6-((1-(1-methyl-6-(1-methyl-1H-pyrazol-5-yl)-1H-pyrrolo[3,2-b]pyridin-5-yl)ethyl)amino)pyrimidine-5-carbonitrile or a pharmaceutically acceptable salt thereof.

29. A compound according to claim 1, which is (S)-2,4-Diamino-6-((1-(1-methyl-6-(pyridin-2-yl)-1H-pyrrolo[3,2-b]pyridin-5-yl)ethyl)amino)pyrimidine-5-carbonitrile or a pharmaceutically acceptable salt thereof.

30. A compound according to claim 1, which is (S)-2,4-Diamino-6-((1-(1-methyl-6-(1H-pyrazol-5-yl)-1H-pyrrolo[3,2-b]pyridin-5-yl)ethyl)amino)pyrimidine-5-carbonitrile or a pharmaceutically acceptable salt thereof.

31. A compound according to claim 1, which is (S)-2,4-Diamino-6-((1-(6-(1-(difluoromethyl)-1H-pyrazol-5-yl)-1-methyl-1H-pyrrolo[3,2-b]pyridin-5-yl)ethyl)amino)pyrimidine-5-carbonitrile or a pharmaceutically acceptable salt thereof.

32. A compound according to claim 1, which is (S)-2,4-Diamino-6((1-(6-(3,3-difluoroazetidin-1-yl)-1-methyl-1H-pyrrolo[3,2-b]pyridin-5-yl)ethyl)amino)pyrimidine-5-carbonitrile or a pharmaceutically acceptable salt thereof.

33. A pharmaceutical composition comprising:
a compound or pharmaceutically acceptable salt as defined in claim 1; and
a pharmaceutically acceptable excipient.

34. A combination comprising a compound or pharmaceutically acceptable salt as defined in claim 1, and at least one additional pharmacologically active agent.

35. A method of making a compound of Formula 1 or a pharmaceutically acceptable salt thereof as defined in claim 1, the method comprising:
reacting a compound of Formula F1,

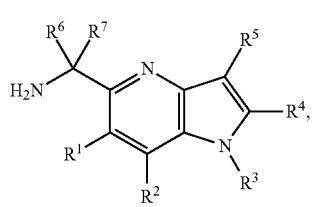

F1 or a salt thereof, with 2-(bis(methylthio)methylene)malononitrile and a compound of Formula F2,

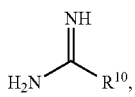

F2 or a salt thereof, in the presence of a base, to give a compound of Formula 1 or a salt thereof in which $R^8$ is —$NH_2$, $R^9$ is —CN, and $R^{10}$ is selected from —OH, $C_{1-3}$ alkyl, and —$NHR^{16}$; and optionally converting the compound of Formula 1 to a pharmaceutically acceptable salt;

wherein $R^1$, $R^2$, $R^3$, $R^4$, $R^5$, $R^6$, $R^7$, and $R^{16}$ are defined as for Formula 1.

* * * * *